United States Patent
Grinstaff et al.

(10) Patent No.: US 7,507,859 B2
(45) Date of Patent: Mar. 24, 2009

(54) FUNCTIONAL SYNTHETIC MOLECULES AND MACROMOLECULES FOR GENE DELIVERY

(75) Inventors: Mark W. Grinstaff, Boston, MA (US); Philippe Barthelemy, Mérignac (FR); Carla Prata, Allston, MA (US); Louis Moreau, Villeneuve lez Avignon (FR)

(73) Assignee: Fifth Base LLC, Casselberry, FL (US)

( * ) Notice: Subject to any disclaimer, the term of this patent is extended or adjusted under 35 U.S.C. 154(b) by 106 days.

(21) Appl. No.: 10/559,349

(22) PCT Filed: Jun. 16, 2004

(86) PCT No.: PCT/US2004/019230

§ 371 (c)(1),
(2), (4) Date: Jun. 16, 2006

(87) PCT Pub. No.: WO2005/007810

PCT Pub. Date: Jan. 27, 2005

(65) Prior Publication Data

US 2006/0241071 A1    Oct. 26, 2006

Related U.S. Application Data

(60) Provisional application No. 60/478,865, filed on Jun. 16, 2003.

(51) Int. Cl.
*C07C 233/00*    (2006.01)
*C07C 211/00*    (2006.01)
*C07C 229/00*    (2006.01)

(52) U.S. Cl. .................. 564/291; 564/282; 564/193; 564/199; 560/155

(58) Field of Classification Search .............. None
See application file for complete search history.

(56) References Cited

U.S. PATENT DOCUMENTS 3,062,858 A    11/1962    Cramer et al.

(Continued)

FOREIGN PATENT DOCUMENTS

JP    09087078    3/1997

OTHER PUBLICATIONS

Bennett et al., Journal of Medicinal Chemistry (1997), 40(25), 4069-4078.*

(Continued)

*Primary Examiner*—Karl J Puttlitz
(74) *Attorney, Agent, or Firm*—Dana M. Gordon; Foley Hoag LLP

(57) ABSTRACT

The present invention describes a synthetic non-viral vector composition for gene therapy and the use of such compositions for in vitro, ex vivo and/or in vivo transfer of genetic material. The invention proposes a pharmaceutical composition containing 1) a non-cationic amphiphilic molecule or macromolecule and its use for delivery of nucleic acids or 2) a cationic amphiphilic molecule or macromolecule that transforms from a cationic entity to an anionic, neutral, or zwitterionic entity by a chemical, photochemical, or biological reaction and its use for delivery of nucleic acids. Moreover this invention describes the use of these non-viral vector compositions in conjunction with a surface to mediate the delivery of nucleic acids. An additional embodiment is the formation of a hydrogel with these compositions and the use of this hydrogel for the delivery of genetic material. A further embodiment of this invention is the use of a change in ionic strength for the delivery of genetic material.

13 Claims, 5 Drawing Sheets

U.S. PATENT DOCUMENTS 6,419,894 B1 * 7/2002 Piccione et al. ............. 423/705

OTHER PUBLICATIONS

Hazard et al., Comptes Rendus des Seances de la Societe de Biologie et de Ses Filiales (1944), 138, 427-9.*

Rochovansky, et al., "Biosynthesis of Urea. Mechanism of Argininosuccinate Synthase Reaction", *J. Bio. Chem.*, 236:2254-60 (1961), Chemical Abstracts online citation on CAPLUS 1961:144667 [retrieved Feb. 2, 2006] Columbus, OH USA.

Tokunoh, et al., "Catalytic Asymmetric Intramolecular Cyclopropanation of Enol Sily Ether", *Tetrahedron Letters*, 37(14):2449-52 (1996), Chemical Abstracts online citation ofn CAPLUS 10669:213439 [retrieved Feb. 2, 2006], Columbus, OH USA.

International Search Report dated Apr. 21, 2006.

* cited by examiner

FUNCTIONAL SYNTHETIC MOLECULES AND MACROMOLECULES FOR GENE DELIVERY

RELATED APPLICATIONS

This application claims the benefit of priority to Patent Cooperation Treaty Application number PCT/US2004/019230, filed Jun. 16, 2004; which claims the benefit of priority to U.S. Provisional Patent Application Ser. No. 60/478,865, filed Jun. 16, 2003.

BACKGROUND OF THE INVENTION

In 1972, Friedmann outlined the far-reaching opportunities for human gene therapy. Friedmann, T.; Roblin, R. *Science* 1972, 175, 949-955. Chromosomal deficiencies and/or anomalies, e.g., mutation and aberrant expression, cause many hereditary and non-hereditary diseases. Conventional medicine remains unable to treat many of these diseases; gene therapy may be an effective therapeutic option by either adding, replacing, or removing relevant genes. See Kay, M. A.; Liu, D.; Hoogergrugge, P. M. *Proc. Natl. Acad. Sci.* 1997, 94, 12744-12746 and Huang, L.; Hung, M.; Wagner, E., Eds. *Nonviral Vectors for Gene Therapy*; Academic Press: New York, 1999.

Currently few organs or cells can be specifically targeted for gene delivery. There are established protocols for transferring genes into cells, including calcium phosphate precipitation, electroporation, particle bombardment, liposomal delivery, viral-vector delivery, and receptor-mediated gene-delivery. However, a main obstacle to the penetration of a nucleic acid into a cell or target organ lies in its size and polyanionic nature, both of which militate against its passage across cell membranes. Two strategies currently being explored for delivery of nucleic acids are viral and synthetic non-viral vectors, i.e., cationic molecules and polymers. A brief discussion of viral vectors, cationic lipids, and cationic polymers and there utility in gene therapy is presented below.

Viral Vectors

Viral vectors are viruses. Viruses, such as adenoviruses, herpes viruses, retroviruses and adeno-associated viruses, are currently under investigation. Currently, viral vectors, e.g., adenoviruses and adeno-associated viruses, have exhibited the highest levels of transfection efficiency compared to synthetic vectors, i.e., cationic lipids and polymers. Viral vectors suffer use in the Treatment of Human Diseases *Drugs* 2000, 60, 249-271; Smith, E. A. Viral Vectors in Gene Therapy *Annu. Rev. Microbiol.* 1995, 49, 807-838; Drumm, M. L.; Pope, H. A.; Cliff, W. H.; Rommens, J. M.; Marvin, S. A.; Tsui, L. C.; Collins, F. S.; Frizzell, R. A.; Wilson, J. M. Correction of the Cystic-fibrosis Defect in Vitro by Retrovirus-Mediated Gene Transfer *Cell* 1990, 1990, 1227-1233; Rosenfeld, M. A.; Yoshimura, K.; Trapnell, B. C.; Yoneyama, K.; Rosenthal, E. R.; Dalemans, W.; Fukayama, M.; Bargon, J.; Stier, L. E.; Stratfordperricaudet, L.; Perricaudet, M.; Guggino, W. B.; Pavirani, A.; Lecocq, J. P.; Crystal, R. G. In vivo Transfer of the Human Cystic-Fibrosis Transmembrane Conductance Regulator Gene to the Airway Epithelium *Cell* 1992, 68, 143-155; Muzyczka, N. Use of Adenoassociated Virus as a General Transduction Vector for Mammalian Cells *Curr. Top. Microbiol. Immuno.* 1992, 158, 97-129; Robbins, P. D.; Tahara, H.; Ghivizzani, S. C. Viral Vectors for Gene Therapy *Trends Biotechnol* 1998, 16, 35-40; and oss, G.; Erickson, R.; Knorr, D.; Motulsky, A. G.; Parkman, R.; Samulski, J.; Straus, S. E.; Smith, B. R. Gene Therapy in the United States: A Five-Year Status Report *Hum. Gene Ther.* 1996, 14, 1781-1790.

Since the method infects an individual cell with a viral carrier, a potentially life threatening immune response to the treatment can develop. Summerford reviews gene therapy with Adeno-associated viral vectors. For additional details see Marshall, E. Clinical Research—FDA Halts All Gene Therapy Trials at Penn *Science* 2000, 287, 565-567 and Summerford, C.; Samulski, R. J. Adeno-associated Viral Vectors for Gene Therapy *Biogenic Amines* 1998, 14, 451-475. Several examples of viral vectors used for gene delivery are described below. In U.S. Pat. No. 5,585,362 to Wilson et al., an improved adenovirus vector and methods for making and using such vectors is described. Likewise, U.S. Pat. No. 6,268,213 to Samulski et al., describes an adeno-associated virus vector and cis-acting regulatory and promoter elements capable of expressing at least one gene and method of using the viral vector for gene therapy. Although the transfection efficiency is high with viral vectors, there are a number of complications associated with the use of viral vectors.

Cationic Lipids

The second strategy consists of using non-viral agents capable of promoting the transfer and expression of DNA in cells. Since the first report by Felgner, this area has been actively investigated. These cationic non-viral agents bind to polyanionic DNA. Following endocytosis, the nucleic acid must escape from the delivery agent as well as the endosomal compartment so that the genetic material is incorporated within the new host The mechanism of nucleic acid transfer from endosomes to cytoplasm and/or nuclear targets is still unclear. Possible mechanisms are simple diffusion, transient membrane destabilization, or simple leakage during a fusion event in which endosomes fuse with other vesicles. See Felgner, P. L. Nonviral Strategies for Gene Therapy *Sci. Am.* 1997, 276, 102-106; Felgner, P. L.; Gadek, T. R.; Holm, M.; Roman, R.; Chan, H. W.; Wenz, M.; Northrop, J. P.; Ringgold, G. M.; Danielsen, M. Lipofectin: A highly efficient, lipid mediated DNA-transfection procedure *Proc. Natl. Acad. Sci. USA* 1987, 84, 7413-7417; Felgner, P. L.; Kumar, R.; Basava, C.; Border, R. C.; Hwang-Felgner, J. In; Vical, Inc. San Diego, Calif.: U.S. Pat. No. 5,264,618, 1993; Felgner, J. H.; Kumar, R.; Sridhar, C. N.; Wheeler, C. J.; Tsai, Y. J.; Border, R.; Ramsey, P.; Martin, M.; Felgner, P. L. Enhanced Gene Delivery and Mechanism Studies with a Novel Series of Cationic Formulations *J. Biol. Chem.* 1994, 269, 2550-2561; Freidmann, T. *Sci. Am.* 1997, 276, 96-101; Behr, J. P. Gene Transfer with Synthetic Cationic Amphiphiles: Prospects for Gene Delivery *Bioconjugate Chem.* 1994, 5, 382-389; Cotton, M.; Wagner, B. Non-viral Approaches to Gene Therapy *Curr. Op. Biotech.* 1993, 4, 705-710; Miller, A. D. Cationic Liposomes for Gene Therapy *Angew. Chem. Int.* 1998, 37, 1768-1785; Scherman, D.; Bessodes, M.; Cameron, B.; Herscovici, J.; Hofland, H.; Pitard, B.; Soubrier, F.; Wils, P.; Crouzet, J. Application of Lipids and Plasmid Design for Gene Delivery to Mammalian Cells *Curr. Op. Biotech.* 1989, 9, 480; Lasic, D. D. In *Surfactants in Cosmetics;* 2nd ed.; Rieger, M. M., Rhein, L. D., Eds.; Marcel Dekker, Inc.: New York, 1997; Vol. 68, pp 263-283; Rolland, A. P. From Genes to Gene Medicines: Recent Advances in Nonviral Gene Delivery *Crit. Rev. Ther. Drug* 1998, 15, 143-198; de Lima, M. C. P.; Simoes, S.; Pires, P.; Faneca, H.; Duzgunes, N. Cationic Lipid-DNA Complexes in Gene Delivery from Biophysics to Biological Applications *Adv. Drug. Del. Rev.* 2001, 47, 277-294.

These synthetic vectors have two main functions, to condense the DNA to be transfected and to promote its cell-binding and passage across the plasma membrane, and where appropriate, the two nuclear membranes. Due to its polyanionic nature, DNA naturally has poor affinity for the plasma membrane of cells, which is also polyanionic. Several groups have reported the use of amphiphilic cationic lipid-nucleic acid complexes for in vivo transfection both in animals and humans. Thus, non-viral vectors have cationic or polycationic charges. See Gao, X; Huang, L. Cationic Liposome-mediated Gene Transfer *Gene Therapy* 1995, 2, 710-722; Zhu, N.; Liggott, D.; Liu, Y.; Debs, R. Systemic Gene Expression After Intravenous DNA Delivery into Adult Mice *Science* 1993, 261, 209-211; Thierry, A. R.; Lunardiiskandar, Y.; Bryant, J. L.; Rabinovich, P.; Gallo, R. C.; Mahan, L. C. Systemic Gene-Therapy-Biodistribution and Long-Term Expression of a Transgene in Mice *Proc. Nat. Acad. Sci.* 1995, 92, 9742-9746.

Cationic amphiphilic compounds that possess both cationic and hydrophobic domains have been previously used for delivery of genetic information. In fact, this class of compounds is widely used for intracellular delivery of genes. Such cationic compounds can form cationic liposomes which are the most popular system synthetic vector for gene transfection studies. The cationic liposomes serve two functions. First, it protects the DNA from degradation. Second, it increases the amount of DNA entering the cell. While the mechanisms describing how cationic liposomes function have not been fully delineated, such liposomes have proven useful in both in vitro and in vivo studies. Safinya, C. R. describes the structure of the cationic amphiphile-DNA complex. See Radler, J. O.; Koltover, I.; Salditt, T.; Safinya, C. R. *Science* 1997, 275, 810-814; Templeton, N. S.; Lasic, D. D.; Frederik, P. M.; Strey, H. H.; Roberts, D. D.; Pavlakis, G. N. *Nature Biotech.* 1997, 15, 647-652; Koltover, I.; Salditt, T.; Radler, J. O.; Safinya, C. R. *Science* 1998, 281, 78-81; and Koltover, I.; Salditt, T.; Safinya, C. R. *Biophys. J.* 1999, 77, 915-924. Many of these systems for gene delivery in vitro and in vivo are reviewed in recent articles. See Remy, J.; Sirlin, C.; Vierling, P.; Behr, J. *Bioconj. Chem.* 1994, 5, 647-654; Crystal, R. G. *Science* 1995, 270, 404-410; Blaese, X.; et, a. *Cancer Gene Ther.* 1995, 2, 291-297; and Behr, J. P. and Gao, X cited above. Unlike viral vectors, the lipid-nucleic acid complexes can be used to transfer expression cassettes of essentially unlimited size.

Because these synthetic delivery systems lack proteins, they may evoke fewer immunogenic and inflammatory responses. However, the liposomes suffer from low transfection efficiencies. Moreover, as is the case with other polycations, cationic lipids and liposomes (e.g., Lipofectin®) can be toxic to the cells and inefficient in their DNA delivery in the presence of serum; see Leonetti et al. Behr, like Leonetti, reports that these cationic amphiphiles or lipids are adversely affected by serum and some are toxic. See Leonetti, J.; Machy, P.; Degols, G.; Lebleu, B.; Leserman, L. *Proc. Nat. Acad. Sci.* 1990, 87, 2448-2451 and Behr, J. P. *Acc. Chem. Res.* 1993, 26, 274-278.

Behr discloses numerous amphiphiles including dioctadecylamidologlycylspermine ("DOGS") for gene delivery. This material is commercially available as TRANSFECTAM®. Vigneron describes guanidinium-cholesterol cationic lipids for transfection of eukaryotic cells. Felgner discloses use of positively-charged synthetic cationic lipids including N-1-(2, 3-dioleyloxy)propyl-N,N,N-trimethylammonium chloride ("DOTMA"), to form lipid/DNA complexes suitable for transfections. Byk describes cationic lipids where the cationic portion of the amphiphile is either linear, branched, or globular for gene transfection. Blessing and coworkers describe a cationic synthetic vector based on spermine. Safinya describes cationic lipids containing a poly(ethylene glycol) segment for gene delivery. Bessodes and coworkers describe a cationic lipid containing glycosidic linker for gene delivery. Ren and Liu describe cationic lipids based on 1,2, 4-butanetriol. Tang and Scherman describe a cationic lipid that contains a disulfide linkage for gene delivery. Vierling describes highly fluorinated cationic amphiphiles as gene carrier and delivery systems. Jacopin describes a cation amphiphile for gene delivery that contains a targeting ligand. Wang and coworkers describe carnitine based cationic esters for gene delivery. Zhu describes the use of a cationic lipid, N[1-(2,3-dioleyloxy)propyl]-N,N,N-trimethylammonium chloride for the intravenous delivery of DNA. See Behr, J. P.; Demeneix, B.; Loeffler, J. P.; Perez-Mutul, J. Efficeint Gene Transfer into Mammalian Primary Endocrine Cells with Lipopolyamine Coated DNA *Proc. Nat. Acad. Sci.* 1989, 86, 6982-6986; Vigneron, J. P.; Oudrhiri, N.; Fauquet, M.; Vergely, L.; Bradley, J. C.; Basseville, M.; Lehn, P.; Lehn, J. M. *Proc. Nat. Acad. Sci.* 1996, 93, 9682-9686; Byk, G.; BDubertret, C.; Escriou, V.; Frederic, M.; Jaslin, G.; Rangara, R.; Pitard, B.; Wils, P.; Schwartz, B.; Scherman, D. *J. Med. Chem.* 1998, 41, 224-235; Blessing, T.; Remy, J. S.; Behr, J. P. *J. Am. Chem. Soc.* 1998, 120, 8519-8520; Blessing, T.; Remy, J. S.; Behr, J. P. *Proc. Nat. Acad. Sci.* 1998, 95, 1427-1431; Schulze, U.; Schmidt, H.; Safinya, C. R. *Bioconj. Chem.* 1999, 10, 548-552; Bessodes, M.; Dubertret, C.; Jaslin, G.; Scherman, D. *Bioorg. Med. Chem. Lett.* 2000, 10, 1393-1395; Herscovici, J.; Egron, M. J.; Quenot, A.; Leclercq, F.; Leforestier, N.; Mignet, N.; Wetzer, B.; Scherman, D. *Org. Lett.* 2001; Ren, T.; Liu, D. *Tetrahedron Lett.* 1999, 40, 7621-7625; Tang, F.; Hughes, J. A. *Biochem. Biophys. Res. Commun.* 1998, 242, 141-145; Tang, F.; Hughes, J. A. *Bioconjugate Chem.* 1999, 10, 791-796; Wetzer, B.; Byk, G.; Frederic, M.; Airiau, M.; Blanche, F.; Pitard, B.; Scherman, D. *Biochemical J.* 2001, 356, 747-756; Vierling, P.; Santaella, C.; Greiner, J. *J. Fluorine Chem.* 2001, 107, 337-354; Jacopin, J.; Hofland, H.; Scherman, D.; Herscovici, J. *J. Biomed. Chem. Lett.* 2001, 11, 419-422; and Wang, J.; Guo, X.; Xu, Y.; Barron, L.; Szoka, F. C. *J. Med. Chem.* 1998, 41, 2207-2215.

In U.S. Pat. No. 5,283,185 to Epand et al., the inventors describe additional examples of amphiphiles including a cationic cholesterol synthetic vector, termed "DC-chol". The inventors describe, in U.S. Pat. No. 5,264,6184, more cationic compounds that facilitate transport of biologically active molecules into cells. U.S. Pat. Nos. 6,169,078 and 6,153,434 to Hughes et al. disclose a cationic lipid that contains a disulfide bond for gene delivery. U.S. Pat. No. 5,334,761 to Gebeyehu et al. describes additional cationic amphiphiles suitable for intracellular delivery of biologically active molecules. U.S. Pat. No. 6,110,490 to Thierry describes additional cationic lipids for gene delivery. U.S. Pat. No. 6,056, 938 to Unger, et al. discloses cationic lipid compounds that contain at least two cationic groups.

Cationic Polymers

Recently, polymeric systems for gene delivery have been explored. In Han's review, he discussed most of the common cationic polymer systems including PLL, poly(L-lysine); PEI, polyethyleneimine; pDMEAMA, poly(2-dimethylamino)ethyl-methacrylate; PLGA, poly(D,L-lactide-co-glycolide) and PVP (polyvinylpyrrolidone). See Garnett, M. C. *Crit. Rev. Ther. Drug Carrier Sys.* 1999, 16, 147-207; Han, S.; Mahato, R. I.; Sung, Y. K.; Kim, S. W. *Molecular Therapy* 2000, 2, 302-317; Zauner, W.; Ogris, M.; Wagner, E. *Adv.*

Drug. Del. Rev. 1998, 30, 97-113; Kabanov, A. V.; Kabanov, V. A. Bioconj. Chem. 1995, 6, 7-20; Lynn, D. M.; Anderson, D. G.; Putman, D.; Langer, R. J. Am. Chem. Soc. 2001, 123, 8155-8156; Boussif, O.; Lezoualc'h, F.; Zanta, M. A.; Mergny, M. D.; Scherman, D.; Demeneix, B.; Behr, J. P. Proc. Natl. Acad. Sci. USA 1995, 92, 7297-7301; Choi, J. S.; Joo, D. K.; Kim, C. H.; Kim, K.; Park, J. S. J. Am. Chem. Soc. 2000, 122, 474-480; Putnam, D.; Langer, R. Macromolecules 1999, 32, 3658-3662; Gonzalez, M. F.; Ruseckaite, R. A.; Cuadrado, T. R. Journal of Applied Polymer Science 1999, 71, 1223-1230; Tang, M. X.; Redemann, C. T.; Szoka, F. C. In Vitro Gene Delivery by Degraded Polyamidoamine Dendrimers Bioconjugate Chem. 1996, 7, 703-714; Kukowska-Iatallo, J. F.; Bielinska, A. U.; Johnson, J.; Spinder, R.; Tomalia, D. A.; Baker, J. R. Proc. Nat. Acad. Sci. 1996, 93, 4897-4902; and Lim, Y.; Kim, S.; Lee, Y.; Lee, W.; Yang, T.; Lee, M.; Suh, M.; Park, J. J. Am. Chem. Soc. 2001, 123, 2460-2461.

Some representative examples of cationic polymers under investigation are described below. For example, poly(β-amino esters) have been explored and shown to condense plasmid DNA into soluble DNA/polymer particles for gene delivery. To accelerate the discovery of synthetic transfection vectors parallel synthesis and screening of a cationic polymer library was reported by Langer. Wolfert describes cationic vectors for gene therapy formed by self-assembly of DNA with synthetic block cationic co-polymers. Haensler and Szoka describe the use of cationic dendrimer polymers (polyamidoamine (PAMAM) dendrimers) for gene delivery. Wang describes a cationic polyphosphoester for gene delivery. Putnam describes a cationic polymer containing imidazole for the delivery of DNA. See Lynn, D. M.; Langer, R. J. Am. Chem. Soc. 2000, 122, 10761-10768; Wolfert, M. A.; Schacht, E. H.; Toncheva, V.; Ulbrich, K.; Nazarova, O.; Seymour, L. W. Hum. Gene Ther. 1996, 7, 2123-2133; Haensler, J.; Szoka, F. Bioconj. Chem. 1993, 4, 372; and Wang, J.; Mao, H. Q.; Leong, K W. J. Am. Chem. Soc. 2001; Putnam, D.; Gentry, C. A.; Pack, D. W.; Langer, R. Proc. Nat. Acad. Sci. 2001, 98, 1200-1205.

A number of patents are also known that describe cationic polymers for gene delivery. For example, U.S. Pat. No. 5,629,184 to Goldenberg et al. describes cationic copolymers of vinylamine and vinyl alcohol for the delivery of oligonucleotides. U.S. Pat. No. 5,714,166 to Tomalia, et al, discloses dendritic cationic-amine-terminated polymers for gene delivery. U.S. Pat. No. 5,919,442 to Yin et al. describes cationic hyper comb-branched polymer conjugates for gene delivery. U.S. Pat. No. 5,948,878 to Burgess et al. describes additional cationic polymers for nucleic acid transfection and bioactive agent delivery. U.S. Pat. No. 6,177,274 to Park et al. discloses a compound for targeted gene delivery that consists of polyethylene glycol (PEG) grafted poly(L-lysine) (PLL) and a targeting moiety, wherein at least one free amino function of the PLL is substituted with the targeting moiety, and the grafted PLL contains at least 50% unsubstituted free amino function groups. U.S. Pat. No. 6,210,717 to Choi et al. describes a biodegradable, mixed polymeric micelle used to deliver a selected nucleic acid into a targeted host cell that contains an amphiphilic polyester-polycation copolymer and an amphiphilic polyester-sugar copolymer. U.S. Pat. No. 6,267,987 to Park et al. discloses a positively charged poly[alpha-(omega-aminoalkyl) glycolic acid] for the delivery of a bioactive agent via tissue and cellular uptake. U.S. Pat. No. 6,200,956 to Scherman et al. describes a pharmaceutical composition useful for transfecting a nucleic acid containing a cationic polypeptide.

All of these polymers possess and rely on cationic moieties to bind DNA. Thus, the need exits for non-cationic polymers or macromolecules for gene delivery. Such polymers would also be advantageous over using viral vectors because the polymer delivery system would not expose the cell to a virus that could infect the cell.

The following is only a representative description of the potential therapeutic value of gene therapy. Gene therapy can be used for cancer treatment with recent papers describing its utility for prostate, colorectal, ovarian, lung, breast cancer. Gene therapy has been explored for delivery of vaccines for infectious disease, for lysosomal storage disorders, for dendritic cell-based immunotherapy, for controlling hypertension, and for rescuing ischaemic tissues. Gene therapy has also been explored for treating HIV. See Galanis, E.; Vile, R.; Russell, S. J. Crit. Rev. Oncol. Hemat 2001, 38, 177-192; Kim, D.; Martuza, R. L.; Zwiebel, J. Nature Med. 2001, 7, 783-789; Culver, K W.; Blaese, R. M. Trends Genet 1994, 10, 174-178; Harrington, K J.; Spitzweg, C.; Bateman, A. R.; Morris, J. C.; Vile, R. G. J. Urology 2001, 166, 1220-1233; Chen, M. J.; Chung-Faye, G. A.; Searle, P. F.; Young, L. S.; Kerr, D. J. Biodrugs 2001, 15, 357-367; Wen, S. F.; Mahavni, V.; Quijano, E.; Shinoda, J.; Grace, M.; Musco-Hobkinson, M. L.; Yang, T. Y.; Chen, Y. T.; Runnenbaum, I.; Horowitz, J.; Maneval, D.; Hutchins, B.; Buller, R. Cancer Gene Ther. 2003, 10, 224-238; Hoang, T.; Traynor, A. M.; Schiller, J. H. Surg. Oncol. 2002, 11, 229-241; Patterson, A.; Harris, A. L. Drugs Aging 1999, 14, 75-90; Clark, K. R.; Johnson, P. R. Curr. Op. Mol. Ther. 2001, 3, 375-384; Yew, N. S.; Cheng, S. H. Curr. Op. Mol. Ther. 2001, 3, 399-406; Jenne, L.; Schuler, G.; Steinkasserer, A. Trends Immunol 2001, 22; Sellers, K. W.; Katovich, M. J.; Gelband, C. H.; Raizada, M. K. Am. J. Med. Sci. 2001, 322, 1-6; Emanueli, C.; Madeddu, P. Brit. J. Pharmacol. 2001, 133, 951-958; and Schnell, M. J. FEMS Microbiol Lett 2001, 200,123-129.

Therefore, the need exists for new compositions and methods for gene delivery. New gene delivery compositions will find applications in medicine and gene research. The present invention fulfills this need and has other related advantages.

SUMMARY OF THE INVENTION

This present invention relates to compounds and methods for gene delivery. One aspect of the invention relates to a class of non-cationic amphiphilies for gene delivery. Another aspect of the invention relates to a cationic, amphiphilic molecule or macromolecule that transforms from a cationic entity to an anionic, neutral, or zwitterionic entity by a chemical, photochemical, or biological reaction. Another aspect of the invention relates to a method of delivering a gene to a cell using one of the molecules of the invention that transforms from a cationic entity to an anionic, neutral, or zwitterionic entity by a chemical, photochemical, or biological reaction. An additional embodiment is the formation of a hydrogel with the compositions and the use of the hydrogel for the delivery of genetic material. Another aspect of the present invention relates to a method of using the non-viral vector compositions in conjunction with a surface to mediate the delivery of nucleic acids.

DETAILED DESCRIPTION OF THE INVENTION

Figure 1:
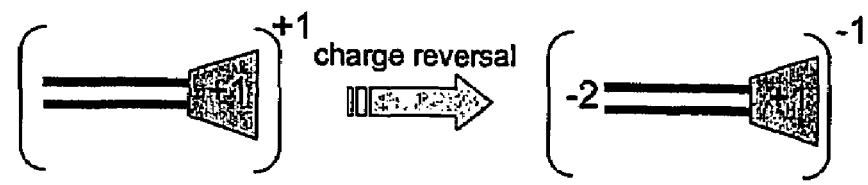
FIG. 1 depicts an illustration of an amphiphilic molecule that undergoes the charge reversal effect. The amphiphile binds DNA, since it is cationic, and then releases DNA when it is anionic.

The present invention relates to a class of molecular or macromolecular compositions for in vitro, ex vivo, and in vivo transfer of biologically active molecules, such as nucleic acids. The present invention also encompasses compositions and use of such nucleic-acid-transfection compositions. The composition contains at least one nucleic acid binding region, which is non cationic, a linker, and at least one hydrophobic region. Alternatively, the composition contains a cationic amphiphilic molecule or macromolecule that transforms from a cationic entity to an anionic, neutral, or zwitterionic entity by a chemical, photochemical, or biological reaction and its use for delivery of nucleic acids. Another embodiment of this invention is the use of these non-viral vector compositions in conjunction with a surface to mediate the delivery of nucleic acids. An additional embodiment is the formation of a hydrogel with these compositions and the use of this hydrogel for the delivery of genetic material. A further embodiment of this invention is the use of a change in ionic strength for the delivery of genetic material.

This approach entails using a chemical, photochemical, or biochemical-sensitive cationic amphiphile molecule or polymer/macromolecule for gene delivery that transforms to an anionic or neutral amphiphile or polymer intracellularly. This functional synthetic vector performs the following roles. First, it binds DNA and forms a supermolecular DNA-complex. Once this complex is in the endosome, a chemical, photochemical, or biochemical reactions affords a synthetic vector that is anionic or neutral. Finally, the anionic amphiphiles or polymers repel DNA and destabilize the supramolecular complex freeing the DNA for subsequent transcription. Furthermore, the anionic complex formed in situ disrupts the cell membrane of the endosome enabling release of the DNA from the endosome. For example, a cationic amphiphile possessing one to two terminal ethyl or benzyl ester linkages on the fatty acid is an esterase sensitive functional synthetic vector. This cationic amphiphile would bind DNA and form the supramolecular complex. An esterase would then cleave the ester linkages affording the anionic amphiphile and freeing the DNA. Another example, would be a cationic amphiphile possessing one or two ester linkages that can be cleaved by a photochemical reaction. Photocleavable protecting groups for use in this invention include nitrobenzyl, 6-bromo-7-hydroxy-coumarin-4-ylmethyl (bhc), and 8-bromo-7-hydroxyquinoline-2-ylmethyl (bhq). The release of the DNA from the amphiphile-DNA complex in vitro or in vivo is done by photolysis (one or more photon chemistry).

Delivery of the nucleic acid using a molecule or polymer described herein can be in the form of a liquid, gel, or solid. A nucleoside possessing two fatty acid chains and a phosphocholine will form a gel in aqueous solution. Such an example is synthesized and described in the examples section. Moreover, this gel can be loaded with DNA or DNA and a synthetic vector and then subsequently used to deliver nucleic acid to a specific tissue/cellular site. This mode of gene therapy is applicable to cancer.

In addition these amphiphiles or polymers can be used in conjunction with a surface (e.g., mica, glass, gold) to aid in the delivery of the DNA. For example, the surface and synthetic vector can be used to condense the DNA; once on the surface, the cell is able to uptake the DNA for subsequent transcription. A nucleoside possessing hydrophobic acyl chains and a 5000 MW polyethyelene glycol will in the presence of a surface (mica) condense DNA to form toroids. All three components of this amphiphile are generally required: the DNA base for interacting with plasmid DNA, the hydrophobic chains for bilayer or other supramolecular structure, and the PEG for aqueous solubility and condensation on the mica.

Nucleic acids suitable for delivery include, but are not limited to, DNA, RNA plasmids, siRNA, duplex oligonucleotides, single strand oligonucleotides, triplex oligonucleotides, PNAs, mRNA, etc. Delivery of nucleic acid using the novel molecule(s) or polymer(s) described in this invention includes in vitro, ex vivo, and in vivo (e.g., intravenous, aerosol, oral, topical, systemic, ocular, intraperitoneal and/or intrathecal). The administration can also be directly to a target tissue/cell or through systemic delivery. The synthetic vectors described here can be further modified to possess unique peptides, antibodies, single chain antibodies, or other small molecules that target the delivery of the DNA to a specific cell.

A further embodiment of this invention is the use of these functional synthetic vectors with known, standard, or conventional synthetic vectors (molecules and polymers) and/or cationic, anionic, zwitterionic lipids or amphiphiles (e.g., DOPE) for the delivery of DNA. Moreover the synthetic vectors described herein can be used with known peptides or polymers that lyse or destabilize cell membranes to increase the release of the DNA from the endosome (e.g., polyacrylic acids/alkyl-esters).

With respect to the molecules or amphiphiles, the present invention describes liposome compositions and a method of preparing such liposomes. Moreover, the present invention relates to the administration of the biologically active agent-liposome preparations to cells. These cells can then be used in an in vitro setting or delivered to a patient. Alternatively, the therapeutic liposome formulation is delivered to the patients. The liposome compositions of the present invention provide delivery of nucleic acids to cells. Liposome vesicles are prepared from a mixture of said amphiphile(s) described in this invention and a neutral lipid and form a bi- or multilamellar membrane structure. It is a further object of the present invention to provide a method of preparing liposomes, useful in providing efficient transfer therapy.

Antisense oligonucleotides may be designed to target specifically genes and consequently inhibit their expression. In addition, this delivery system may be a suitable carrier for other gene-targeting oligonucleotides, such as ribozymes, triple-helix-forming oligonucleotides or oligonucleotides exhibiting non-sequence specific binding to a particular protein or other intracellular molecules. For example, the genes of interest may include retroviral or viral genes, drug-resistance genes, oncogenes, genes involved in the inflammatory response, cellular adhesion genes, hormone genes, abnormally overexpressed genes involved in gene regulation.

Below the present invention is described by reference to specific embodiments. This description is not meant to limit the scope of the invention, but to convey the essence of the invention. Additional embodiments may be readily envisioned by one of ordinary skill in the art, and such embodiments fall within the scope of the invention.

Figure 2:
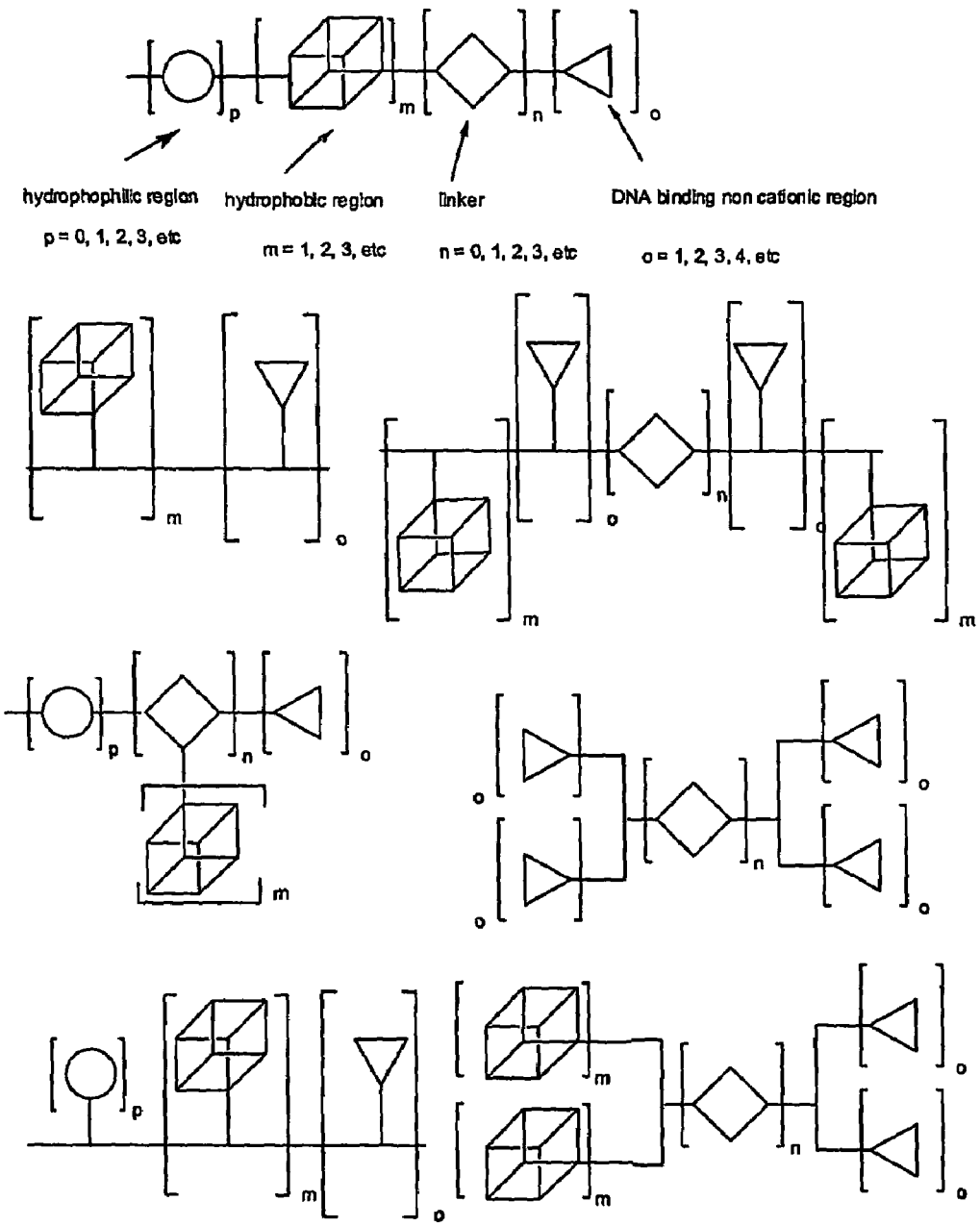
FIG. 2 depicts a molecule or macromolecule of the invention.

One aspect of the present invention relates to a molecule or macromolecule shown in FIG. 2 that contains at least one DNA binding non-cationic region, zero or more linker regions, and at least one hydrophobic region, zero or more hydrophilic regions linked together by covalent bonds used for the in vitro, ex vivo, or in vivo delivery of nucleic acid.

Figure 3:
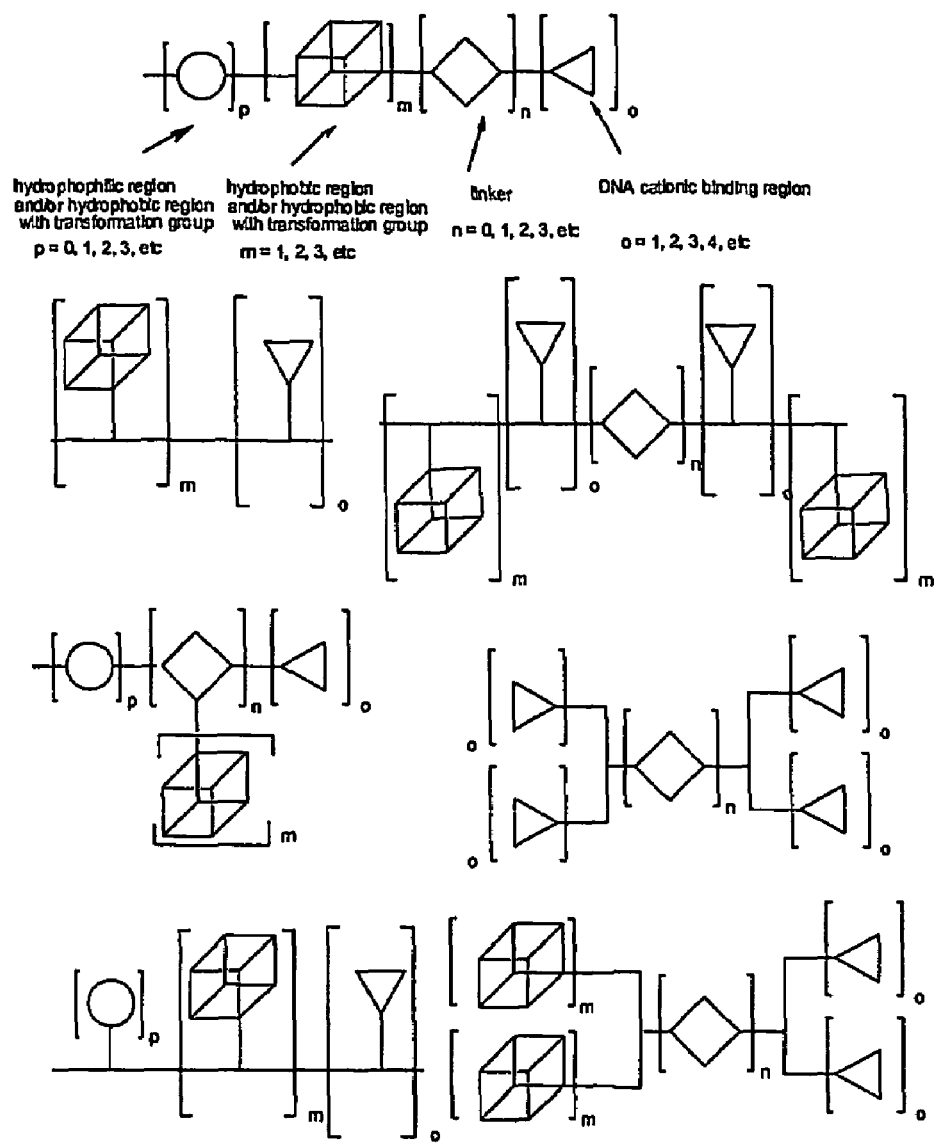
FIG. 3 depicts a molecule or macromolecule of the invention.

Another aspect of the present invention relates to a molecule or macromolecule shown in FIG. 3 that contains at least one DNA binding cationic region, zero or more linker regions, and at least one hydrophobic region, zero or more hydrophilic linked together by covalent bonds used for the in vitro, ex vivo, or in vivo delivery of nucleic acid. Whereupon the cationic molecule or macromolecule is transformed from a cationic entity to a neutral, anionic, or zwitterionic by a chemical, photochemical, or biological (e.g., enzymatic) reaction.

Another aspect of the present invention relates to a molecule or macromolecule shown in FIG. 3 that contains at least one polyethylene glycol (i.e., polyethylene oxide, ethylene glycol) unit, zero or more linker regions, zero or more hydrophobic regions, zero or more hydrophilic, zero or more neutral, anionic, cationic, or zwitterionic regions linked together by covalent bonds used for the in vitro, ex vivo, or in vivo delivery of nucleic acid.

In certain instances, the aforementioned macromolecule is linear, comb, star, dendritic, or hyperbranched.

In certain instances, the aforementioned macromolecule is a homopolymer or heteropolymer (e.g., di-block, multi-block, random co-polymer).

In certain instances, the invention relates to the aforementioned molecule or macromolecule, wherein the hydrophobic region is one or more cholesterol or other natural steriod or modified steriod, or synthetic analog.

In certain instances, the invention relates to the aforementioned molecule or macromolecule that employs a photochemical reaction whereby the reaction is a single or multi-photon reaction for the delivery of nucleic acids.

In certain instances, the invention relates to the aforementioned molecule or macromolecule that can undergo an enzymatic reaction for the delivery of nucleic acids.

In certain instances, the invention relates to the aforementioned molecule or macromolecule that employs a enzymatic reaction whereby the enzyme is an esterase for the delivery of nucleic acids.

In certain instances, the invention relates to the aforementioned molecule or macromolecule that employs a temperature change for the delivery of nucleic acids.

In certain instances, the invention relates to the aforementioned molecule or macromolecule that employs a change in ionic strength for the delivery of nucleic acids.

In certain instances, the invention relates to the aforementioned molecule or macromolecule that employs a surface for the delivery of nucleic acids.

In certain instances, the invention relates to the aforementioned molecule or macromolecule that also employs a change in pH for the delivery of nucleic acids.

In certain instances, the invention relates to the aforementioned molecule or macromolecule that contains a targeting moiety for a cell or tissue.

In certain instances, the invention relates to the aforementioned molecule or macromolecule that contains a natural or charged peptide or synthetic polymer that destabilizes cell membranes.

In certain instances, the invention relates to the aforementioned molecule or macromolecule wherein the macromolecule/polymer is polyethylene oxide or polyethylene glycol for the delivery of nucleic acids.

In certain instances, the invention relates to the aforementioned molecule or macromolecule that contains a linker that is neutral, cationic, anionic, and/or zwitterionic.

In certain instances, the invention relates to the aforementioned molecule or macromolecule that contains a hydrophilic unit that is hydrophilic polymer (e.g., polyethylene glycol, polyacrylic acids, polyvinyl alcohol) or small molecule (e.g., tetraethylene glycol, sugar, succinic acid, glycine, glycerol, spermine).

In certain instances, the invention relates to the aforementioned molecule or macromolecule that forms a gel or crosslinked network in aqueous or non-aqueous solution and the gel/crosslinked network is subsequently used for the delivery of nucleic acids.

Another aspect of the invention relates to a gel/crosslinked network used for the delivery of nucleic acids formed by a photochemical reaction, enzymatic reaction, an oxidation reaction, a chemical reaction, a pH change, a temperature change, an ionic strength change, a non-covalent interaction(s) with another polymer(s) or molecule(s), or a change in molecule(s) or macromolecule(s) concentration.

Figure 4:
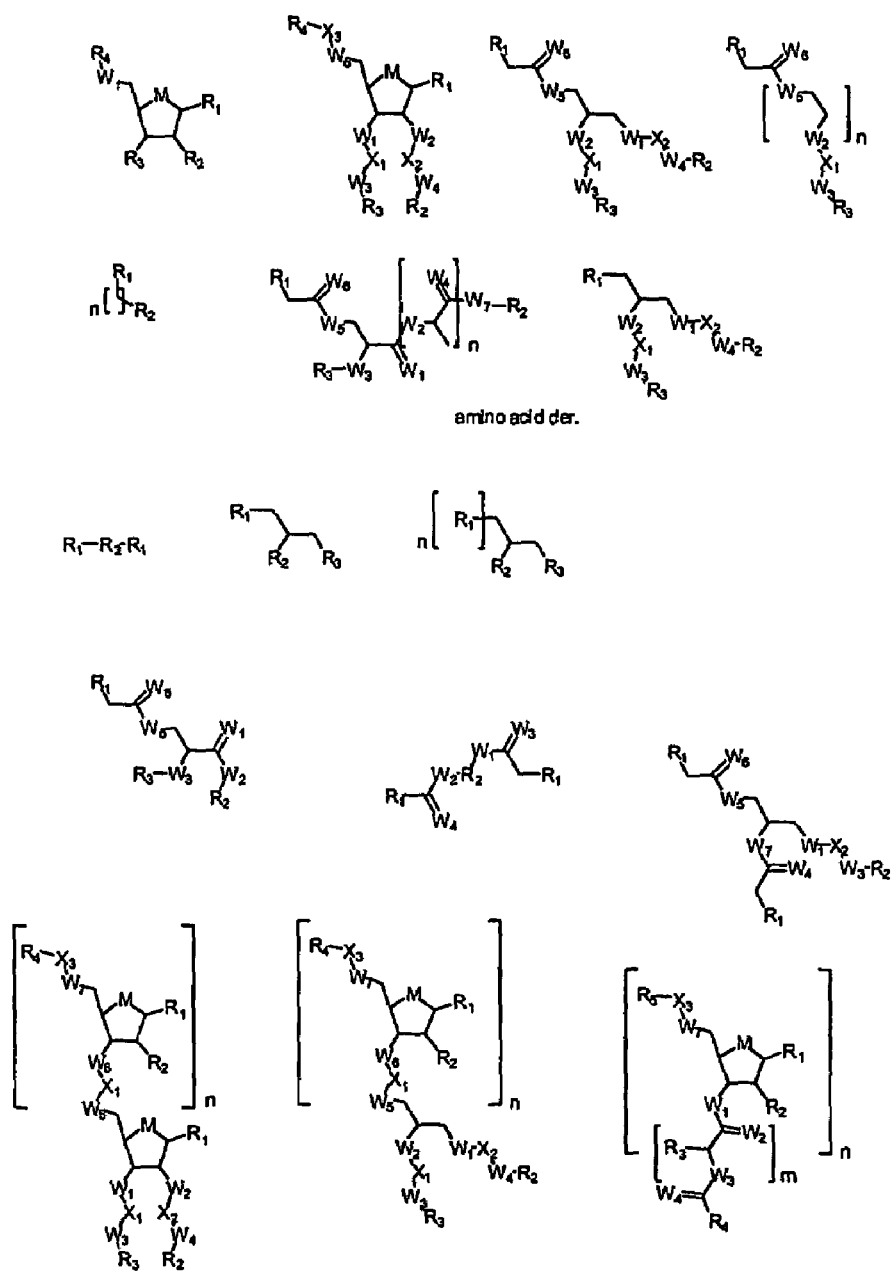
FIG. 4 depicts certain molecules or macromolecules of the invention.
Figure 5:
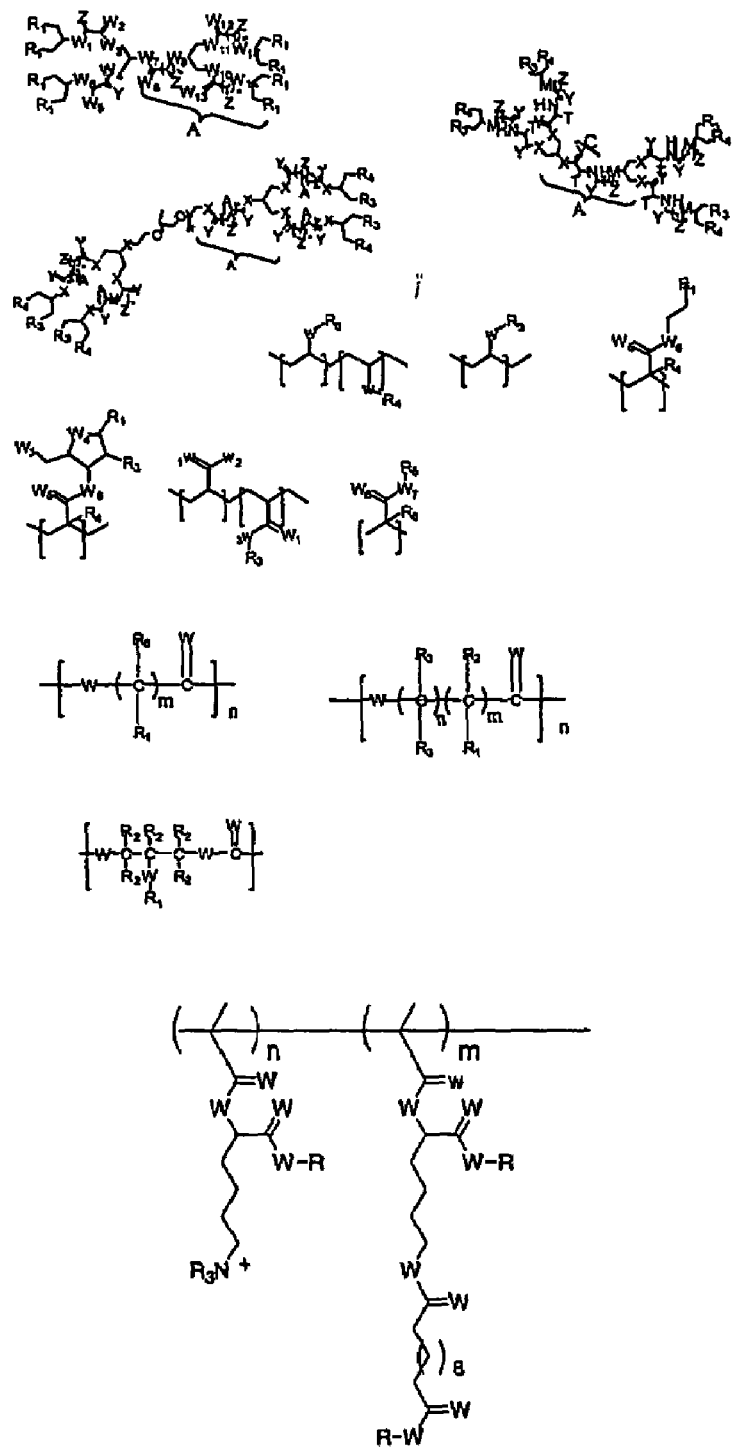
FIG. 5 depicts certain molecules or macromolecules of the invention.

Another aspect of the invention relates to a molecule(s) or macromolecule(s) as shown in FIGS. 4 and 5.

In certain instances, the invention relates to the aforementioned macromolecule wherein the macromolecule is a homopolymer, random copolymer, or block copolymer.

In certain instances, the invention relates to the aforementioned macromolecule wherein $R^1$ is at least one non-cationic DNA binding moiety such as a nucleoside, nucleobase, aromatic compound, polyaromatic compound, aliphatic compound, carbohydrate, amino acid, peptide, PNA, or pseudo peptide In certain instances, the invention relates to the aforementioned macromolecule wherein $R^1$ is one or more of the same or different non-cationic DNA binding moiety such as a nucleoside, nucleobase, aromatic compound, polyaromatic compound, aliphatic compound, carbohydrate, amino acid, or peptide.

In certain instances, the invention relates to the aforementioned macromolecule wherein $R^1$ is one or more of the same or different cationic DNA binding moiety such as a primary amine, secondary amine, tertiary amine, quaternary amine (e.g, choline), or molecule(s) possessing more than one cationic amine (e.g., lys, spermine).

In certain instances, the invention relates to the aforementioned macromolecule wherein one or more of $R^1$, $R^2$, $R^3$, $R^4$, and $R^5$ contains a functionality that upon a chemical, photochemical, or biological reaction transform the molecule(s) or macromolecule(s) to a neutral, anionic, or zwitterionic molecule or macromolecule.

In certain instances, the invention relates to the aforementioned macromolecule wherein one or more of $R^1$, $R^2$, $R^3$, $R^4$, and $R^5$ contains a functionality such as an ester that upon a biological reaction transform the molecule(s) or macromolecule(s) to a neutral, anionic, or multi-anionic molecule or macromolecule.

In certain instances, the invention relates to the aforementioned macromolecule wherein one or more of $R^1$, $R^2$, $R^3$, $R^4$, and $R^5$ contains a functionality such as an photocleavable ester that upon a photochemical reaction transform the molecule(s) or macromolecule(s) to a neutral, anionic, or multi-anionic molecule or macromolecule, wherein the functionality is not limited to a nitrobenzyl ester or a BHC ester.

In certain instances, the invention relates to the aforementioned macromolecule wherein $R^2$, $R^3$, $R^4$, and $R^5$ are a straight or branched chain ester of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain ester of 2-50 carbon atoms wherein the chain is fully saturated, fully unsaturated or any combination therein and wherein one or more of $R^2$, $R^3$, $R^4$, and $R^5$ is a —H, —OH, methoxy, amine, thiol, or any combination therein.

In certain instances, the invention relates to the aforementioned macromolecule wherein $R^2$, $R^3$, $R^4$, and $R^5$ are a straight or branched chain ether of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain ether of 2-50 carbon atoms wherein the chain is fully saturated, fully unsaturated or any combination therein and wherein one or more of $R^2$, $R^3$, $R^4$, and $R^5$ is a —H, —OH, methoxy, amine, thiol, or any combination therein.

In certain instances, the invention relates to the aforementioned macromolecule wherein $R^2$, $R^3$, $R^4$, and $R^5$ are a straight or branched chain silane of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain silane of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain amide of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain amide of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain urea of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain urea of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain urethane of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain urethane of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain carbonate of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain carbonate of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain sulfate of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain sulfate of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain thio-urethane of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain thio-urethane of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain amine of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain amine of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain phosphate of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain phosphate of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain thiophosphate of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain thiophosphate of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain boranophosphate of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain acetal of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain acetal of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain boranophosphate of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain thio-urea of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain thio-urea of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain thio-ether of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain thio-ether of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain thio-ester of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain thio-ester of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein $R^2$, $R^3$, $R^4$, and $R^5$ are a straight or branched chain of 2-50 carbon atoms wherein the chain is fully saturated, fully unsaturated or any combination therein.

In certain instances, the invention relates to the aforementioned macromolecule wherein one or more of $R^2$, $R^3$, $R^4$, and $R^5$ is the same or different straight or branched chain of 2-50 carbon atoms wherein the chain is fully saturated, fully unsaturated or any combination therein and wherein one or more of $R^2$, $R^3$, $R^4$, and $R^5$ is a —H, —OH, amine, thiol, methoxy or any combination therein.

In certain instances, the invention relates to the aforementioned macromolecule wherein chains are hydrocarbons, fluorocarbons, halocarbons, alkenes, or alkynes or any combination of 1 or more.

In certain instances, the invention relates to the aforementioned macromolecule wherein one or more of $R^2$, $R^3$, $R^4$, and $R^5$ chains are polypeptide(s) or contain at least one amino acid(s) wherein one or more $R^2$, $R^3$, $R^4$, and $R^5$ is a chain as described above.

In certain instances, the invention relates to the aforementioned macromolecule wherein one or more of the chains contains a disulfide bond or linkage.

In certain instances, the invention relates to the aforementioned macromolecule wherein one or more of the chains contains a linkage suitable to cleavage by pH, light, or enzyme.

In certain instances, the invention relates to the aforementioned macromolecule wherein chains are amino acid(s) or polypeptide(s) combined with one or more of a hydrocarbons, fluorocarbons, halocarbons, alkenes, or alkynes chain or any combination thereof.

In certain instances, the invention relates to the aforementioned macromolecule wherein said chains are polyethylene glycol (PEG), polyethylene oxide, polyester [(poly(L-lactic acid), poly(D-lactic acid), poly(D-,L-lactic acid), poly(glycolic acid), poly(L-lactic-co-glycolic acid), poly(D-lactic-co-glycolic acid), poly(.epsilon.-caprolactone), polybutyrolactone], polyamine (PMMA), polyacrylic acid, polyamino acid [poly(L-serine ester), poly(D-serine ester), poly(L-lysine), poly(D-lysine), polyornithine, and polyarginine], polynucleic acid and polysaccharides of molecular weight ranging from 100-1,000,000.

In certain instances, the invention relates to the aforementioned macromolecule wherein 1 chain or more of the chains contains one or more ionic, photo, covalent crosslinkable group.

In certain instances, the invention relates to the aforementioned macromolecule wherein straight or branched chains are the same number of carbons or different wherein one or more of $R^2$, $R^3$, $R^4$, and $R^5$ is any combination of the linkers including ester, silane, urea, amide, amine, carbamate, urethane, thio-urethane, carbonate, thio-ether, thio-ester, sulfate, sulfoxide, nitroxide, phosphate and ether.

In certain instances, the invention relates to the aforementioned molecule or macromolecule wherein at the terminus/i of the chain(s), there exists any group(s) such as any amine, thiol, amide, carboxylic acid, phosphate, sulphate, hydroxide, or —SeH.

In certain instances, the invention relates to the aforementioned molecule or macromolecule wherein at the terminus/i of the chain(s), there exists any group that can be subsequently transformed from a neutral species to an anionic or zwitterionic group with the formation of a neutral, anionic, or zwitterionic molecule(s) or macromolecule (s).

In certain instances, the invention relates to the aforementioned molecule or macromolecule wherein at the terminus/i of the chain(s), there exists a carboxylic acid or phosphate group that is protected with a group that can be liberated by a chemical, biological, or photochemical group.

In certain instances, the invention relates to the aforementioned molecule or macromolecule wherein at the terminus/i of the chain(s), there exists one or more ser, tyr, or thr with zero or more amino acids (including a peptide) that undergoes a biological reaction such as a phosphorylation.

In certain instances, the invention relates to the aforementioned molecule or macromolecule wherein the preferred chain length is between 6-24.

In certain instances, the invention relates to the aforementioned molecule or macromolecule wherein M is O, S, N—H, N—R, wherin R is —H, $CH_2$, $CR_2$ or a chain as defined above, Se or any isoelectronic species of oxygen.

In certain instances, the invention relates to the aforementioned molecule or macromolecule wherein the cyclic structure is of 4 or more atoms or bicyclic.

In certain instances, the invention relates to the aforementioned molecule or macromolecule wherein W is O, S, N—H, N—R, wherin R is —H, $CH_2$, $CR_2$ or a chain as defined above, Se or any isoelectronic species of oxygen and with or without XYZ or in any combination therof.

In certain instances, the invention relates to the aforementioned molecule or macromolecule wherein W is a phosphonate, phosphate, boronophosphate, and or thiophosphate, selenophosphate.

In certain instances, the invention relates to the aforementioned molecule or macromolecule wherein X is a phosphonate, phosphate, boronophosphate, thiophosphate, and or selenophosphate.

In certain instances, the invention relates to the aforementioned molecule or macromolecule wherein one or more of $R^2$, $R^3$, $R^4$, and $R^5$ is a hydroxide, N-succinyl derivative, amino acid, carbohydrate, nucleic acid, multiple amines, multiple hydroxides, cyclic amine, polyamine, polyether, polyester or tertiary, secondary and primary amines with or without chains of 1-20 carbons.

In certain instances, the invention relates to the aforementioned molecule or macromolecule wherein an antibody or single chain antibody is attached to a chain as described above.

In certain instances, the invention relates to the aforementioned molecule or macromolecule wherein a nucleotide is attached to a chain as described above.

In certain instances, the invention relates to the aforementioned molecule or macromolecule wherein a nucleoside is attached to a chain as described above.

In certain instances, the invention relates to the aforementioned molecule or macromolecule wherein an oligonucleotide is attached to a chain as described above.

In certain instances, the invention relates to the aforementioned molecule or macromolecule wherein a contrast agent is attached to a chain as described above.

In certain instances, the invention relates to the aforementioned molecule or macromolecule wherein a ligand is attached to a chain as described above that binds to a biological receptor.

In certain instances, the invention relates to the aforementioned molecule or macromolecule wherein a pharmaceutical agent is attached to a chain as described above.

In certain instances, the invention relates to the aforementioned molecule or macromolecule wherein a carbohydrate is attached to a chain as described above.

In certain instances, the invention relates to the aforementioned molecule or macromolecule wherein a contrast agent is a PET or MRI agent such as Gd(DPTA).

In certain instances, the invention relates to the aforementioned molecule or macromolecule wherein iodated compounds are attached for X-ray imaging.

In certain instances, the invention relates to the aforementioned molecule or macromolecule wherein a carbohydrate is lactose, galactose, glucose, mannose, sialic acid fucose, fructose, manose, sucrose, cellobiose, nytrose, triose, dextrose, trehalose, maltose, galactosamine, glucosamine, galacturonic acid, glucuronic acid, gluconic acid, or lactobionic acid.

In certain instances, the invention relates to the aforementioned molecule or macromolecule wherein a stereochemical center(s) in the composition according to claim 1, 2, or 3 affords chiral and achiral compounds.

In certain instances, the invention relates to the aforementioned molecule or macromolecule wherein any of the above compositions are attached together to form compounds similar to geminal lipids.

In certain instances, the invention relates to the aforementioned molecule or macromolecule wherein any of the above compositions have both of their chain groups attached in a cyclical fashion to another lipid of any composition such as in a bolalipid.

Another aspect of the present invention relates to a composition comprising one of the aforementioned compounds mixed from 0.1-99.9% with a known cationic, anionic or zwitterionic molecule or macromolecule, such as DOPE, DLPC, DMPC, DPPC, DSPC, DOPC, DMPE, DOPE, DPPE, DMPA-Na, DMRPC, DLRPC, DARPC, or similar catonic, anionic, or zwitterionic amphiphiles.

In certain instances, the invention relates to the aforementioned macromolecule that forms a supramolecular structure such as a liposome (multilamellar, single lamellar, giant), helix, disc, tube, fiber, torus, hexagonal phase, micelle, gel phase, reverse micelle, microemulsion or emulsion.

In certain instances, the invention relates to the aforementioned composition that forms a microemulsion, nanoemulsion, or emulsion.

Another aspect of the present invention relates to a supramolecular structure(s) formed from a combination of one of the aforementioned compounds with from 0.1-99.9% of known materials such as DPPC, DMPC, PEGylated DPPC, DOPE, DLPC, DMPC, DPPC, DSPC, DOPC, DMPE, DOPE, DPPE, DMPA-Na, DMRPC, DLRPC, DARPC, or similar catonic, anionic, or zwitterionic amphiphiles fatty acids, cholesterol, flourescently labeled phospholipids, ether lipids, sphingolipids, and other such compositions to those known in the art.

In certain instances, the invention relates to the aforementioned macromolecule that is used in presence of a surface to mediated the delivery of nucleic acids. Wherein the surface is glass, mica, polymer, metal, metal alloy, ceramic, oxide, etc.

Another aspect of the present invention relates to the aforementioned composition or a resulting supramolecular structure in an aqueous solution, wherein the said aqueous solution is selected from water, buffered aqueous media, saline, buffered saline, solutions of amino acids, solutions of sugars, solutions of vitamins, solutions of carbohydrates or combinations of any two or more thereof.

Another aspect of the present invention relates to the aforementioned composition or a resulting supramolecular structure in aqueous/nonaqeuous solution wherein the said aqueous solution is selected from water, buffered aqueous media, saline, buffered saline, solutions of amino acids, solutions of sugars, solutions of vitamins, solutions of carbohydrates or combinations of any two or more thereof and non aqueous solution is selected from DMSO, ethanol, methanol, THF, dichloromethane, DMF, etc combinations of any two or more thereof.

Another aspect of the present invention relates to the aforementioned composition or a resulting supramolecular structure as a particle, foam, gel, or supramolecular assembly. Wherein a method for preparation of one of these supramolecular structures, a liposome, is to form a film of the lipid on a glass coverslip and then incubate it in a sucrose solution for 12 hours, deposit a thin film of lipid on the inside of a round bottom flask and then rehydrate at a temperature above its phase transition temperature, or sonicate hydrated lipids in order to form supramolecular structures. Wherein a extrusion, sonication or vortexing method is used to form supramolecular structures in the presence or absence of nucleic acids. Wherein any of the above compositions are modified in order to destabilize in acidic, basic, or neutral environments. Wherein any of the above compositions are modified in order to destabilize in cold, warm, or ultrasonic environments.

Another aspect of the present invention relates to any one of the aforementioned compositions or supramolecular structures for delivery of nucleic acids.

Another aspect of the present invention relates to any one of the aforementioned compositions and a cationic molecule or macromolecule for the delivery of nucleic acids.

Another aspect of the present invention relates to a method using any one of the aforementioned compositions for nucleic acid delivery and transfection.

Another aspect of the present invention relates to a method using any one of the aforementioned supramolecular structure for nucleic acid delivery and transfection.

Another aspect of the present invention relates to the aforementioned method for nucleic acid delivery and transfection in combination with from 0.1-99.9% of known materials such as DPPC, DMPC, PEGylated DPPC, DPPC, DOPE, DLPC, DMPC, DPPC, DSPC, DOPC, DMPE, DOPE, DPPE, DMPA-Na, DMRPC, DLRPC, DARPC, or similar catonic, anionic, or zwitterionic amphiphiles, fatty acids, cholesterol, flourescencetly labeled phospholipids, lipids, sphingolipids, and other such compositions to those known in the art.

In certain instances, the invention relates to the aforementioned composition with said nucleic acid wherein the nucleic acid comprise a DNA sequence encoding a genetic marker selected from the group consisting of luciferase gene, beta-galactosidase gene, hygromycin resistance, neomycin resistance, and chloramphenicol acetyl transferase.

In certain instances, the invention relates to the aforementioned composition with said nucleic acid wherein the nucleic acid comprise a DNA sequence encoding protein selected from the group consisting of low density lipoprotein receptors, coagulation factors, gene suppressors of tumors, major histocompatibility proteins, antioncogenes, p16, p53, thymidine kinase, IL2, IL 4, and TNFa.

In certain instances, the invention relates to the aforementioned composition with said nucleic acid wherein the nucleic acid comprise a DNA sequence encoding viral antigen.

In certain instances, the invention relates to the aforementioned composition with said nucleic acid wherein the nucleic acid comprise a DNA sequence encoding an RNA selected from the group consisting of a sense RNA, an antisense RNA, and a ribozyme.

In certain instances, the invention relates to the aforementioned composition with said nucleic acid wherein the nucleic acid comprise a DNA sequence encoding lectin, a mannose receptor, a sialoadhesin, or a retroviral transactivating factor.

In certain instances, the invention relates to the aforementioned composition with said nucleic acid wherein the nucleic acid comprise a DNA or RNA sequence of medical interest or relevance.

Another aspect of the invention relates to a method of transfecting cells in vitro, ex vivo, or in vivo comprising contacting said cells with any one of the aforementioned compositions under conditions wherein said composition enters said cells, and the nucleic acid of said composition is released.

Another aspect of the invention relates to a method of transfecting cells in vitro, ex vivo, or in vitro bearing a receptor recognizing a targeting moiety comprising contacting said cells with the composition comprising one of the aforementioned compounds and a nucleic acid, under conditions wherein said composition enters said cells, and the nucleic acid of said composition is released.

Another aspect of the invention relates to a method of transfecting cells in vitro, ex vivo, or in vitro where the cells are human including embryonic and stem cells, animal, plant, insect, immortal, or genetically engineered.

Another aspect of the invention relates to the use of transfected cells for treating a disease or repairing an injured tissue, organ, or bone.

Another aspect of the invention relates to the use of said composition for treating a disease or repairing an injured tissue, organ, or bone.

Another aspect of the invention relates to the use of said composition for cancer treatment.

Another aspect of the invention relates to the use of said composition for correcting or treating a genetic defect.

Another aspect of the invention relates to the use of said composition for a medical application.

Another aspect of the invention relates to the use of said composition for agricultural use, experiments, crop management or food manufacturing.

Compounds of the Invention

One aspect of the present invention relates to a compound represented by formulas I:

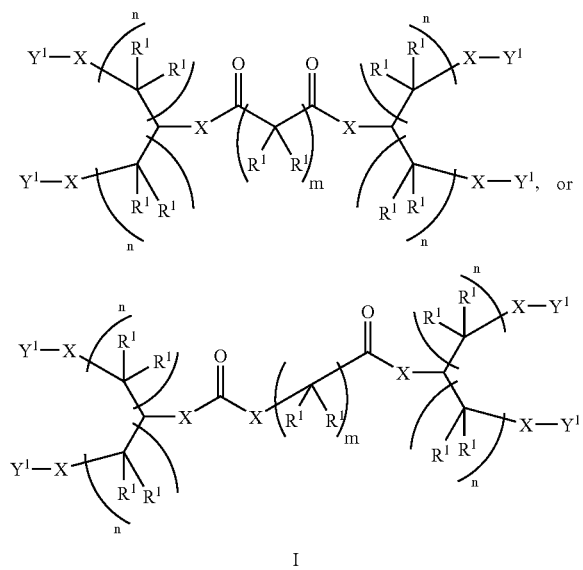

I wherein

X represents independently for each occurrence O or —N(R²)—;

Y¹ represents independently for each occurrence —C(O)R³, —C(O)N(R²)R³, alkyl, alkenylalkyl, aryl, aralkyl, R⁴, or

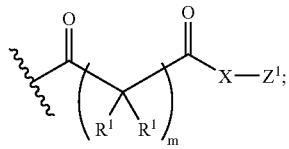

Z¹ represents independently for each occurrence —(C(R²)₂)$_P$—N(R⁵)₃.A, R⁴, or

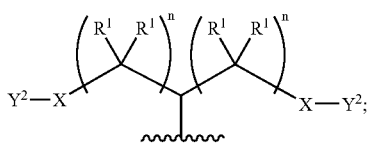

Y² represents independently for each occurrence —C(O)R³, —C(O)N(R²)R³, alkyl, alkenylalkyl, aryl, aralkyl, R⁶, or

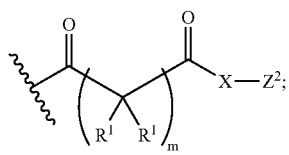

Z² represents independently for each occurrence R⁶, —(C(R⁸)₂)$_P$—N(R⁹)₃.A, or

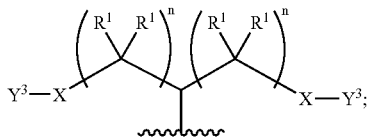

Y³ represents independently for each occurrence —C(O)R³, —C(O)N(R²)R³, alkyl, alkenylalkyl, aryl, aralkyl, R⁷, or

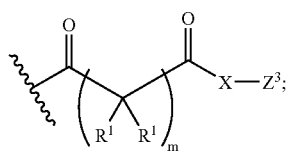

Z³ represents independently for each occurrence R⁷, —(C(R²)₂)$_P$—N(R⁵)₃.A, or

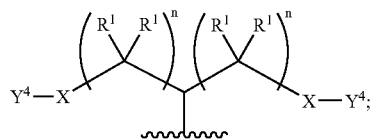

Y⁴ represents independently for each occurrence —C(O)R³, —C(O)NR²)R³, alkyl, alkenylalkyl, aryl, aralkyl, R⁸, or

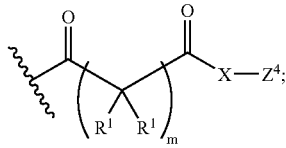

Z⁴ represents independently for each occurrence R⁸ or —C(R²)₂)$_P$—N(R⁵)₃.A;

R¹ represents independently for each occurrence H, alkyl, or halogen;

R² represents independently for each occurrence H, alkyl, aryl, or aralkyl;

R³ represents independently for each occurrence alkyl, alkenylalkyl, aryl, or aralkyl;

R⁴, R⁶, R⁷, and R⁸ are H;

R⁵ represents independently for each occurrence H, alkyl, aryl, or aralkyl;

n, m, and p each represent independently for each occurrence 1, 2, 3, 4, 5, 6, 7, 8, 9, or 10;

A is an anion with a net charge of negative one; and provided that R⁴ only occurs once, R⁶ only occurs once, R⁷ only occurs once, and R⁸ only occurs once.

In certain embodiments, the present invention relates to the aforementioned compound, wherein X is O.

In certain embodiments, the present invention relates to the aforementioned compound, wherein R¹ and R² are H, R⁵ is alkyl, m is 2, and n is 1.

In certain embodiments, the present invention relates to the aforementioned compound, wherein Y¹ is —C(O)R³ or

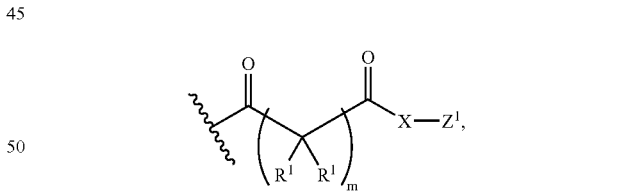

and Z¹ is —C(R²)₂)$_P$—N(R⁵)₃.A.

In certain embodiments, the present invention relates to the aforementioned compound, wherein Y¹ is —C(O)R³ or

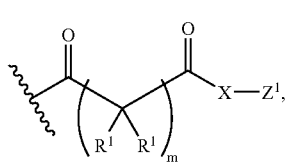

Z¹ is —(C(R²)₂)$_P$—N(R²)₃.A, and R³ is alkyl.

In certain embodiments, the present invention relates to the aforementioned compound, wherein $Y^1$ is

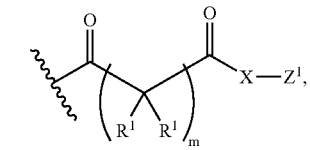

$Z^1$ is $-(C(R^2)_2)_P-N(R^5)_3.A$ or

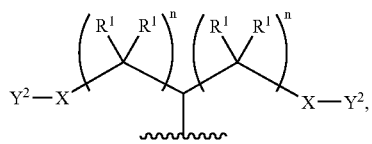

$Y^2$ is $-C(O)R^3$, and $R^3$ is alkyl.

In certain embodiments, the present invention relates to the aforementioned compound, wherein X is O, $R^1$ and $R^2$ are H, $R^5$ is alkyl, m is 2, n is 1, $Y^1$ is

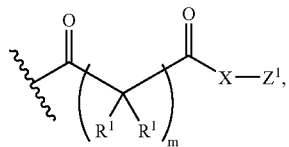

$Z^1$ is $-(C(R^2)_2)_P-N(R^5)_3.A$ or

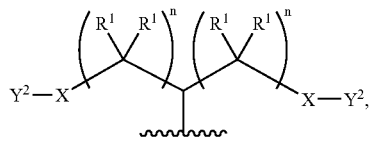

$Y^2$ is $-C(O)R^3$, and $R^3$ is alkyl.

In certain embodiments, the present invention relates to the aforementioned compound, wherein $Y^1$ is

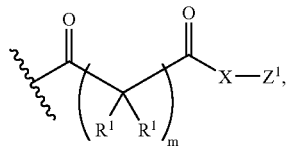

$Z^1$ is

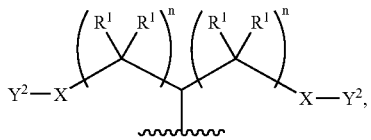

$Y^2$ is $-C(O)R^3$ or

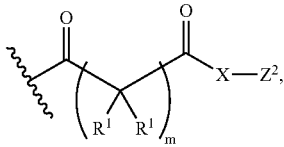

$Z^2$ is $-(C(R^2)_2)_P-N(R^5)_3.A$, and $R^3$ is alkyl.

In certain embodiments, the present invention relates to the aforementioned compound, wherein X is O, $R^1$ and $R^2$ are H, $R^5$ is alkyl, m is 2, n is 1, $Y^1$ is

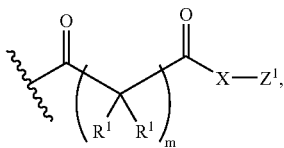

$Z^1$ is

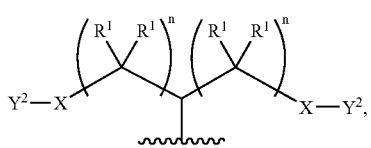

$Y^2$ is $-C(O)R^3$ or

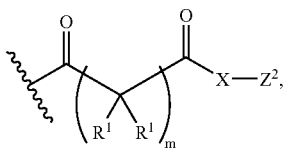

$Z^2$ is $-(C(R^2)_2)_P-(R^5)_3.A$, and $R^3$ is alkyl.

In certain embodiments, the present invention relates to the aforementioned compound, wherein $Y^1$ is

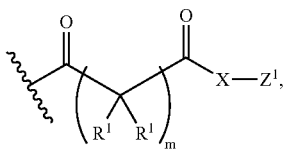

$Z^1$ is

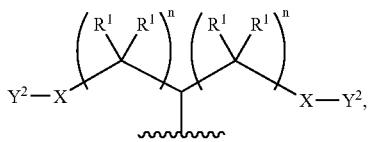

$Y^2$ is

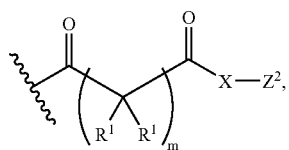

$Z^2$ is $-(C(R^2)_2)_P-N(R^5)_3.A$, and $R^3$ is alkyl.

In certain embodiments, the present invention relates to the aforementioned compound, wherein X is O, $R^1$ and $R^2$ are H, $R^5$ is alkyl, m is 2, n is 1, $Y^1$ is

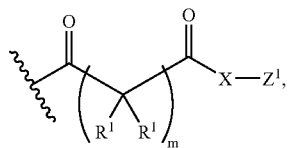

$Z^1$ is

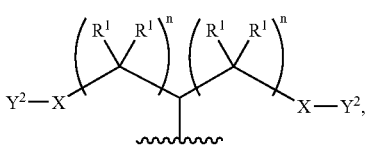

$Y^2$ is

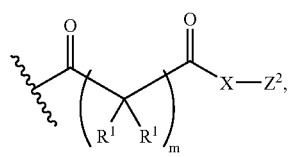

$Z^2$ is $-(C(R^2)_2)_P-N(R^5)_3.A$, and $R^3$ is alkyl.

In certain embodiments, the present invention relates to the aforementioned compound, wherein A is halogen or $R_{25}CO_2^-$, wherein $R_{25}$ is alkyl, aryl, or aralkyl.

In certain embodiments, the present invention relates to the aforementioned compound, wherein A is halogen.

In certain embodiments, the present invention relates to the aforementioned compound, wherein said compound of formula I is

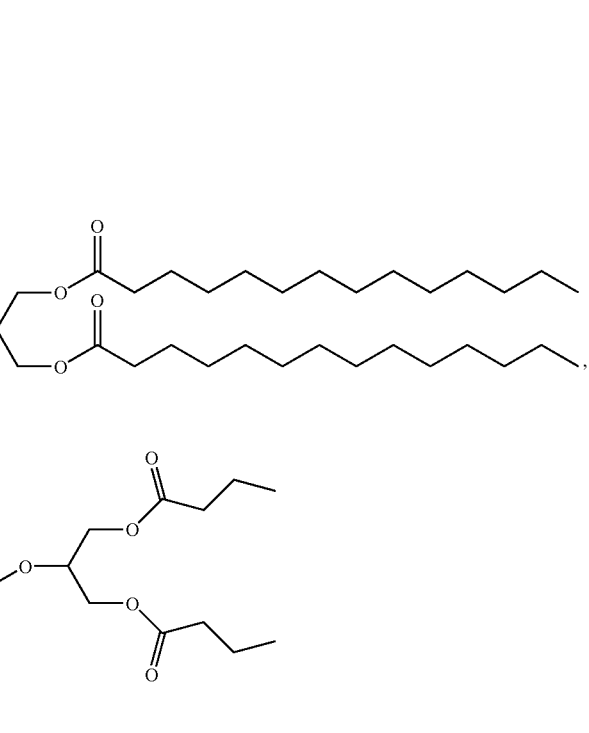

-continued
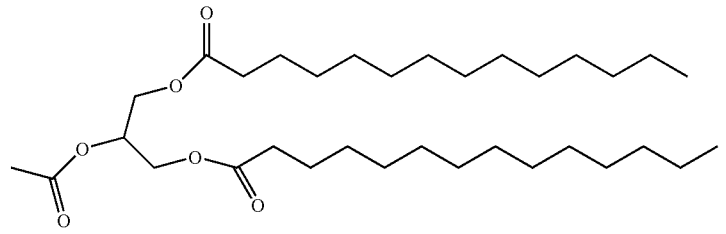
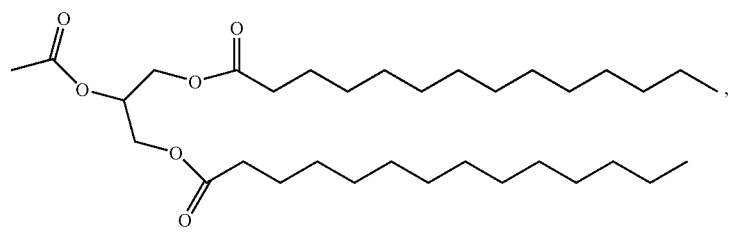
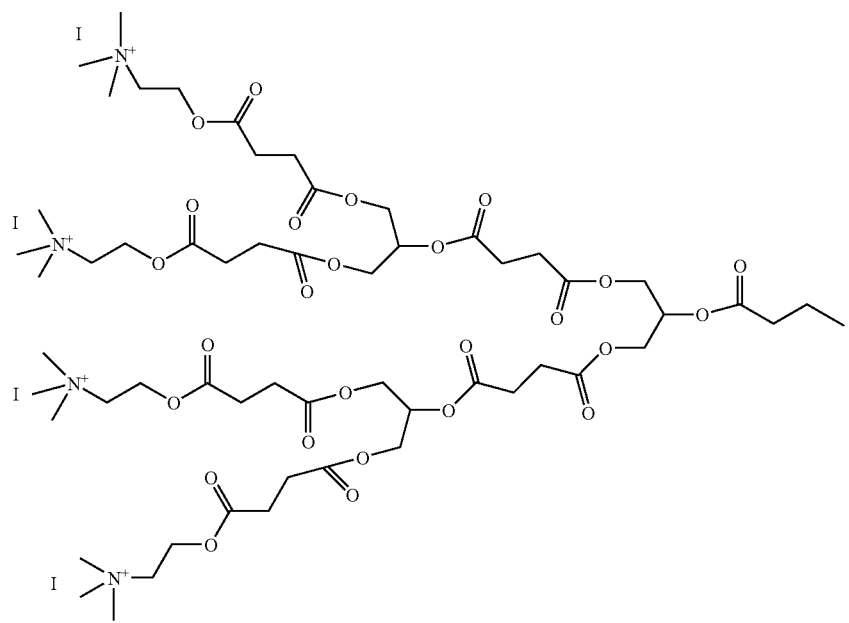
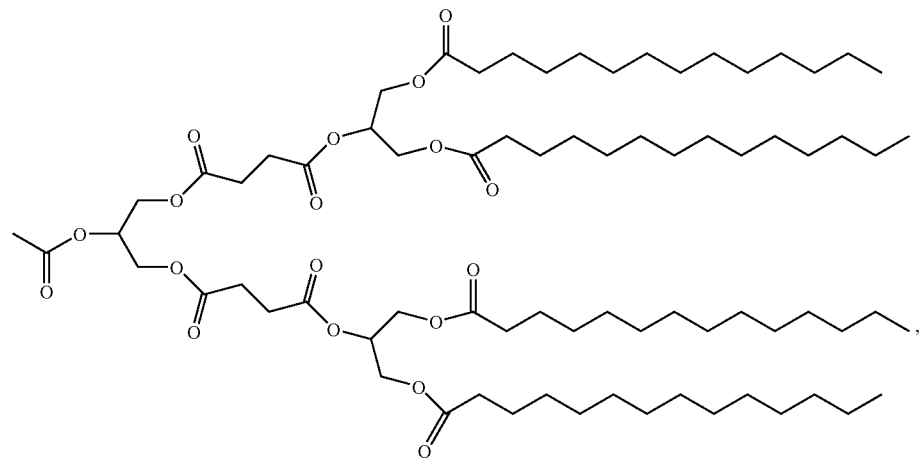

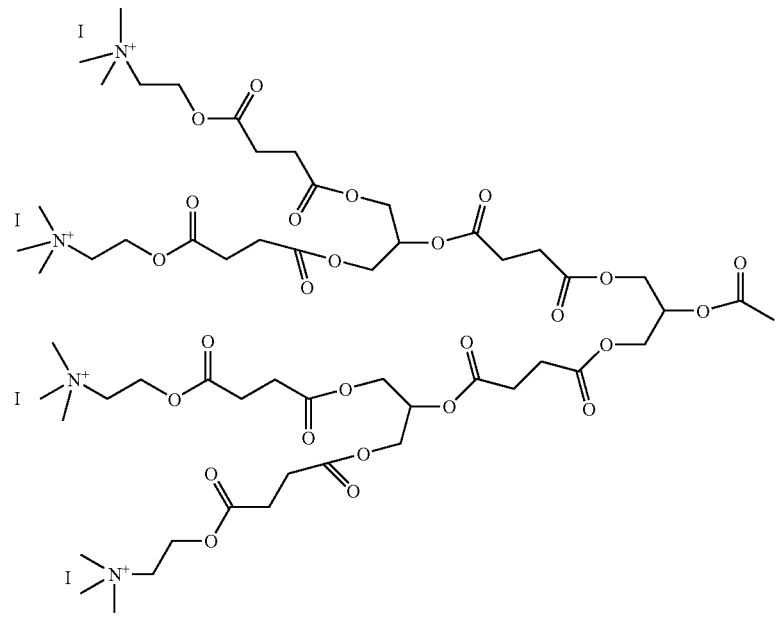
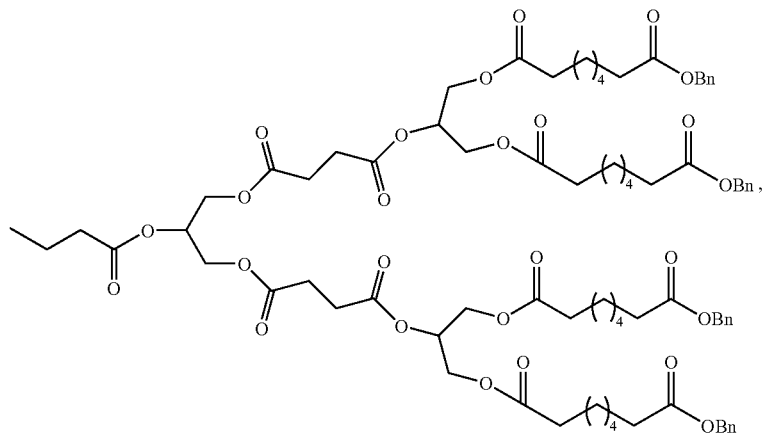
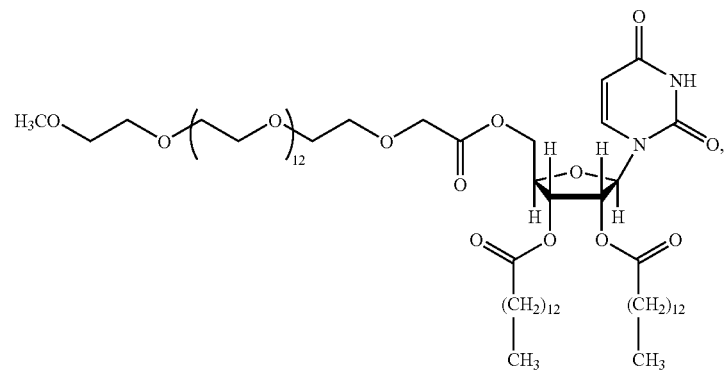

-continued
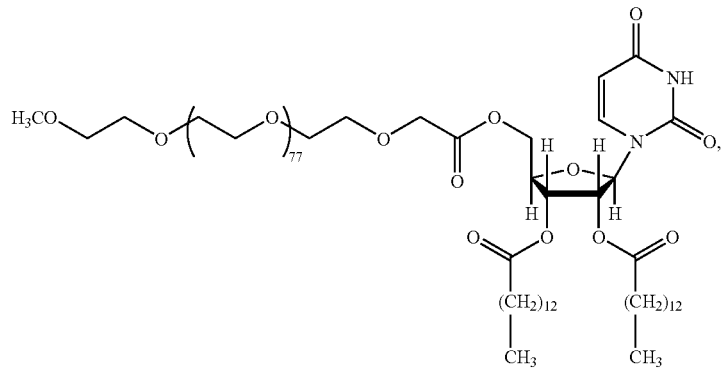
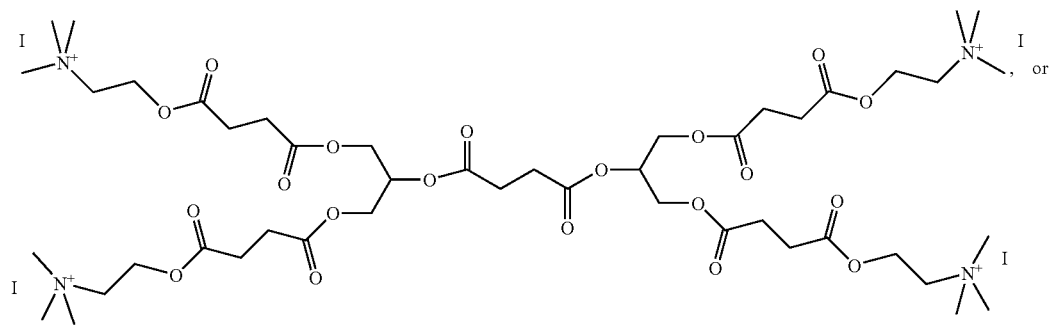
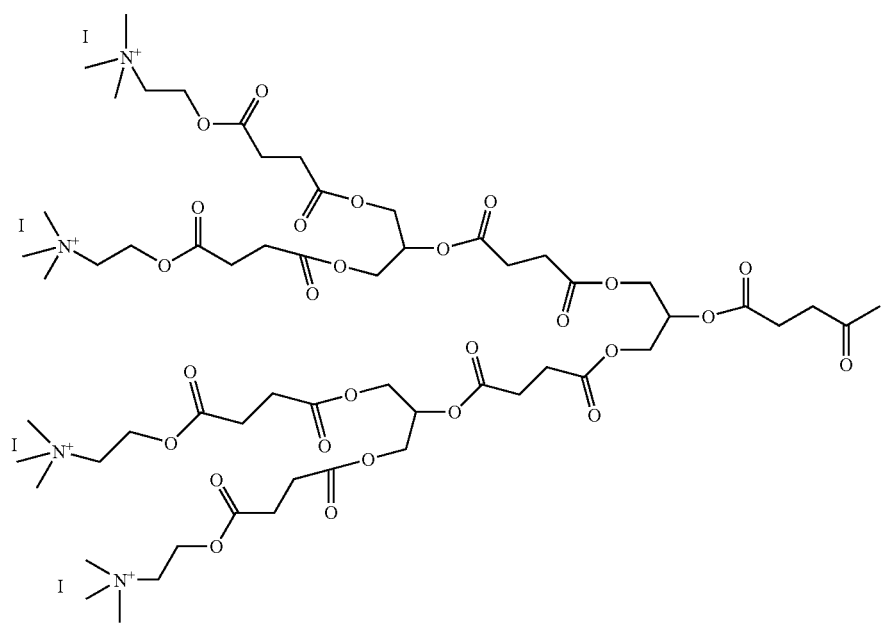

-continued

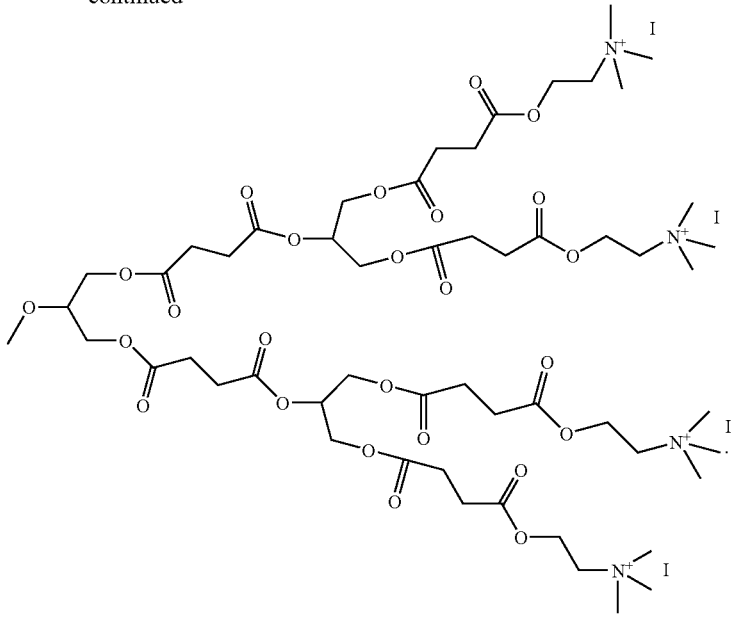

Another aspect of the present invention relates to a compound represented by formula II:

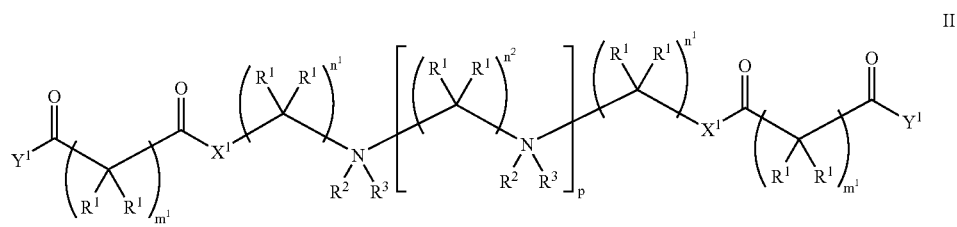

wherein $X^1$ represents independently for each occurrence O or —N($R^4$)—;

$X^2$ represents independently for each occurrence O or —N($R^4$)—;

$Y^1$ represents independently for each occurrence —$OR^5$ or —N($R^4$)$R^6$;

$Y^2$ represents independently for each occurrence —$OR^7$ or —N($R^4$)$R^8$;

$Y^3$ represents independently for each occurrence —$OR^9$ or —N($R^4$)$R^{10}$;

$R^1$ represents independently for each occurrence H, alkyl, or halogen;

$R^2$ represents independently for each occurrence H, alkyl, aryl, or aralkyl;

$R^3$ represents independently for each occurrence H.A, alkyl.A, aryl.A, or aralkyl.A;

$R^4$ represents independently for each occurrence H, alkyl, aryl, or aralkyl;

$R^5$ represents independently for each occurrence alkyl, aryl, aralkyl, or $R^6$ is

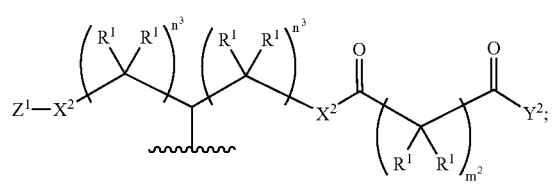

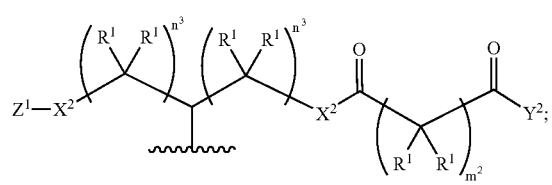

$R^7$ represents independently for each occurrence $R^{12}$, alkyl, aryl, aralkyl, or

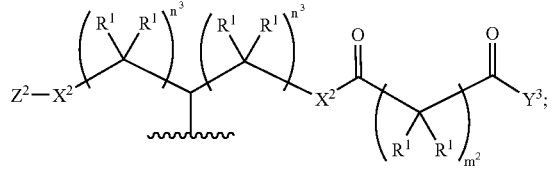

$R^8$ is $R^{12}$ or

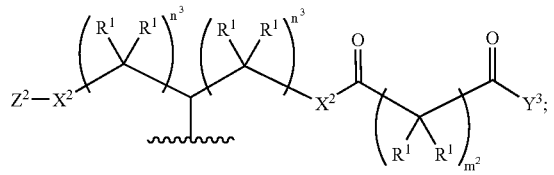

$R^9$ represents independently for each occurrence $R^{13}$, alkyl, aryl, aralkyl, or

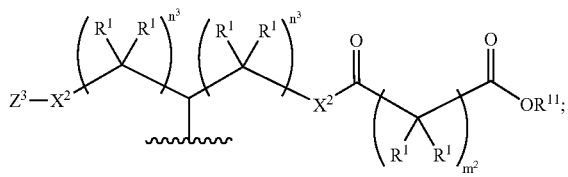

$R^{10}$ is $R^{13}$ or

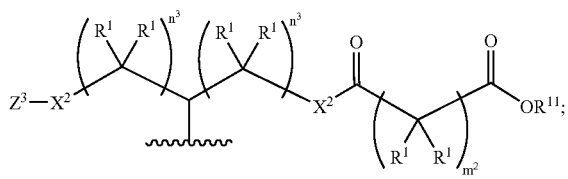

$R^{11}$ represents independently for each occurrence $R^{14}$, alkyl, aryl, or aralkyl;

$R^{12}$, $R^{13}$, and $R^{14}$ are H;

$Z^1$ represents independently for each occurrence $R^{12}$ or

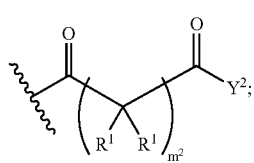

$Z^2$ represents independently for each occurrence $R^{13}$ or

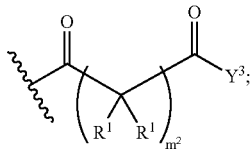

$Z^3$ represents independently for each occurrence $R^{14}$ or

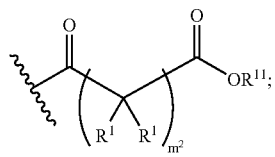

$m^1$ and $m^2$ each represent independently for each occurrence 1, 2, 3, 4, 5, 6, 7, 8, 9, 10, 11, 12, 13, or 14;

$n^1$, $n^2$, and $n^3$ each represent independently for each occurrence 1, 2, 3, 4, 5, 6, 7, 8, 9, or 10; and p is 0, 1, 2, 3, 4, or 5;

A is an anion with a net charge of negative one; and provided that $R^{12}$ only occurs once, $R^{13}$ only occurs once, and $R^{14}$ only occurs once.

In certain embodiments, the present invention relates to the aforementioned compound, wherein A is halogen or $R_{16}CO_2^-$ wherein $R_{16}$ is alkyl, aryl, or aralkyl.

In certain embodiments, the present invention relates to the aforementioned compound, wherein A is halogen.

In certain embodiments, the present invention relates to the aforementioned compound, wherein $R^1$ is H.

In certain embodiments, the present invention relates to the aforementioned compound, wherein $R^2$ is H or alkyl.

In certain embodiments, the present invention relates to the aforementioned compound, wherein $X^2$ is O, and $n^3$ is 1 or 2, and $m^1$ is 4, 5, 6, 7, or 8.

In certain embodiments, the present invention relates to the aforementioned compound, wherein $X^2$ is O; and $n^3$ is 1 or 2; $m^1$ is 1, 2, or 3; and $m^2$ is 4, 5, 6, 7, or 8.

In certain embodiments, the present invention relates to the aforementioned compound, wherein $R^5$ is optionally substituted benzyl.

In certain embodiments, the present invention relates to the aforementioned compound, wherein $R^5$ is benzyl.

In certain embodiments, the present invention relates to the aforementioned compound, wherein $R^7$ is optionally substituted benzyl.

In certain embodiments, the present invention relates to the aforementioned compound, wherein $R^7$ is benzyl.

In certain embodiments, the present invention relates to the aforementioned compound, wherein p is 0, $R^1$ is H, $R^2$ is alkyl, $R^3$ is alkyl.A, $n^1$ is 2, $X^1$ is O, $m^1$ is 4 or 8, and $Y^1$ is $OR^5$, $R^5$ is aralkyl, and A is halogen or $R_{16}CO_2^-$, wherein $R_{16}$ is alkyl, aryl, or aralkyl.

In certain embodiments, the present invention relates to the aforementioned compound, wherein p is 0, $R^1$ is H, $R^2$ is alkyl, $R^3$ is alkyl.A, $n^1$ is 2, $X^1$ and $X^2$ are O, $m^1$ is 2, $m^2$ is 4 or 8, and $Y^1$ is $OR^5$, $R^5$ is

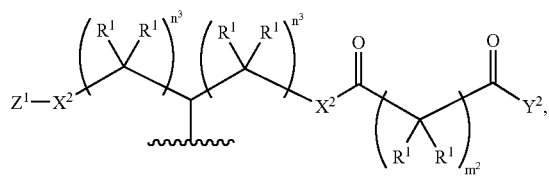

$n^3$ is 1, $Z^1$ is

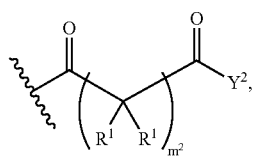

$Y^2$ is $-OR^7$, $R^7$ is aralkyl, and A is halogen or $R_{16}CO_2^-$, wherein $R_{16}$ is alkyl, aryl, or aralkyl.

In certain embodiments, the present invention relates to the aforementioned compound, wherein p is 0, $R^1$ is H, $R^2$ is alkyl, $R^3$ is alkyl.A, $n^1$ is 2, $X^1$ is $-N(H)-$, $m^1$ is 4 or 8, and $Y^1$ is $OR^5$, $R^5$ is aralkyl, and A is halogen or $R_{16}CO_2^-$, wherein $R_{16}$ is alkyl, aryl, or aralkyl.

In certain embodiments, the present invention relates to the aforementioned compound, wherein p is 0, $R^1$ is H, $R^2$ is H, $R^3$ is H.A, $n^1$ is 2, $X^1$ is $-N(H)-$, $X^2$ is O, $m^1$ is 2, and $m^2$ is 4 or 8, and $Y^1$ is $OR^5$, $R^5$ is

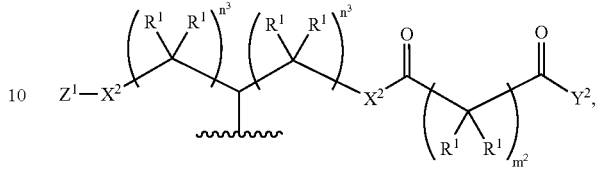

$n^3$ is 1, $Z^1$ is

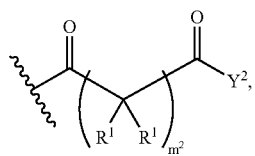

$Y^2$ is $-OR^7$, $R^7$ is aralkyl; and A is halogen or $R_{16}CO_2^-$, wherein $R_{16}$ is alkyl, aryl, or aralkyl.

In certain embodiments, the present invention relates to the aforementioned compound, wherein said compound of formula II is

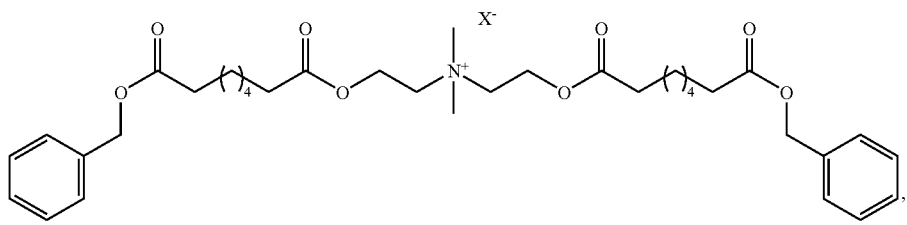

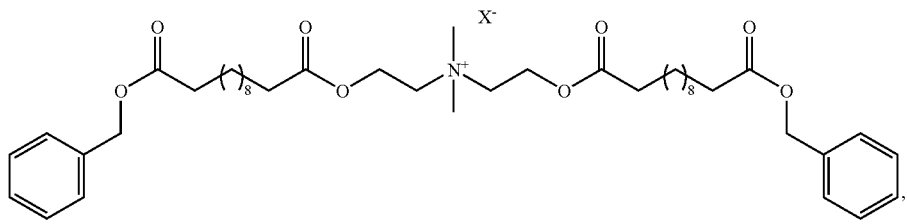

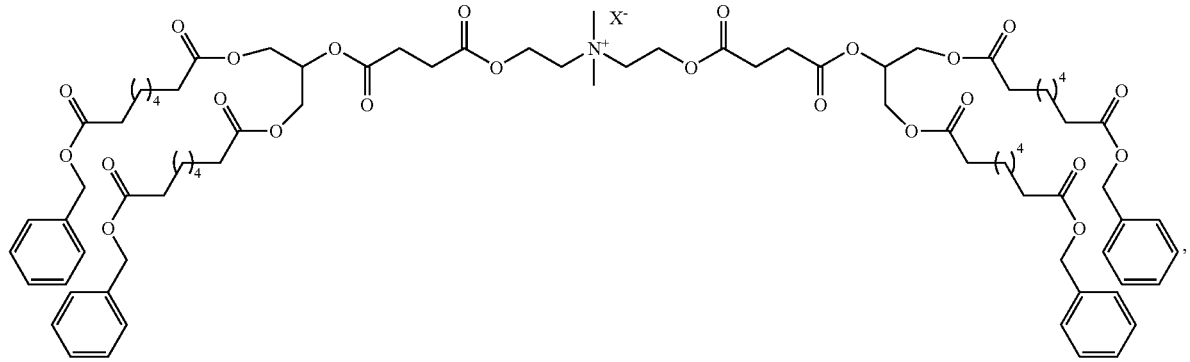

-continued
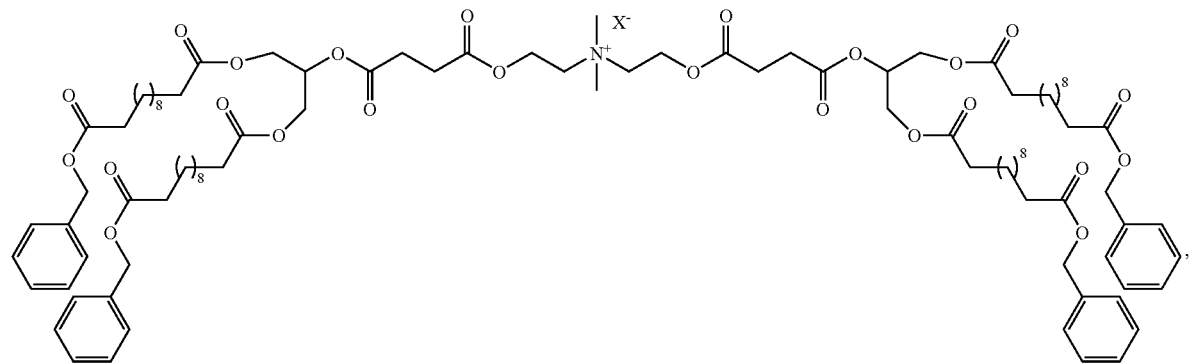
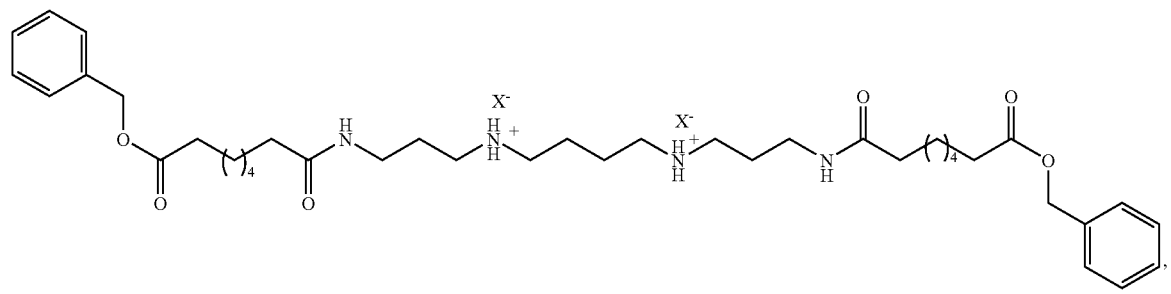
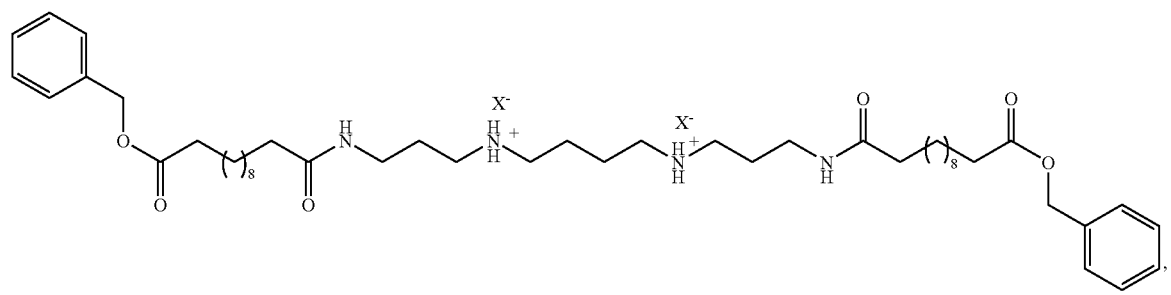
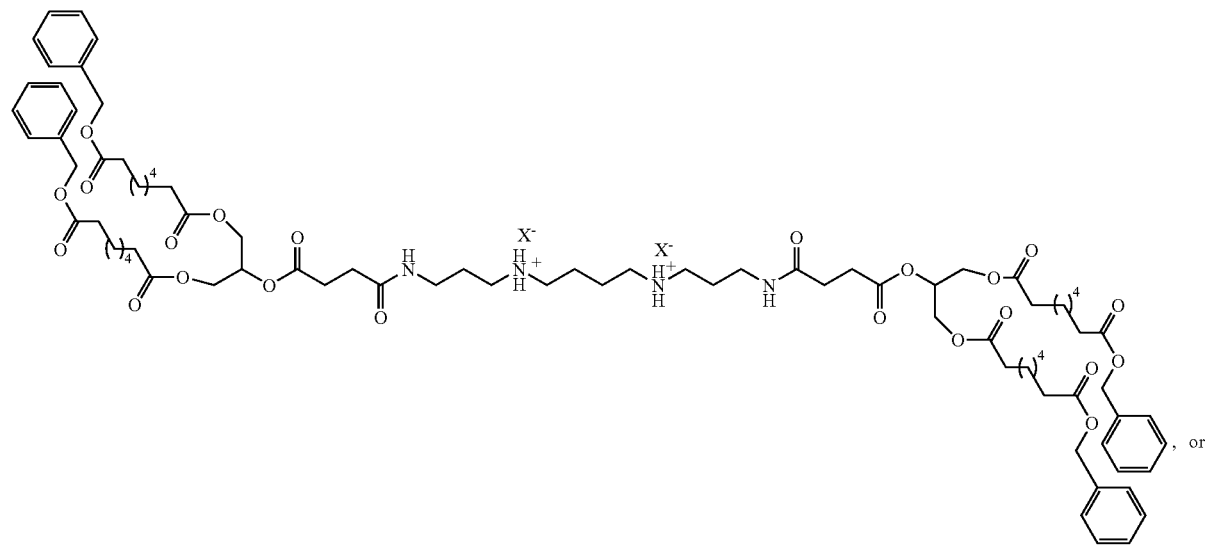

-continued

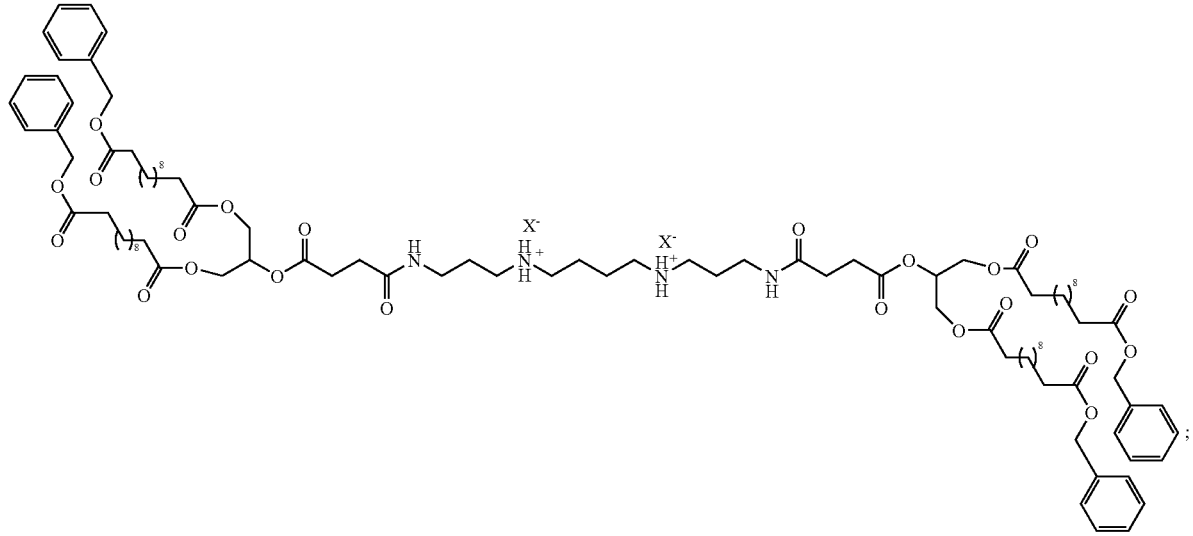

wherein X is halogen.

Another aspect of the present invention relates to a compound represented by formula III:

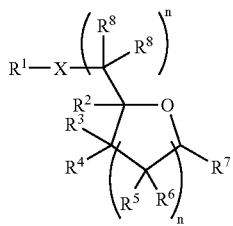

wherein
$R^1$ is —P(O)(OM)O—(C($R^8$)$_2$)$_m$—N($R^9$)$_3$.A, monosaccharide radical, or disaccharide radical;

$R^2$, $R^3$, $R^6$, and $R^8$ each represent independently for each occurrence H, halogen, or alkyl;

$R^4$ and $R^5$ each represent independently for each occurrence alkyl, alkoxyl, —N, —C(O)$R^{10}$, —C(O)O$R^{10}$, —OC(O)$R^{10}$, —C(O)S$R^{10}$, —SC(O)$R^{10}$, —C(O)N($R^{11}$)$R^{10}$, —N($R^{11}$)C(O)$R^{10}$, —OC(O)N($R^{11}$)$R^{10}$, —N($R^{11}$)CO$_2$$R^{10}$, —N($R^{11}$)C(O)N($R^{11}$)$R^{10}$, or —OP(O)(OM)O$R^{10}$;

$R^7$ is optionally substituted uracil radical, optionally substituted thymine radical, optionally substituted cytosine radical, optionally substituted adenine radical, or optionally substituted guanine radical;

$R^9$ represents independently for each occurrence alkyl, aryl, or aralkyl;

$R^{10}$ represents independently for each occurrence alkyl, alkenyl, (alkyl-substituted alkenyl)alkyl, aryl, or aralkyl;

$R^{11}$ is H, alkyl, aryl, or aralkyl;

X represents independently for each occurrence O or —N($R^{11}$)—;

n represents independently for each occurrence 1 or 2;

m is 1, 2, 3, 4, 5, 6, 7, or 8;

M is an alkali metal; and

A is an anion with a net charge of negative one.

In certain embodiments, the present invention relates to the aforementioned compound, wherein A is halogen or $R_{12}CO_2^-$, wherein $R_{12}$ is alkyl, aryl, or aralkyl.

In certain embodiments, the present invention relates to the aforementioned compound, wherein n is 1; and $R^2$, $R^3$, $R^6$, $R^8$ are H.

In certain embodiments, the present invention relates to the aforementioned compound, wherein $R^{10}$ and $R^{11}$ are independently ($C_6$-$C_{10}$)alkyl, ($C_{11}$-$C_{15}$)alkyl, ($C_{16}$-$C_{20}$)alkyl, ($C_{21}$-$C_{25}$)alkyl, —(C($R^8$)$_2$)$_q$C$R^8$=C$R^8$(C($R^8$)$_2$)$_v$CH$_3$, or —(C($R^{10}$)$_2$)$_w$[(C($R^{10}$)$_2$)$_x$C$R^8$=C$R^8$]$_y$(C($R^8$)$_2$)$_z$CH$_3$; wherein, q, v, w, and z each represent independently for each occurrence 2, 3, 4, 5, 6, 7, 8, 9, 10, 11, or 12; and x and y represent independently for each occurrence 1, 2, 3, 4, 5, or 6.

In certain embodiments, the present invention relates to the aforementioned compound, wherein $R^4$ and $R^5$ each represent independently for each occurrence —OC(O)$R^{10}$ or —OC(O)N($R^{11}$)$R^{10}$; and $R^{10}$ is alkyl, —(C($R^8$)$_2$)$_q$C$R^8$=$R^8$(C($R^8$)$_2$)$_v$CH$_3$, or —(C($R^8$)$_2$)$_w$[(C($R^8$)$_2$)$_x$C$R^8$=C$R^8$]$_y$(C($R^8$)$_2$)$_z$CH$_3$; wherein, q, v, w, and z each represent independently for each occurrence 2, 3, 4, 5, 6, 7, 8, 9, 10, 11, or 12; and x and y represent independently for each occurrence 1, 2, 3, 4, 5, or 6.

In certain embodiments, the present invention relates to the aforementioned compound, wherein $R^4$ and $R^5$ each represent independently for each occurrence —OC(O)$R^{10}$ or —OC(O)N($R^{11}$)$R^{10}$; and $R^{10}$ is alkyl, —(C($R^8$)$_2$)$_q$C$R^8$=C$R^8$(C($R^8$)$_2$)$_v$CH$_3$ or —(C($R^8$)$_2$)$_w$[(C($R^8$)$_2$)$_x$C$R^8$=C$R^8$]$_y$(C($R^8$)$_2$)$_z$CH$_3$; wherein, q and v each represent independently for each occurrence 6, 7, 8, or 9; and w, x, y, and z represent independently for each occurrence 1, 2, 3, 4, 5, or 6.

In certain embodiments, the present invention relates to the aforementioned compound, wherein $R^4$ and $R^5$ are —OC(O)$R^{10}$ or —OC(O)N(H)$R^{10}$; and $R^{10}$ represents independently for each occurrence ($C_{11}$-$C_{15}$)alkyl or ($C_{16}$-$C_{20}$)alkyl.

In certain embodiments, the present invention relates to the aforementioned compound, wherein R⁷ is

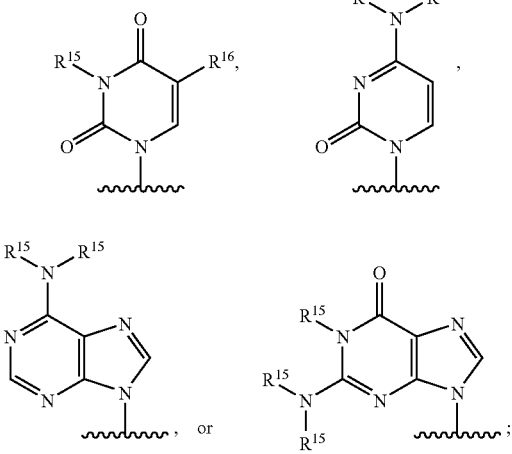

wherein R¹⁵ represents independently for each occurrence H, alkyl, or aralkyl; and R¹⁶ represents independently for each occurrence H, alkyl, or aralkyl.

In certain embodiments, the present invention relates to the aforementioned compound, wherein R⁷ is

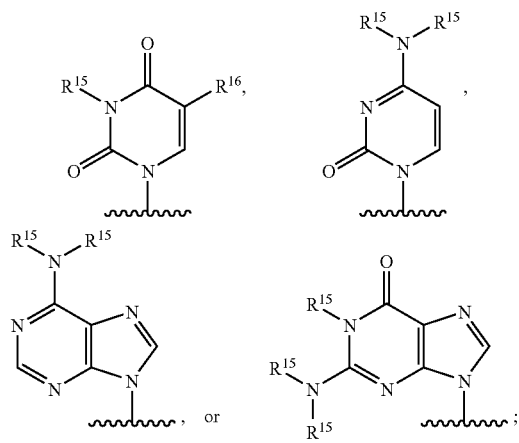

wherein R¹⁵ is H, and R¹⁶ is alkyl.

In certain embodiments, the present invention relates to the aforementioned compound, wherein R⁷ is

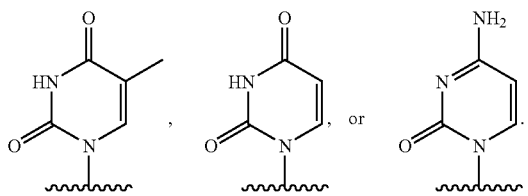

In certain embodiments, the present invention relates to the aforementioned compound, wherein R⁷ is

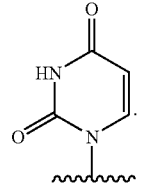

In certain embodiments, the present invention relates to the aforementioned compound, wherein R¹ is —P(O)(OM)O—(C(R⁸)₂)ₘ—N(R⁹)₃.A, a quatrose sugar radical, a pentose sugar radical, or a hexose sugar radical.

In certain embodiments, the present invention relates to the aforementioned compound, wherein R¹ is —P(O)(OM)O—(C(R⁸)₂)ₘ—N(R⁹)₃.A.

In certain embodiments, the present invention relates to the aforementioned compound, wherein R¹ is —P(O)(O(OM)O—(C(R⁸)₂)—N(R⁹)₃.A, R8 is H, m is 2 or 3, and R⁹ is (C₁-C₄)alkyl.

In certain embodiments, the present invention relates to the aforementioned compound, wherein R¹ is the radical of a sugar selected from the group consisting of erythrose, threose, ribose, arabinose, xylose, lyxose, allose, altrose, glucose, mannose, gulose, idose, galactose, and talose.

In certain embodiments, the present invention relates to the aforementioned compound, wherein R¹ is the radical of a sugar selected from the group consisting of erythrose, threose, ribose, arabinose, xylose, lyxose, allose, altrose, glucose, mannose, gulose, idose, galactose, and talose.

In certain embodiments, the present invention relates to the aforementioned compound, wherein R¹ is the radical of glucose.

In certain embodiments, the present invention relates to the aforementioned compound, wherein n is 1; R², R³, R⁶, R⁸ are H; R⁴ and R⁵ each represent independently for each occurrence —OC(O)R¹⁰ or —OC(O)N(R¹¹)R¹⁰; and R¹⁰ is alkyl, —(C(R⁸)₂)qCR⁸=CR⁸(C(R⁸)₂)ᵥCH₃, or —(C(R⁸)₂)w[(C(R⁸)₂)ₓCR⁸=CR⁸]y(C(R⁸)₂)zCH₃; wherein, q and v each represent independently for each occurrence 6, 7, 8, or 9; and w, x, y, and z represent independently for each occurrence 1, 2, 3, 4, 5, or 6.

In certain embodiments, the present invention relates to the aforementioned compound, wherein n is 1; R², R³, R⁶, R⁸ are H; R⁴ and R⁵ each represent independently for each occurrence —OC(O)R¹⁰ or —OC(O)N(R¹¹)R¹⁰; R¹⁰ represents independently for each occurrence (C₆-C₁₀)alkyl, (C₁₁-C₁₅)alkyl, (C₁₆-C₂₀)alkyl, (C₂₁-C₂₅)alkyl, —(C(R⁸)₂)qCR⁸=CR⁸(C(R⁸)₂)ᵥCH₃, or —(C(R⁸)₂)w[(C(R⁸)₂)ₓCR⁸=CR⁸]y(C(R⁸)₂)zCH₃; q and v each represent independently for each occurrence 6, 7, 8, or 9; w, x, y, and z represent independently for each occurrence 1, 2, 3, 4, 5, or 6; R⁷ is In certain embodiments, the present invention relates to the aforementioned compound, wherein n is 1; R², R³, R⁶, R⁸ are H; R⁴ and R⁵ each represent independently for each occurrence —OC(O)R$^{10}$ or —OC(O)N(R$^{11}$)R$^{10}$; R$^{10}$ represents independently for each occurrence (C$_6$-C$_{10}$)alkyl, (C$_{11}$-C$_{15}$)alkyl, (C$_{16}$-C$_{20}$)alkyl, (C$_{21}$-C$_{25}$)alkyl, —(C(R$^8$)$_2$)$_q$CR$^8$=CR$^8$(C(R$^8$)$_2$)$_v$CH$_3$, or —(C(R$^8$)$_2$)$_w$[(C(R$^8$)$_2$)$_x$CR$^8$=CR$^8$]$_y$(C(R$^8$)$_2$)$_z$CH$_3$; q and v each represent independently for each occurrence 6, 7, 8, or 9; w, x, y, and z represent independently for each occurrence 1, 2, 3, 4, 5, or 6; and R$^7$ is

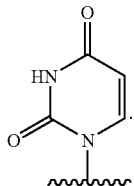

In certain embodiments, the present invention relates to the aforementioned compound, wherein n is 1; R$^2$, R$^3$, R$^6$, R$^8$ are H; R$^4$ and R$^5$ each represent independently for each occurrence —OC(O)R$^{10}$ or —OC(O)N(R$^{11}$)R$^{10}$; R$^{10}$ represents independently for each occurrence (C$_6$-C$_{10}$)alkyl, (C$_{11}$-C$_{15}$)alkyl, (C$_{16}$-C$_{20}$)alkyl, (C$_{21}$-C$_{25}$)alkyl, —(C(R$^8$)$_2$)$_q$CR$^8$=CR$^8$(C(R$^8$)$_2$)$_v$CH$_3$, or —(C(R$^8$)$_2$)$_w$[(C(R$^8$)$_2$)$_x$CR$^8$=CR$^8$]$_y$(C(R$^8$)$_2$)$_z$CH$_3$; q and v each represent independently for each occurrence 6, 7, 8, or 9; w, x, y, and z represent independently for each occurrence 1, 2, 3, 4, 5, or 6; and R$^7$ is

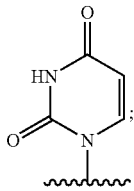

and R$^1$ is —P(O)(OM)O—(C(R$^8$)$_2$)$_m$—N(R$^9$)$_3$.A.

In certain embodiments, the present invention relates to the aforementioned compound, wherein n is 1; R$^2$, R$^3$, R$^6$, R$^8$ are H; R$^4$ and R$^5$ each represent independently for each occurrence —OC(O)R$^{10}$ or —OC(O)N(R$^{11}$)R$^{10}$; R$^{10}$ represents independently for each occurrence (C$_6$-C$_{10}$)alkyl, (C$_{11}$-C$_{15}$)alkyl, (C$_{16}$-C$_{20}$)alkyl, (C$_{21}$-C$_{25}$)alkyl, —(C(R$^8$)$_2$)$_q$CR$^8$=CR$^8$(C(R$^8$)$_2$)$_v$CH$_3$, or —(C(R$^8$)$_2$)$_w$[(C(R$^8$)$_2$)$_x$CR$^8$=CR$^8$]$_y$(C(R$^8$)$_2$)$_z$CH$_3$; q and v each represent independently for each occurrence 6, 7, 8, or 9; w, x, y, and z represent independently for each occurrence 1, 2, 3, 4, 5, or 6; and R$^7$ is

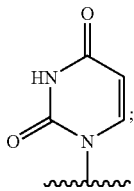

R$^1$ is —P(O)(OM)O—(C(R$^8$)$_2$)$_m$—N(R$^9$)$_3$.A; R$^9$ is alkyl; m is 2 or 3; A is halogen or R$_{12}$CO$_2^-$, and R$_{12}$ is alkyd, aryl, or aralkyl.

In certain embodiments, the present invention relates to the aforementioned compound, wherein n is 1; R$^2$, R$^3$, R$^6$, R$^8$ are H; R$^4$ and R$^5$ each represent independently for each occurrence —OC(O)R$^{10}$ or —OC(O)N(R$^{11}$)R$^{10}$; R$^{10}$ represents independently for each occurrence (C$_6$-C$_{10}$)alkyl, (C$_{11}$-C$_{15}$)alkyl, (C$_{16}$-C$_{20}$)alkyl, (C$_{21}$-C$_{25}$)alkyl, —(C(R$^8$)$_2$)$_q$CR$^8$=CR$^8$(C(R$^8$)$_2$)$_v$CH$_3$, or —(C(R$^8$)$_2$)$_w$[(C(R$^8$)$_2$)$_x$CR$^8$=CR$^8$]$_y$(C(R$^8$)$_2$)$_z$CH$_3$; q and v each represent independently for each occurrence 6, 7, 8, or 9; w, x, y, and z represent independently for each occurrence 1, 2, 3, 4, 5, or 6; and R$^7$ is

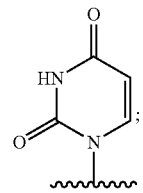

and R$^1$ radical of a sugar selected from the group consisting of erythrose, threose, ribose, arabinose, xylose, lyxose, allose, altrose, glucose, mannose, gulose, idose, galactose, and talose.

In certain embodiments, the present invention relates to the aforementioned compound, wherein n is 1; R$^2$, R$^3$, R$^6$, R$^8$ are H; R$^4$ and R$^5$ each represent independently for each occurrence —OC(O)R$^{10}$ or —OC(O)N(R$^{11}$)R$^{10}$; R$^{10}$ represents independently for each occurrence (C$_6$-C$_{10}$)alkyl, (C$_{11}$-C$_{15}$)alkyl, (C$_{16}$-C$_{20}$)alkyl, (C$_{21}$-C$_{25}$)alkyl, —(C(R$^8$)$_2$)$_q$CR$^8$=CR$^8$(C(R$^8$)$_2$)$_v$CH$_3$, or —(C(R$^8$)$_2$)$_w$[(C(R$^8$)$_2$)$_x$CR$^8$=CR$^8$]$_y$(C(R$^8$)$_2$)$_z$CH$_3$; q and v each represent independently for each occurrence 6, 7, 8, or 9; w, x, y, and z represent independently for each occurrence 1, 2, 3, 4, 5, or 6; and R$^7$ is

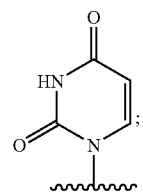

and R$^1$ radical of glucose.

In certain embodiments, the present invention relates to the aforementioned compound, wherein said compound of formula III is

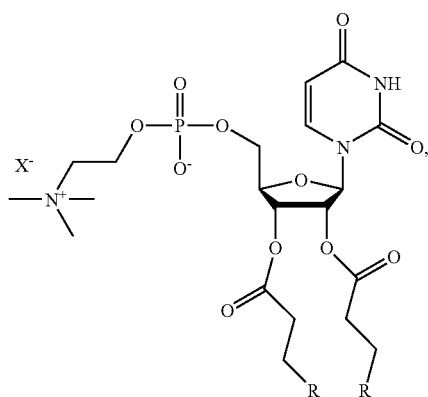

R = myristoyl

-continued

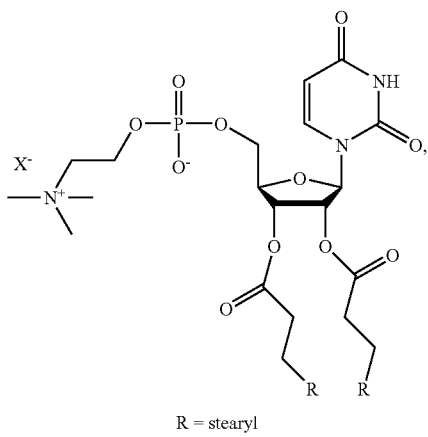

R = stearyl

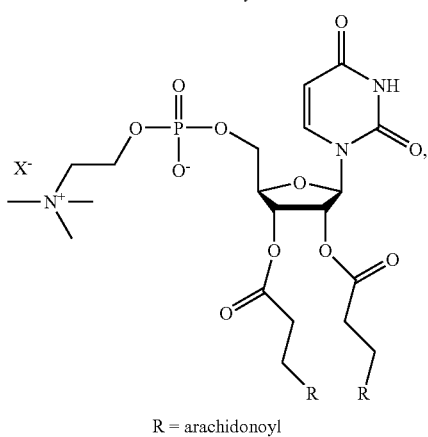

R = arachidonoyl

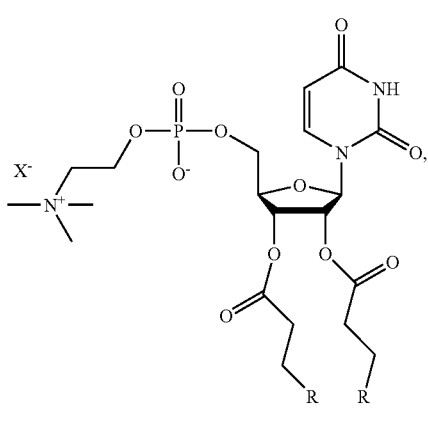

R = oleyl

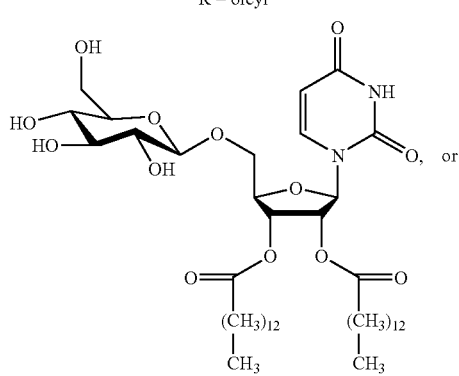

-continued

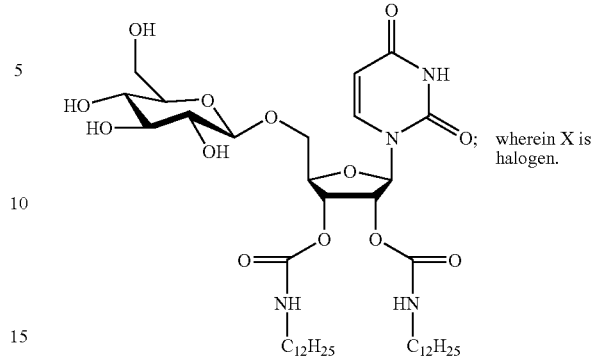

wherein X is halogen.

Another aspect of the present invention relates to a compound represented by formulas IV:

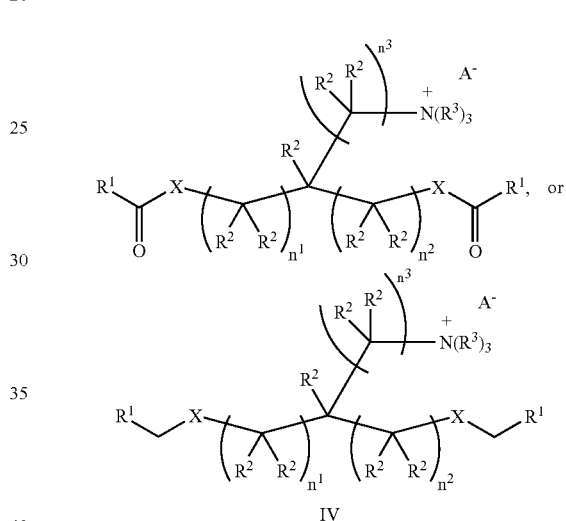

IV wherein

X represents independently for each occurrence O or —N($R^4$)—;

Y represents independently for each occurrence —N($R^4$)—, or —C($R^2$)$_2$—;

Z represents independently for each occurrence O or —N($R^5$)—;

$R^1$ is alkyl, aryl, aralkyl,

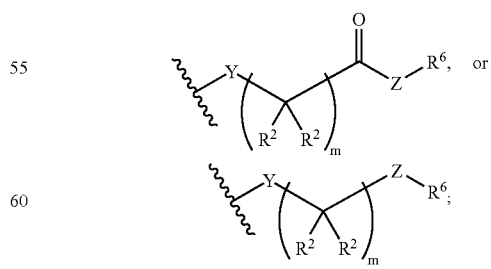

$R^2$ is H, alkyl, or halogen;

$R^3$, $R^4$, and $R^5$ represent independently for each occurrence H, alkyl, aryl, or aralkyl;

R⁶ is alkyl, aryl, aralkyl, or a photocleavable protecting group having a molecular weight less than 700 g/mol;

m represents independently for each occurrence 5, 6, 7, 8, 9, 10, 11, 12, 13, 14, 15, 16, 17, 18, 19, 20, 21, 22, 23, 24, or 25;

$n^1$, $n^2$, and $n^3$ each represent independently 0, 1, 2, 3, 4, 5, 6, 7, or 8; and A is an anion with a net charge of negative one.

In certain embodiments, the present invention relates to the aforementioned compound, wherein A is halogen or $R_{12}CO_2^-$, wherein $R_{12}$ is alkyl, aryl, or aralkyl.

In certain embodiments, the present invention relates to the aforementioned compound, wherein X is O.

In certain embodiments, the present invention relates to the aforementioned compound, wherein $R^2$ is H.

In certain embodiments, the present invention relates to the aforementioned compound, wherein $n^1$ is 0, $n^2$ is 1, $n^3$ is 1, and m represents independently for each occurrence 7, 8, 9, 10, 11, 12, 13, 14, 15, 16, or 17.

In certain embodiments, the present invention relates to the aforementioned compound, wherein $R^1$ is

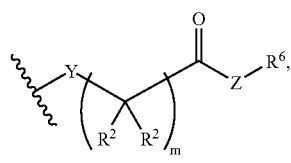

and $R^6$ is alkyl.

In certain embodiments, the present invention relates to the aforementioned compound, wherein $R^1$ is

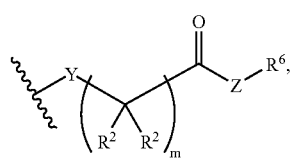

and $R^6$ is aralkyl.

In certain embodiments, the present invention relates to the aforementioned compound, wherein $R^1$ is

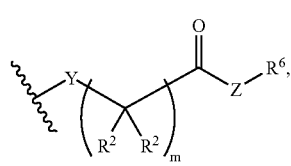

and $R^6$ is optionally substituted benzyl.

In certain embodiments, the present invention relates to the aforementioned compound, wherein $R^1$ is

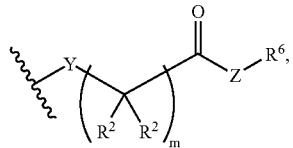

and $R^6$ is nitrobenzyl.

In certain embodiments, the present invention relates to the aforementioned compound, wherein $R^1$ is

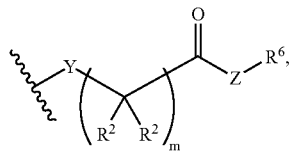

and $R^6$ is benzyl.

In certain embodiments, the present invention relates to the aforementioned compound, wherein $R^1$ is

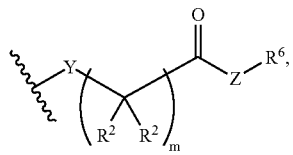

and $R^6$ is a photocleavable protecting group.

In certain embodiments, the present invention relates to the aforementioned compound, wherein $R^1$ is

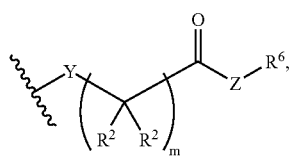

and $R^6$ is a photocleavable protecting group selected from the group consisting of nitrobenzyl and $-(C(R_2)_2)_w-R^{30}$, wherein $R^{30}$ is bicyclic ring having 8 to 14 atoms of which 0, 1, 2, or 3 atoms are heteroatoms selected from the group consisting of O and N, and w is 1, 2, or 3.

In certain embodiments, the present invention relates to the aforementioned compound, wherein $R^1$ is

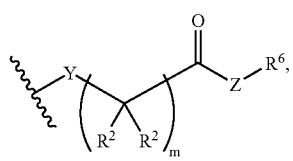

and $R^6$ is the radical of 6-bromo-7-hydroxycoumarin-4-ylmethyl or 8-bromo-7-hydroxyquinoline-2-yl-methyl.

In certain embodiments, the present invention relates to the aforementioned compound, wherein $R^1$ is

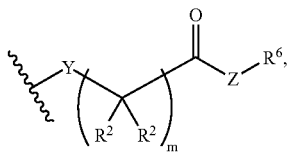

and $R^6$ is

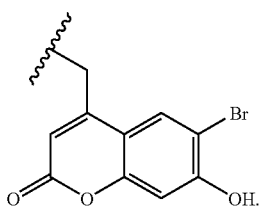

In certain embodiments, the present invention relates to the aforementioned compound, wherein X is O, Y is —N($R^4$)—, Z is O, $R^1$ is

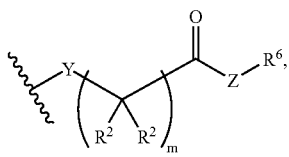

$R^2$ is H, $R^4$ is is H or alkyl, and $R^6$ is alkyl.

In certain embodiments, the present invention relates to the aforementioned compound, wherein X is O, Y is —N($R^4$)—, Z is O, $R^1$ is

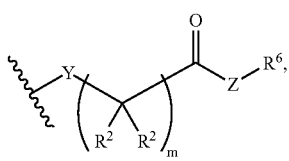

$R^2$ is H, $R^4$ is is H or alkyl, $R^6$ is alkyl, $n^1$ is 0, $n^2$ is 1, $n^3$ is 1, and m represents independently for each occurrence 9, 10, 11, 12, 13, 14, 15, 16, or 17.

In certain embodiments, the present invention relates to the aforementioned compound, wherein X is O, Y is —N($R^4$)—, Z is O, $R^1$ is

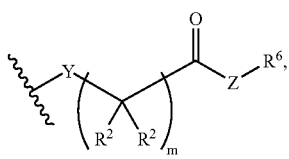

$R^2$ is H, $R^4$ is is H or alkyl, $R^6$ is alkyl, $R^3$ is alkyl, A is halogen, $n^1$ is 0, $n^2$ is 1, $n^3$ is 1, and m represents independently for each occurrence 9, 10, 11, 12, 13, 14, 15, 16, or 17.

In certain embodiments, the present invention relates to the aforementioned compound, wherein X is O, Y is —N($R^4$)—, Z is —N($R^5$)—, $R^1$ is

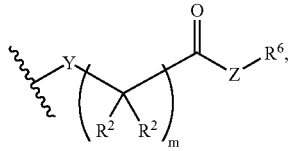

$R^2$ is H, $R^4$ is H or alkyl, $R^5$ is alkyl, and $R^6$ is alkyl.

In certain embodiments, the present invention relates to the aforementioned compound, wherein X is O, Y is —N($R^4$)—, Z is —N($R^5$)—, $R^1$ is

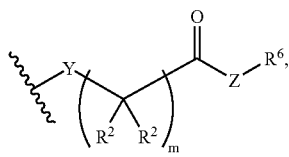

$R^2$ is H, $R^4$ is H or alkyl, $R^5$ is alkyl, $R^6$ is alkyl, $n^1$ is 0, $n^2$ is 1, $n^3$ is 1, and m represents independently for each occurrence 9, 10, 11, 12, 13, 14, 15, 16, or 17.

In certain embodiments, the present invention relates to the aforementioned compound, wherein X is O, $Y^1$ is —N($R^4$)—, Z is —N($R^5$)—, $R^1$ is

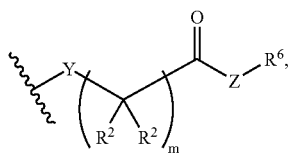

$R^2$ is H, $R^4$ is H or alkyl, $R^5$ is alkyl, $R^6$ is alkyl, $R^3$ is alkyl, A is halogen, $n^1$ is 0, $n^2$ is 1, $n^3$ is 1, and m represents independently for each occurrence 9, 10, 11, 12, 13, 14, 15, 16, or 17.

In certain embodiments, the present invention relates to the aforementioned compound, wherein X is O, Y is —N($R^4$)—, Z is O, $R^1$ is

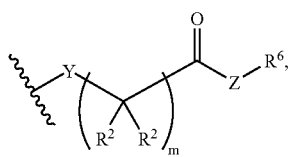

$R^2$ is H, $R^3$ is alkyl, $R^4$ is H or alkyl $R^6$ is

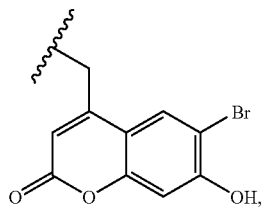

A is halogen, $n^1$ is 0, $n^2$ is 1, $n^3$ is 1, and m represents independently for each occurrence 9, 10, 11, 12, or 13.

In certain embodiments, the present invention relates to the aforementioned compound, wherein X is O, Y is —C($R^2$)$_2$—, Z is O, $R^1$ is

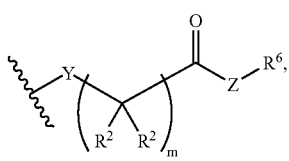

$R^2$ is H, $R^3$ is alkyl, $R^6$ is aralkyl, A is halogen, $n^1$ is 0, $n^2$ is 1, $n^3$ is 1, and m represents independently for each occurrence 7, 8, 9, 10, or 11.

In certain embodiments, the present invention relates to the aforementioned compound, wherein X is O, Y is —C($R^2$)$_2$—, Z is O, $R^1$ is

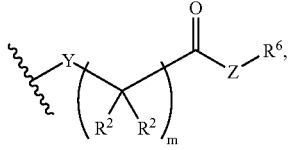

$R^2$ is H, $R^3$ is alkyl, $R^6$ is optionally substituted benzyl, A is halogen, $n^1$ is 0, $n^2$ is 1, $n^3$ is 1, and $m^1$ represents independently for each occurrence 7, 8, 9, 10, or 11.

In certain embodiments, the present invention relates to the aforementioned compound, wherein X is O, Y is —C($R^2$)$_2$—, Z is O, $R^1$ is

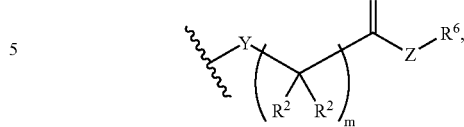

$R^2$ is H, $R^3$ is alkyl, $R^6$ is alkyl, A is halogen, $n^1$ is 0, $n^2$ is 1, $n^3$ is 1, and m represents independently for each occurrence 7, 8, 9, 10, or 11.

In certain embodiments, the present invention relates to the aforementioned compound, wherein X is O, Y is —C($R^2$)$_2$—, Z is O, $R^1$ is

$R^2$ is H, $R^3$ is alkyl, $R^6$ is aralkyl, A is halogen, $n^1$ is 0, $n^2$ is 1, $n^3$ is 1, and m represents independently for each occurrence 7, 8, 9, 10, or 11.

In certain embodiments, the present invention relates to the aforementioned compound, wherein X is O, Y is —C($R^2$)$_2$—, Z is O, $R^1$ is

$R^2$ is H, $R^3$ is alkyl, $R^6$ is optionally substituted benzyl, A is halogen, $n^1$ is 0, $n^2$ is 1, $n^3$ is 1, and m represents independently for each occurrence 7, 8, 9, 10, or 11.

In certain embodiments, the present invention relates to the aforementioned compound, wherein X is O, $R^1$ is alkyl, $R^2$ is H, $R^3$ is alkyl, A is halogen, $n^1$ is 0, $n^2$ is 1, and $n^3$ is 1.

In certain embodiments, the present invention relates to the aforementioned compound, wherein said compound of formula IV is

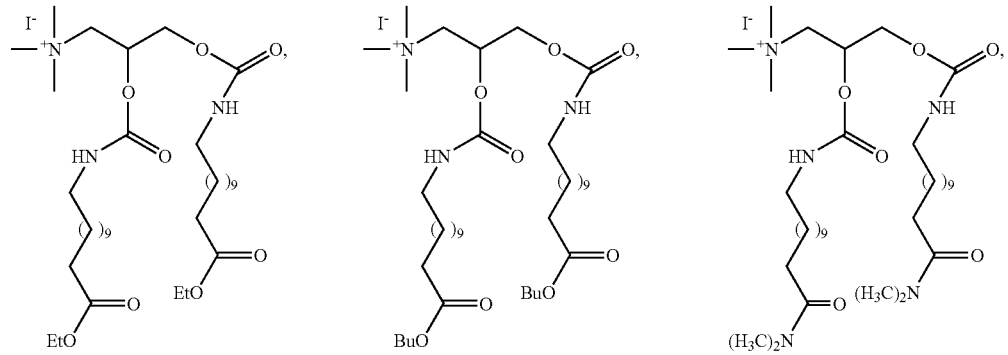

-continued
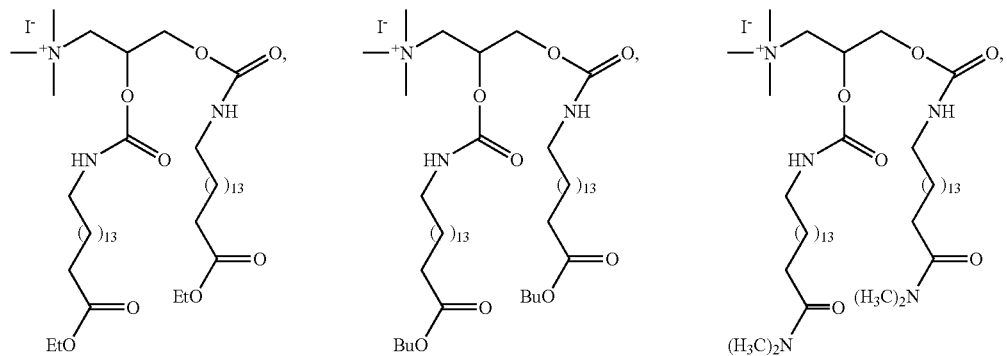
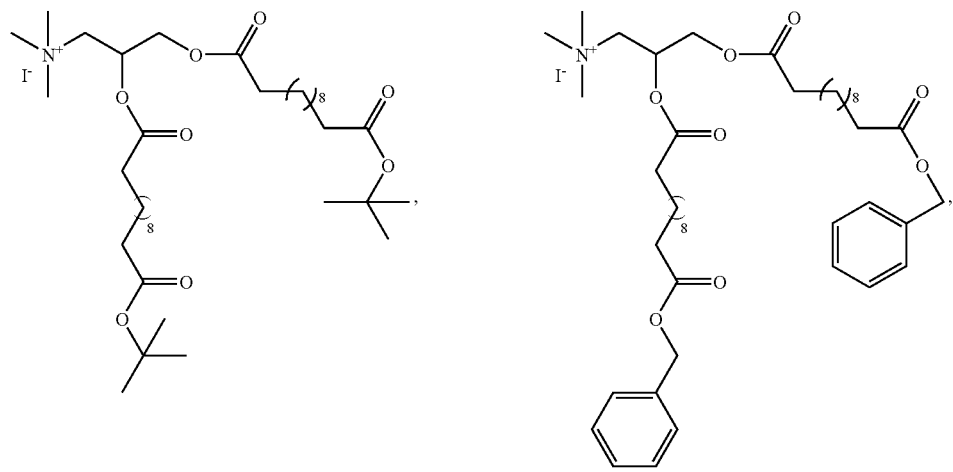
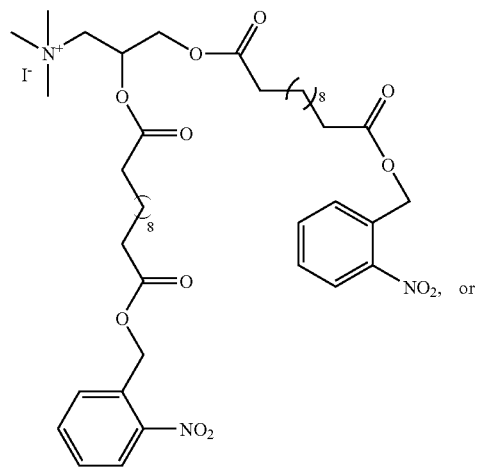

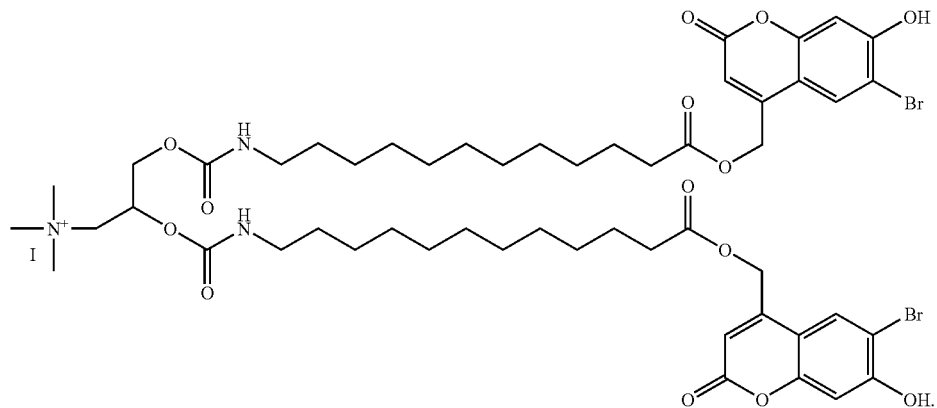

In certain embodiments, the present invention relates to the aforementioned compound, wherein said compound of formula IV is

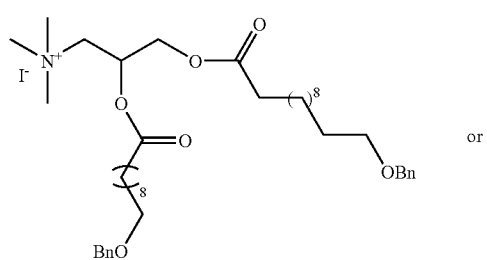

or

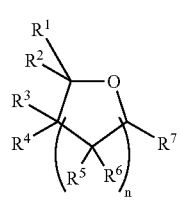

Another aspect of the present invention relates to a compound represented by formula V:

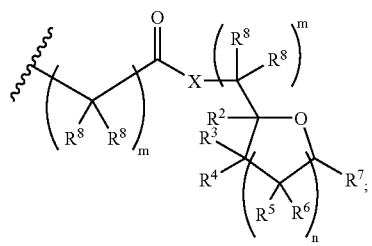

wherein $R^1$ is heteroalkyl, —XC(O)-heteroalkyl, or

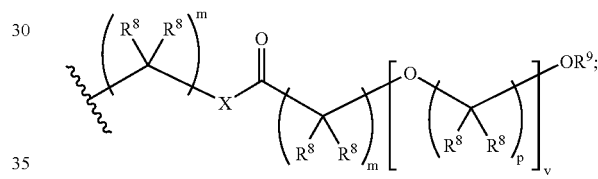

$R^2$, $R^3$, and $R^6$ each represent independently for each occurrence H, halogen, or alkyl;

$R^4$ and $R^5$ each represent independently for each occurrence alkyl, alkoxyl, —N, —C(O)$R^{10}$, —C(O)O$R^{10}$, —OC(O)$R^{10}$, —C(O)S$R^{10}$, —SC(O)$R^{10}$, —C(O)N($R^{11}$)$_2$, —N($R^{11}$)C(O)—, —OC(O)N($R^{11}$)$_2$, —N($R^{11}$)CO$_2R^{10}$, —N($R^{11}$)C(O)N($R^{11}$)$_2$, —OP(O)(OM)O$R^{10}$, or X$R^{12}$;

$R^7$ represents independently for each occurrence —O$R^{10}$, optionally substituted uracil radical, optionally substituted thymine radical, optionally substituted cytosine radical, optionally substituted adenine radical, or optionally substituted guanine radical;

$R^8$ represents independently for each occurrence hydrogen, alkyl, or halogen;

$R^9$ is alkyl, aryl, aralkyl, or represented by formula Va:

$R^{10}$ is alkyl, aryl, or aralkyl;
$R^{11}$ is H, alkyl, aryl, or aralkyl;
$R^{12}$ is

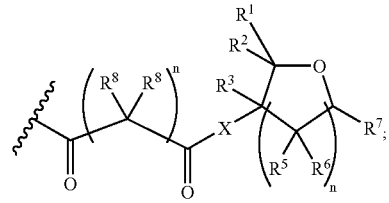

$R^{13}$ is H, alkyl, or aralkyl;
M is an alkali metal or $N(R^{11})_4$;
X represents independently for each occurrence O or $-N(R^{13})-$;
n represents independently for each occurrence 1 or 2;
m represents independently for each occurrence 1, 2, 3, 4, 5, or 6;
p represents independently for each occurrence 2, 3, or 4; and
v is an integer in the range of about 5 to about 75.

In certain embodiments, the present invention relates to the aforementioned compound, wherein n is 1; and $R^2$, $R^3$, and $R^6$ are H.

In certain embodiments, the present invention relates to the aforementioned compound, wherein $R^4$ and $R^5$ each represent independently for each occurrence $-OC(O)R^{10}$ or $-OC(O)N(R^{11})_2$.

In certain embodiments, the present invention relates to the aforementioned compound, wherein $R^4$ and $R^5$ are $-OC(O)R^{10}$.

In certain embodiments, the present invention relates to the aforementioned compound, wherein $R^{10}$ and $R^{11}$ are independently $(C_6-C_{10})$alkyl, $(C_{11}-C_{15})$alkyl, $(C_{16}-C_{20})$alkyl, or $(C_{21}-C_{25})$alkyl;

In certain embodiments, the present invention relates to the aforementioned compound, wherein $R^4$ and $R^5$ are $-OC(O)R^{10}$, and $R^{10}$ represents independently for each occurrence $(C_{11}-C_{15})$alkyl or $(C_{16}-C_{20})$alkyl.

In certain embodiments, the present invention relates to the aforementioned compound, wherein $R^7$ is alkoxy.

In certain embodiments, the present invention relates to the aforementioned compound, wherein $R^7$ is

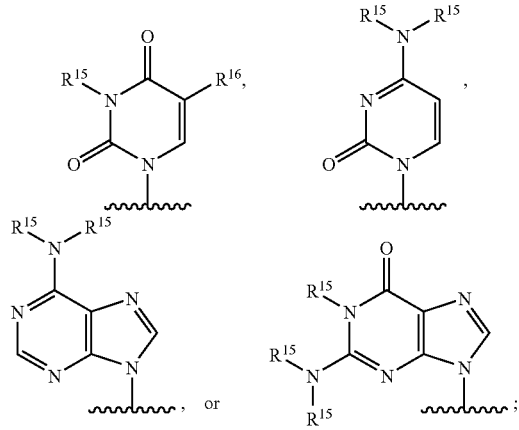

wherein $R^{15}$ represents independently for each occurrence H, alkyl, or aralkyl; and $R^{16}$ represents independently for each occurrence H, alkyl, or aralkyl.

In certain embodiments, the present invention relates to the aforementioned compound, wherein $R^7$ is

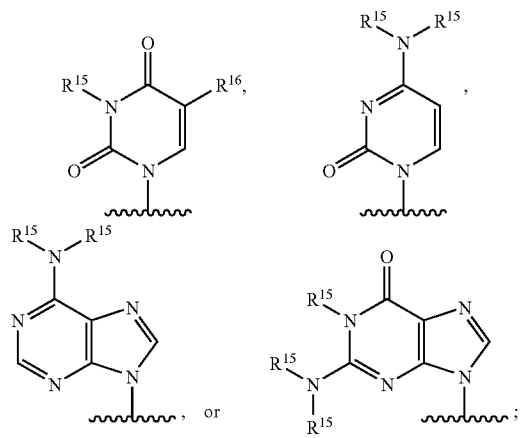

wherein $R^{15}$ is H, and $R^{16}$ is alkyl.

In certain embodiments, the present invention relates to the aforementioned compound, wherein $R^7$ is

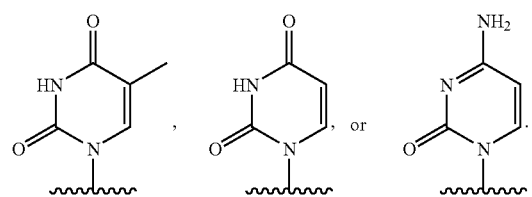

In certain embodiments, the present invention relates to the aforementioned compound, wherein $R^7$ is

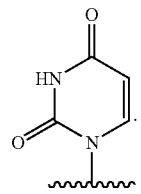

In certain embodiments, the present invention relates to the aforementioned compound, wherein $R^1$ is

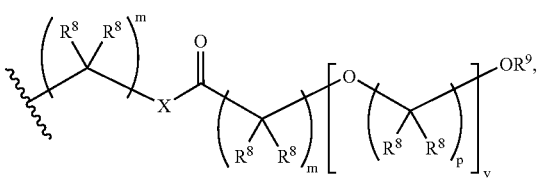

X is O, $R^8$ is H, $R^9$ is alkyl, m is 1, p is 2, and v is 12, 13, 14, 15, 16, 17, 18, 19, or 20.

In certain embodiments, the present invention relates to the aforementioned compound, wherein $R^1$ is

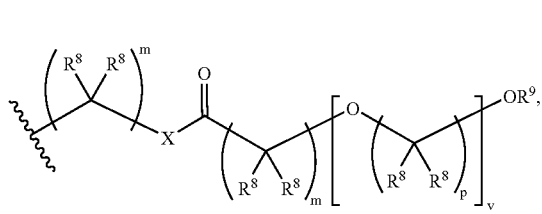

X is O; $R^8$ is H; m is 1; p is 2; v is 12, 13, 14, 15, 16, 17, 18, 19, or 20; and $R^9$ is represented by formula Ia:

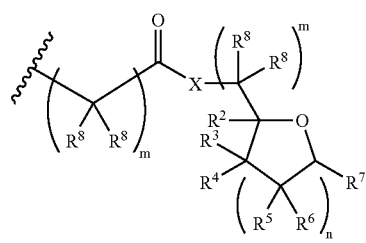

In certain embodiments, the present invention relates to the aforementioned compound, wherein n is 1; $R^2$, $R^3$, and $R^6$ are H; $R^4$ and $R^5$ are —OC(O)$R^{10}$; and $R^{10}$ represents independently for each occurrence $(C_{11}-C_{15})$alkyl or $(C_{16}-C_{20})$alkyl.

In certain embodiments, the present invention relates to the aforementioned compound, wherein n is 1; $R^2$, $R^3$, and $R^6$ are H; $R^4$ and $R^5$ are —OC(O)$R^{10}$; $R^{10}$ represents independently for each occurrence $(C_{11}-C_{15})$alkyl or $(C_{16}-C_{20})$alkyl; and $R^7$ is

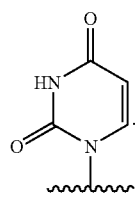

In certain embodiments, the present invention relates to the aforementioned compound, wherein n is 1; $R^2$, $R^3$, and $R^6$ are H; $R^4$ and $R^5$ are —OC(O)$R^{10}$; $R^{10}$ represents independently for each occurrence $(C_{11}-C_{15})$alkyl or $(C_{16}-C_{20})$alkyl; $R^7$ is

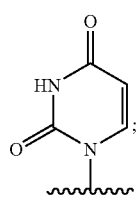

$R^1$ is

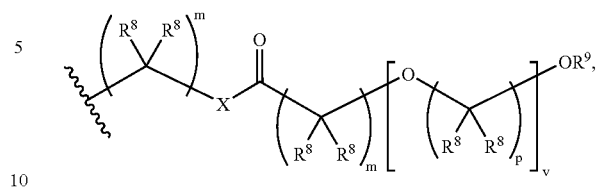

X is O, $R^8$ is H, $R^9$ is alkyl, m is 1, p is 2, and v is 12, 13, 14, 15, 16, 17, 18, 19, or 20.

In certain embodiments, the present invention relates to the aforementioned compound, wherein n is 1; $R^2$, $R^3$, and $R^6$ are H; $R^4$ and $R^5$ are —OC(O)$R^{10}$; $R^{10}$ represents independently for each occurrence $(C_{11}-C_{15})$alkyl or $(C_{16}-C_{20})$alkyl; $R^7$ is

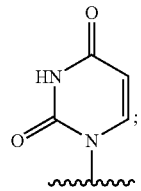

$R^1$ is

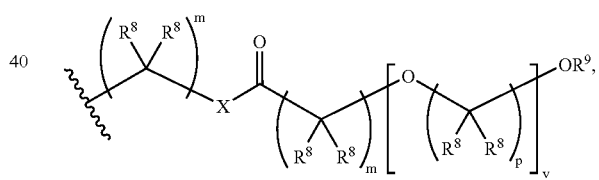

X is O; $R^8$ is H; m is 1; p is 2; v is 12, 13, 14, 15, 16, 17, 18, 19, or 20; and $R^9$ is represented by formula Ia:

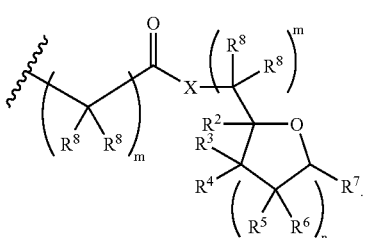

In certain embodiments, the present invention relates to the aforementioned compound, wherein said compound of formula V is

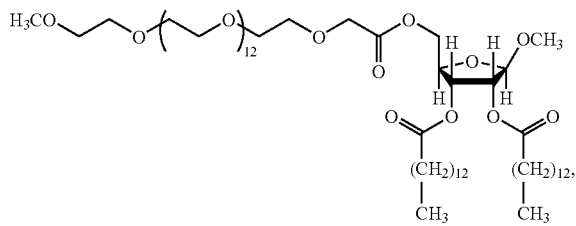
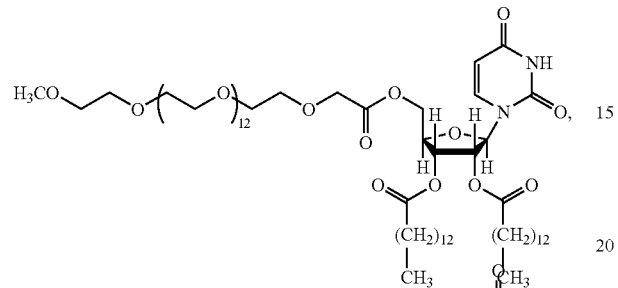
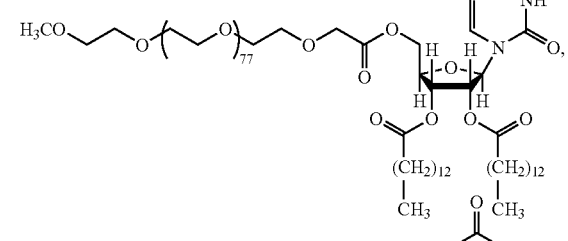
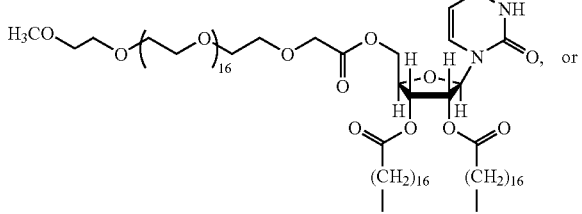
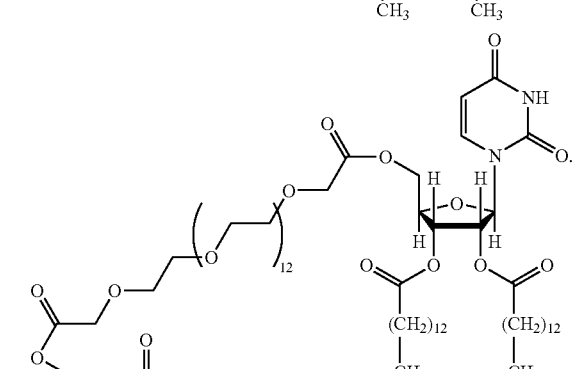
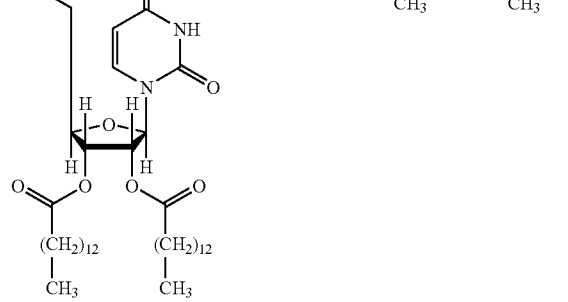

Another aspect of the present invention relates to a terpolymer of A, B, and C having a molecular weight of about 200 g/mol to about 1,000,000 g/mol; wherein A is represented by $CH_2=C(R_A)CO_2M$, wherein $R_A$ is $(C_1-C_5)$alkyl, and M is an alkali metal; B is represented by $CH_2=C(R_{1-B})CO_2R_{2-B}$, wherein $R_{1-B}$ is $(C_1-C_5)$alkyl, and $R_{2-B}$ is $(C_5-C_{25})$alkyl; and C is represented by:

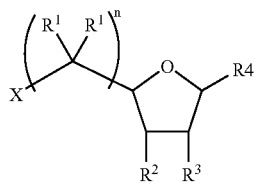

wherein $R^1$ is H, alkyl, or halogen;

$R^2$ and $R^3$ represent independently H, halogen, alkyl, alkoxyl, hydroxyl, $-N(R^5)_2$, or $R^6$;

$R^4$ is

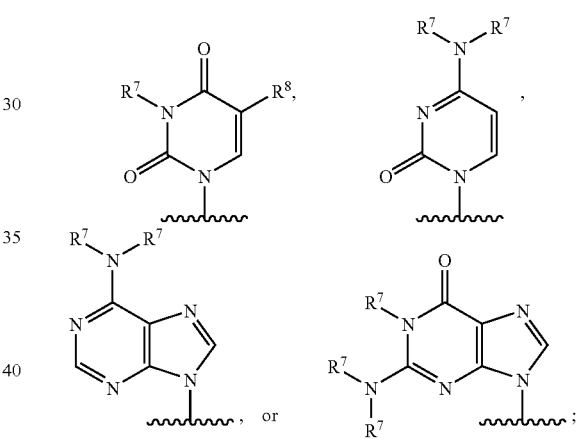

$R^5$ is H, alkyl, aryl, or aralkyl;

$R^6$ is $-OC(O)C(R^9)=CH_2$;

$R^7$ and $R^8$ represent independently for each occurrence H or alkyl;

$R^9$ is H or $(C_1-C_5)$alkyl;

$R^{10}$ is alkyl, aryl, aralkyl, $-Si(R^{11})_3$, $-C(O)R^{11}$, or $-C(O)N(R^{11})R^5$;

$R^{11}$ is alkyl, aryl, or aralkyl;

X is $-OR^{10}$ or $-N(R^{10})R^5$;

n is 1, 2, 3, or 4; and provided that one of $R^2$ and $R^3$ is $R^6$, but not both.

In certain embodiments, the present invention relates to the aforementioned compound, wherein the molecular weight of the polymer is about 10,000 g/mol to about 250,000 g/mol.

In certain embodiments, the present invention relates to the aforementioned compound, wherein the molecular weight of the polymer is about 15,000 g/mol to about 100,000 g/mol.

In certain embodiments, the present invention relates to the aforementioned compound, wherein the molecular weight of the polymer is about 20,000 g/mol to about 80,000 g/mol.

In certain embodiments, the present invention relates to the aforementioned compound, wherein the molecular weight of the polymer is about 30,000 g/mol to about 50,000 g/mol.

In certain embodiments, the present invention relates to the aforementioned compound, wherein the molecular weight of the polymer is about 35,000 g/mol to about 45,000 g/mol.

In certain embodiments, the present invention relates to the aforementioned compound, wherein C comprises about 5% to about 70% of the monomer units.

In certain embodiments, the present invention relates to the aforementioned compound, wherein C comprises about 5% to about 50% of the monomer units.

In certain embodiments, the present invention relates to the aforementioned compound, wherein C comprises about 10% to about 40% of the monomer units.

In certain embodiments, the present invention relates to the aforementioned compound, wherein C comprises about 20% to about 30% of the monomer units.

In certain embodiments, the present invention relates to the aforementioned compound, wherein A comprises about 30% to about 85% of the monomer units.

In certain embodiments, the present invention relates to the aforementioned compound, wherein A comprises about 40% to about 75% of the monomer units.

In certain embodiments, the present invention relates to the aforementioned compound, wherein A comprises about 55% to about 65% of the monomer units.

In certain embodiments, the present invention relates to the aforementioned compound, wherein A comprises about 55% to about 65% of the monomer units, and C comprises about 20 to about 40% of the monomer units.

In certain embodiments, the present invention relates to the aforementioned compound, wherein $R^4$ is

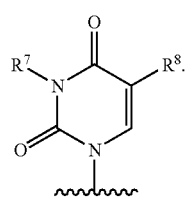

In certain embodiments, the present invention relates to the aforementioned compound, wherein $R^4$ is

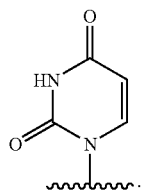

In certain embodiments, the present invention relates to the aforementioned compound, wherein C is

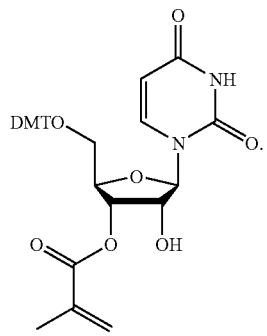

In certain embodiments, the present invention relates to the aforementioned compound, wherein A is $CH_2$=$CHCO_2M$.

In certain embodiments, the present invention relates to the aforementioned compound, wherein A is $CH_2$=$CHCO_2Na$.

In certain embodiments, the present invention relates to the aforementioned compound, wherein B is $CH_2$=$CHCO_2(C_8$-$C_{15})$alkyl.

In certain embodiments, the present invention relates to the aforementioned compound, wherein B is $CH_2$=$CHCO_2(C_{10})$alkyl.

In certain embodiments, the present invention relates to the aforementioned compound, wherein A is $CH_2$=$CHCO_2Na$, B is $CH_2$=$CHCO_2(C_{10})$alkyl, and C is

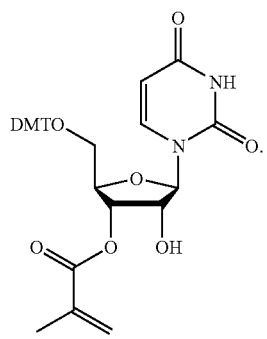

Another aspect of the present invention relates to a copolymer of lysine derivative D and alkyl ester E, wherein said copolymer has a molecular weight of about 200 g/mol to about 1,000,000 g/mol, D is represented by:

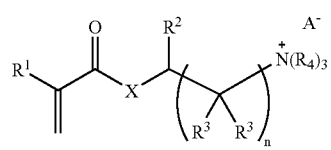

wherein
X is O or —$N(R^5)$—;
$R^1$ is H or $(C_1$-$C_5)$alkyl;
$R^2$ is —$C(O)R^6$, —$CO_2R^6$, or —$C(O)N(R^7)_2$;
$R^3$ is H, alkyl, or halogen;
$R^4$ and $R^5$ represent independently for each occurrence H, alkyl, aryl, or aralkyl;

$R^6$ represents independently for each occurrence alkyl, aryl, or aralkyl;

$R^7$ represents independently for each occurrence H, alkyl, aryl, or aralkyl;

A is an anion with a net charge of negative 1; and n is 1, 2, 3, 4, 5, 6, 7, or 8; and E is represented by:

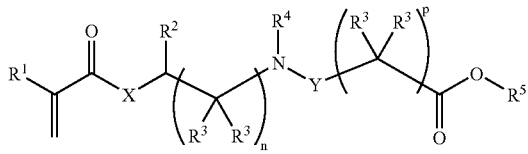

wherein

X is O or —N($R^6$)—;

Y is —C(O)— or —C($R^3$)$_2$—;

$R^1$ is H or ($C_1$-$C_5$)alkyl;

$R^2$ is —C(O)$R^7$, —CO$_2R^7$, or —C(O)N($R^8$)$_2$;

$R^3$ is H, alkyl, or halogen;

$R^4$ and $R^6$ represent independently for each occurrence H, alkyl, aryl, or aralkyl;

$R^5$ is alkyl, aryl, or aralkyl;

$R^7$ represents independently for each occurrence alkyl, aryl, or aralkyl;

$R^8$ represents independently for each occurrence H, alkyl, aryl, or aralkyl;

n is 1, 2, 3, 4, 5, 6, 7, or 8; and p is 6, 7, 8, 9, 10, 11, 12, 13, 14, or 15.

In certain embodiments, the present invention relates to the aforementioned compound, wherein A is halogen or $R_{12}CO_2^-$, wherein $R_{12}$ is alkyl, aryl, or aralkyl.

In certain embodiments, the present invention relates to the aforementioned compound, wherein the molecular weight of the polymer is about 10,000 g/mol to about 250,000 g/mol.

In certain embodiments, the present invention relates to the aforementioned compound, wherein the molecular weight of the polymer is about 15,000 g/mol to about 100,000 g/mol.

In certain embodiments, the present invention relates to the aforementioned compound, wherein the molecular weight of the polymer is about 20,000 g/mol to about 80,000 g/mol.

In certain embodiments, the present invention relates to the aforementioned compound, wherein the molecular weight of the polymer is about 30,000 g/mol to about 50,000 g/mol.

In certain embodiments, the present invention relates to the aforementioned compound, wherein the molecular weight of the polymer is about 35,000 g/mol to about 45,000 g/mol.

In certain embodiments, the present invention relates to the aforementioned compound, wherein E comprises greater than about 45% of the monomer units.

In certain embodiments, the present invention relates to the aforementioned compound, wherein E comprises greater than about 55% of the monomer units.

In certain embodiments, the present invention relates to the aforementioned compound, wherein E comprises greater than about 65% of the monomer units.

In certain embodiments, the present invention relates to the aforementioned compound, wherein E comprises greater than about 75% of the monomer units.

In certain embodiments, the present invention relates to the aforementioned compound, wherein E comprises greater than about 85% of the monomer units.

In certain embodiments, the present invention relates to the aforementioned compound, wherein D comprises about 100% of the monomer units.

In certain embodiments, the present invention relates to the aforementioned compound, wherein D is represented by

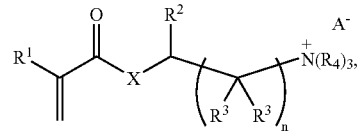

wherein X is —N($R^5$)—, $R^1$ is methyl, $R^2$ is —CO$_2R^6$, $R^3$ is H; $R^4$ and $R^5$ are H, $R^6$ is ($C_1$-$C_6$)alkyl, A is halogen, and n is 3, 4, or 5.

In certain embodiments, the present invention relates to the aforementioned compound, wherein D is

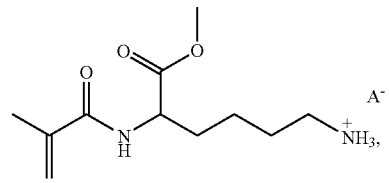

and A is halogen.

In certain embodiments, the present invention relates to the aforementioned compound, wherein D is

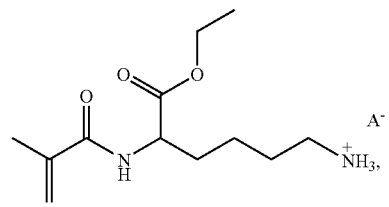

and A is halogen.

In certain embodiments, the present invention relates to the aforementioned compound, wherein E is represented by

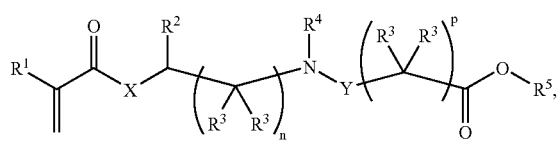

wherein X is —N($R^6$)—, Y is —C(O)—, $R^1$ is methyl, $R^2$ is —CO$_2R^7$, $R^3$ is H, $R^4$ and $R^6$ are H, $R^5$ is aralkyl, $R^7$ is ($C_1$-$C_6$)alkyl, n is 3, 4, or 5, and p is 9, 10, or 11.

In certain embodiments, the present invention relates to the aforementioned compound, wherein E is

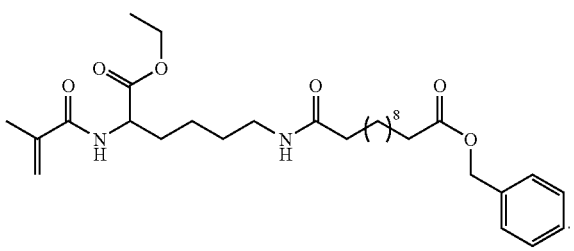

In certain embodiments, the present invention relates to the aforementioned compound, wherein D is represented by

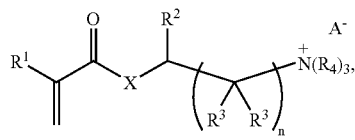

wherein X is —N(R$^5$)—, R$^1$ is methyl, R$^2$ is —CO$_2$R$^6$, R$^3$ is H; R$^4$ and R$^5$ are H, R$^6$ is (C$_1$-C$_6$)alkyl, A is halogen, and n is 3, 4, or 5; and E is represented by

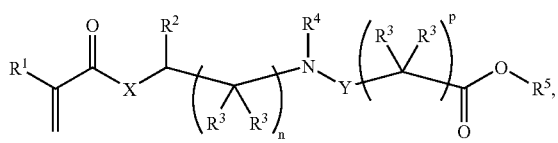

wherein X is —N(R$^6$)—, Y is —C(O)—, R$^1$ is methyl, R$^2$ is —CO$_2$R$^7$, R$^3$ is H, R$^4$ and R$^6$ are H, R$^5$ is aralkyl, R$^7$ is (C$_1$-C$_6$)alkyl, n is 3, 4, or 5, and p is 9, 10, or 11.

In certain embodiments, the present invention relates to the aforementioned compound, wherein D is

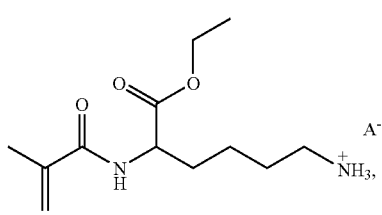

A is halogen, and E is

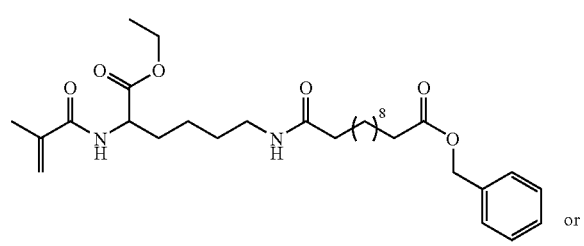

or

-continued

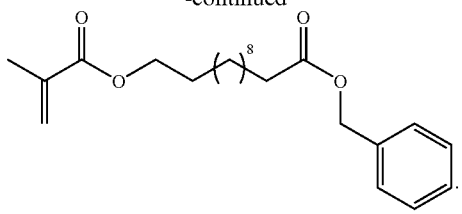

Another aspect of the present invention relates to a pharmaceutical composition comprising a compound of formula I, II, III, or IV; a terpolymer of A, B, and C; or a copolymer of lysine derivative D and alkyl ester E and a nucleic acid.

In certain embodiments, the present invention relates to the aforementioned method, wherein said nucleic acid is DNA, RNA, plasmid, siRNA, duplex oligonucleotide, single-strand oligonucleotide, triplex oligonucleotide, PNA, or mRNA.

In certain embodiments, the present invention relates to the aforementioned method, wherein said nucleic acid consists of about 10 to about 5000 nucleotides.

In certain embodiments, the present invention relates to the aforementioned method, wherein said nucleic acid is DNA or RNA.

In certain embodiments, the present invention relates to the aforementioned method, wherein said nucleic acid is a DNA or RNA sequence related to a medical disease.

In certain embodiments, the present invention relates to the aforementioned method, wherein said nucleic acid is DNA.

In certain embodiments, the present invention relates to the aforementioned method, wherein said nucleic acid is a DNA or RNA sequence targeting a retroviral gene, viral gene, drug resistance gene, oncogene, gene related to inflammatory response, cellular adhesion gene, hormone gene, abnormally overexpressed genes involved in gene regulation.

In certain embodiments, the present invention relates to the aforementioned method, wherein said nucleic acid is a DNA or RNA sequence related to cancer, viral infection, bacterial infection, lysosomal storage disorder, hypertension, ischaemic disorder, or HIV.

In certain embodiments, the present invention relates to the aforementioned method, wherein said nucleic acid is a DNA sequence encoding a genetic marker selected from the group consisting of luciferase gene, beta.-galactosidase gene, hygromycin resistance, neomycin resistance, and chloramphenicol acetyl transferase.

In certain embodiments, the present invention relates to the aforementioned method, wherein said nucleic acid is DNA sequence encoding protein selected from the group consisting of low density lipoprotein receptors, coagulation factors, gene suppressors of tumors, major histocompatibility proteins, antioncogenes, p16, p53, thymidine kinase, IL2, IL 4, and TNFa.

In certain embodiments, the present invention relates to the aforementioned method, wherein said nucleic acid is a DNA sequence encoding viral antigen.

In certain embodiments, the present invention relates to the aforementioned method, wherein said nucleic acid is a DNA sequence encoding an RNA selected from the group consisting of a sense RNA, an antisense RNA, and a ribozyme.

In certain embodiments, the present invention relates to the aforementioned method, wherein said nucleic acid is a DNA sequence encoding lectin, a mannose receptor, a sialoadhesin, or a retroviral transactivating factor.

In certain embodiments, the present invention relates to the aforementioned method, wherein said pharmaceutical composition further comprises DPPC, DMPC, PEGylated DPPC, DPPC, DOPE, DLPC, DMPC, DPPC, DSPC, DOPC, DMPE, DOPE, DPPE, DMPA-Na, DMRPC, DLRPC, DARPC, or similar catonic, anionic, or zwitterionic amphiphiles, fatty acids, cholesterol, flourescencetly labeled phospholipids, ether lipids, or sphingolipids.

Another aspect of the present invention relates to a pharmaceutical composition comprising a compound of formula V, a solid surface, and a nucleic acid.

In certain embodiments, the present invention relates to the aforementioned method, wherein said surface is mica, glass, polymer, metal, metal alloy, ceramic, or oxide.

In certain embodiments, the present invention relates to the aforementioned method, wherein said surface is mica.

In certain embodiments, the present invention relates to the aforementioned method, wherein said nucleic acid is DNA, RNA, plasmid, siRNA, duplex oligonucleotide, single-strand oligonucleotide, triplex oligonucleotide, PNA, or mRNA.

In certain embodiments, the present invention relates to the aforementioned method, wherein said nucleic acid consists of about 10 to about 5000 nucleotides.

In certain embodiments, the present invention relates to the aforementioned method, wherein said nucleic acid is DNA or RNA.

In certain embodiments, the present invention relates to the aforementioned method, wherein said nucleic acid is a DNA or RNA sequence related to a medical disease.

In certain embodiments, the present invention relates to the aforementioned method, wherein said nucleic acid is DNA.

In certain embodiments, the present invention relates to the aforementioned method, wherein said nucleic acid is a DNA or RNA sequence targeting a retroviral gene, viral gene, drug resistance gene, oncogene, gene related to inflammatory response, cellular adhesion gene, hormone gene, abnormally overexpressed genes involved in gene regulation.

In certain embodiments, the present invention relates to the aforementioned method, wherein said nucleic acid is a DNA or RNA sequence related to cancer, viral infection, bacterial infection, lysosomal storage disorder, hypertension, ischaemic disorder, or HIV.

In certain embodiments, the present invention relates to the aforementioned method, wherein said nucleic acid is a DNA sequence encoding a genetic marker selected from the group consisting of luciferase gene, beta.-galactosidase gene, hygromycin resistance, neomycin resistance, and chloramphenicol acetyl transferase.

In certain embodiments, the present invention relates to the aforementioned method, wherein said nucleic acid is DNA sequence encoding protein selected from the group consisting of low density lipoprotein receptors, coagulation factors, gene suppressors of tumors, major histocompatibility proteins, antioncogenes, p16, p53, thymidine kinase, IL2, IL 4, and TNFa.

In certain embodiments, the present invention relates to the aforementioned method, wherein said nucleic acid is a DNA sequence encoding viral antigen.

In certain embodiments, the present invention relates to the aforementioned method, wherein said nucleic acid is a DNA sequence encoding an RNA selected from the group consisting of a sense RNA, an antisense RNA, and a ribozyme.

In certain embodiments, the present invention relates to the aforementioned method, wherein said nucleic acid is a DNA sequence encoding lectin, a mannose receptor, a sialoadhesin, or a retroviral transactivating factor.

In certain embodiments, the present invention relates to the aforementioned method, wherein said pharmaceutical composition further comprises DPPC, DMPC, PEGylated DPPC, DPPC, DOPE, DLPC, DMPC, DPPC, DSPC, DOPC, DMPE, DOPE, DPPE, DMPA-Na, DMRPC, DLRPC, DARPC, or similar catonic, anionic, or zwitterionic amphiphiles, fatty acids, cholesterol, flourescencetly labeled phospholipids, ether lipids, or sphingolipids.

Methods of the Invention

One aspect of the present invention relates to a method of delivering a nucleic acid to a cell, comprising the step of:

contacting a cell with an effective amount of a mixture comprising a nucleic acid to be delivered to said cell and a compound of formula I, II, III, or IV; a terpolymer of A, B, and C; or a copolymer of lysine derivative D and alkyl ester E.

In certain embodiments, the present invention relates to the aforementioned method, wherein said nucleic acid is DNA, RNA, plasmid, siRNA, duplex oligonucleotide, single-strand oligonucleotide, triplex oligonucleotide, PNA, or mRNA.

In certain embodiments, the present invention relates to the aforementioned method, wherein said nucleic acid consists of about 10 to about 5000 nucleotides.

In certain embodiments, the present invention relates to the aforementioned method, wherein said nucleic acid is DNA or RNA.

In certain embodiments, the present invention relates to the aforementioned method, wherein said nucleic acid is a DNA or RNA sequence related to a medical disease.

In certain embodiments, the present invention relates to the aforementioned method, wherein said nucleic acid is DNA.

In certain embodiments, the present invention relates to the aforementioned method, wherein said nucleic acid is a DNA or RNA sequence targeting a retroviral gene, viral gene, drug resistance gene, oncogene, gene related to inflammatory response, cellular adhesion gene, hormone gene, abnormally overexpressed genes involved in gene regulation.

In certain embodiments, the present invention relates to the aforementioned method, wherein said nucleic acid is a DNA or RNA sequence related to cancer, viral infection, bacterial infection, lysosomal storage disorder, hypertension, ischaemic disorder, or HIV.

In certain embodiments, the present invention relates to the aforementioned method, wherein said nucleic acid is a DNA sequence encoding a genetic marker selected from the group consisting of luciferase gene, beta.-galactosidase gene, hygromycin resistance, neomycin resistance, and chloramphenicol acetyl transferase.

In certain embodiments, the present invention relates to the aforementioned method, wherein said nucleic acid is DNA sequence encoding protein selected from the group consisting of low density lipoprotein receptors, coagulation factors, gene suppressors of tumors, major histocompatibility proteins, antioncogenes, p16, p53, thymidine kinase, IL2, IL 4, and TNFa.

In certain embodiments, the present invention relates to the aforementioned method, wherein said nucleic acid is a DNA sequence encoding viral antigen.

In certain embodiments, the present invention relates to the aforementioned method, wherein said nucleic acid is a DNA sequence encoding an RNA selected from the group consisting of a sense RNA, an antisense RNA, and a ribozyme.

In certain embodiments, the present invention relates to the aforementioned method, wherein said nucleic acid is a DNA sequence encoding lectin, a mannose receptor, a sialoadhesin, or a retroviral transactivating factor.

In certain embodiments, the present invention relates to the aforementioned method, wherein said cell is a animal cell or plant cell.

In certain embodiments, the present invention relates to the aforementioned method, wherein said cell is a mammalian cell.

In certain embodiments, the present invention relates to the aforementioned method, wherein said cell is a human cell or insect cell.

In certain embodiments, the present invention relates to the aforementioned method, wherein said cell is a human cell.

In certain embodiments, the present invention relates to the aforementioned method, wherein said cell is an embryonic cell or stem cell.

In certain embodiments, the present invention relates to the aforementioned method, wherein said cell is contacted in vivo, in vitro, or ex vivo.

In certain embodiments, the present invention relates to the aforementioned method, wherein said cell is contacted in vivo.

Another aspect of the present invention relates to a method of delivering a nucleic acid to a cell, comprising the step of:

contacting a cell with an effective amount of a mixture comprising a nucleic acid to be delivered to said cell and a compound of formula V in the presence of a solid surface.

In certain embodiments, the present invention relates to the aforementioned method, wherein said surface is mica, glass, polymer, metal, metal alloy, ceramic, or oxide.

In certain embodiments, the present invention relates to the aforementioned method, wherein said surface is mica.

In certain embodiments, the present invention relates to the aforementioned method, wherein said nucleic acid is DNA, RNA, plasmid, siRNA, duplex oligonucleotide, single-strand oligonucleotide, triplex oligonucleotide, PNA, or mRNA.

In certain embodiments, the present invention relates to the aforementioned method, wherein said nucleic acid consists of about 10 to about 5000 nucleotides.

In certain embodiments, the present invention relates to the aforementioned method, wherein said nucleic acid is DNA or RNA.

In certain embodiments, the present invention relates to the aforementioned method, wherein said nucleic acid is a DNA or RNA sequence related to a medical disease.

In certain embodiments, the present invention relates to the aforementioned method, wherein said nucleic acid is DNA.

In certain embodiments, the present invention relates to the aforementioned method, wherein said nucleic acid is a DNA or RNA sequence targeting a retroviral gene, viral gene, drug resistance gene, oncogene, gene related to inflammatory response, cellular adhesion gene, hormone gene, abnormally overexpressed genes involved in gene regulation.

In certain embodiments, the present invention relates to the aforementioned method, wherein said nucleic acid is a DNA or RNA sequence related to cancer, viral infection, bacterial infection, lysosomal storage disorder, hypertension, ischaemic disorder, or HIV.

In certain embodiments, the present invention relates to the aforementioned method, wherein said nucleic acid is a DNA sequence encoding a genetic marker selected from the group consisting of luciferase gene, beta.-galactosidase gene, hygromycin resistance, neomycin resistance, and chloramphenicol acetyl transferase.

In certain embodiments, the present invention relates to the aforementioned method, wherein said nucleic acid is DNA sequence encoding protein selected from the group consisting of low density lipoprotein receptors, coagulation factors, gene suppressors of tumors, major histocompatibility proteins, antioncogenes, p16, p53, thymidine kinase, IL2, IL 4, and TNFa.

In certain embodiments, the present invention relates to the aforementioned method, wherein said nucleic acid is a DNA sequence encoding viral antigen.

In certain embodiments, the present invention relates to the aforementioned method, wherein said nucleic acid is a DNA sequence encoding an RNA selected from the group consisting of a sense RNA, an antisense RNA, and a ribozyme.

In certain embodiments, the present invention relates to the aforementioned method, wherein said nucleic acid is a DNA sequence encoding lectin, a mannose receptor, a sialoadhesin, or a retroviral transactivating factor.

In certain embodiments, the present invention relates to the aforementioned method, wherein said cell is a animal cell or plant cell.

In certain embodiments, the present invention relates to the aforementioned method, wherein said cell is a mammalian cell.

In certain embodiments, the present invention relates to the aforementioned method, wherein said cell is human cell or insect cell.

In certain embodiments, the present invention relates to the aforementioned method, wherein said cell is human cell.

In certain embodiments, the present invention relates to the aforementioned method, wherein said cell is an embryonic cell or stem cell.

Definitions

For convenience, certain terms employed in the specification, examples, and appended claims are collected here.

The term "nucleic acids" means any double strand or single strand deoxyribonucleic acid (DNA) or ribonucleic acid (RNA) of variable length. Nucleic acids include sense and anti-sense strands. Nucleic acid analogs such as phosphorothioates, phosphoramidates, phosphonates analogs are also considered nucleic acids as that terms is used herein. Peptide nucleic acids and other synthetic analogs of nucleic acids which have therapeutic value are also included. Nucleic acids also include chromosomes and chromosomal fragments.

The term "liposome" as used herein refers to a closed structure comprising of an outer lipid bi- or multi-layer membrane surrounding an internal aqueous space. Liposomes can be, used to package any biologically active agent for delivery to cells. For example, DNA can be packaged into liposomes even in the case of plasmids or viral vectors of large size. Such liposome encapsulated DNA is ideally suited for use both in vitro, ex vivo, and in vivo. Liposomes generally from a bilayer membrane. These liposomes may form hexagonal structures, and suspension of multilamellar vesicles.

The term "transfection" describes the process by which foreign genes ("transgenes") are introduced into a living host cell. Host cells that express or incorporate the foreign DNA are known as "transformed cells," and the process by which they become transformed is called "transformation" or "transduction." Different types of cells vary in their susceptibility to transformation, and protocols for introducing the foreign DNA are typically optimized.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

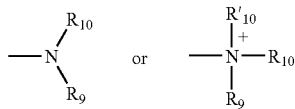

wherein $R_9$, $R_{10}$ and $R'_{10}$ each independently represent a group permitted by the rules of valence.

The term "acylamino" is art-recognized and refers to a moiety that can be represented by the general formula:

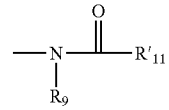

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

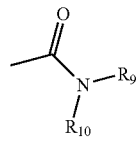

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

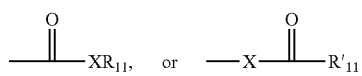

wherein X is a bond or represents an oxygen or a sulfur, and $R_{11}$ represents a hydrogen, an alkyl, an alkenyl, $-(CH_2)_m-R_8$ or a pharmaceutically acceptable salt, $R'_{11}$ represents a hydrogen, an alkyl, an alkenyl or $-(CH_2)_m-R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m-R_8$, where m and $R_8$ are described above.

The term "sulfonate" is art recognized and includes a moiety that can be represented by the general formula:

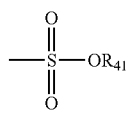

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

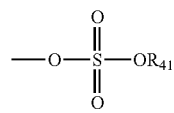

in which $R_{41}$ is as defined above.

The term "sulfonylamino" is art recognized and includes a moiety that can be represented by the general formula:

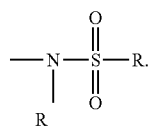

The term "sulfamoyl" is art-recognized and includes a moiety that can be represented by the general formula:

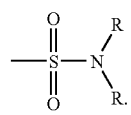

The term "sulfonyl", as used herein, refers to a moiety that can be represented by the general formula:

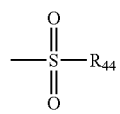

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

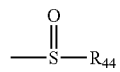

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m-R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and traits-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

The term "alkali metal" refer to those elements listed in Group 1 of the periodic table. The following elements are alkali metals: Li, Na, K, Rb, Cs, and Fr.

For purposes of this invention, the chemical elements are identified in accordance with the Periodic Table of the Elements, CAS version, Handbook of Chemistry and Physics, 67th Ed., 1986-87, inside cover.

EXEMPLIFICATION

The invention now being generally described, it will be more readily understood by reference to the following examples, which are included merely for purposes of illustration of certain aspects and embodiments of the present invention, and are not intended to limit the invention.

Example 1

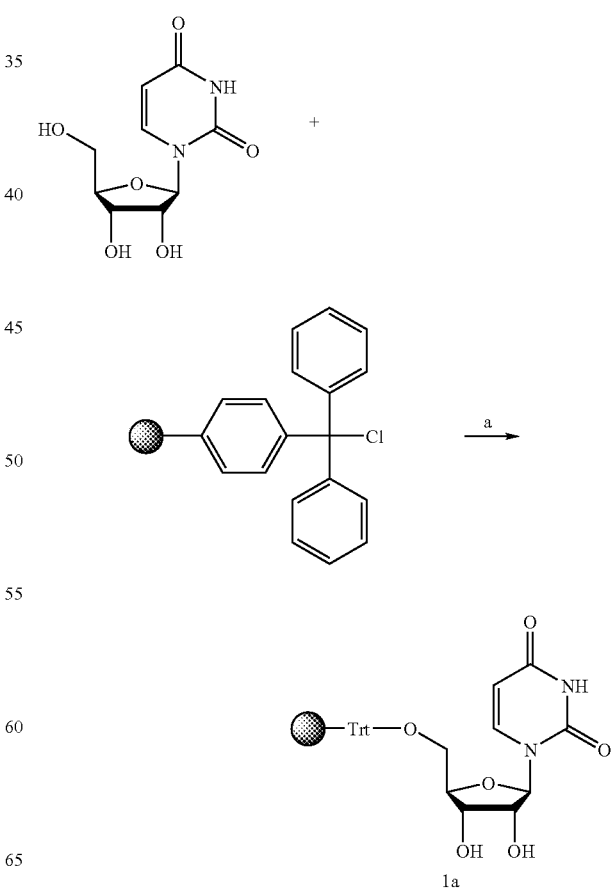

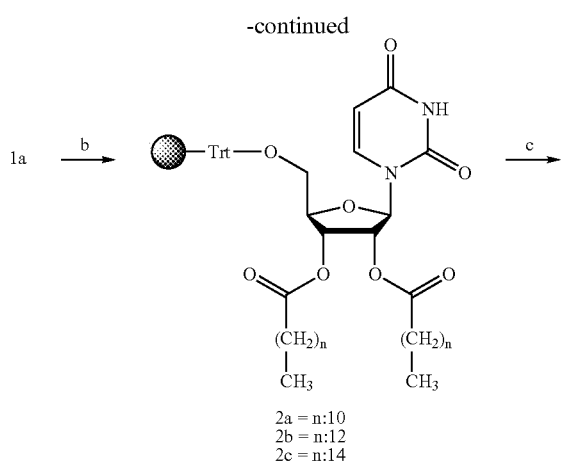

2a = n:10
2b = n:12
2c = n:14

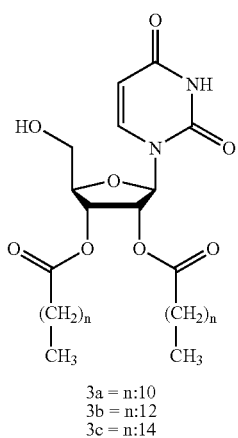

3a = n:10
3b = n:12
3c = n:14

Solid phase synthesis. a/ Chlorotrityl resin, DCM/pyridine 1/1, uridine, DMAP (cat), 5h, RT b/ RCO$_2$H, DCC, DMAP (cat) in DCM, 24h, RT c/ TFA/DCM 1/9, triethylsilane, 6h, RT Total yield (a, b, c): 18.5% (3a), 11% (3b), 45% (3c).

Resin Trityl Uridine (Compound 1a)

Trityl resin (1 g, 0.9 mM; 1 eq) was suspended in 40 mL of freshly distilled methylene chloride and pyridine (1/1). Uridine (0.330 g, 1.35 mM, 1.5 eq) and a catalytic amount of N,N-dimethyl aminopyridine were added to the reaction flask. After five hours at room temperature the resin is filtered off and washed three times with 20 mL of methylene chloride and dried under high vacuum. The characterization data were consistent with the proposed structure.

2',3'dimyristoyl uridine (Compound 3b)

Myristic acid (0.7 g, 3.06 mmol, 3.4 eq), dicyclohexylcarbodiimide (0.63 g, 3.06 mmol, 3.4 eq), and a catalytic amount of N,N-dimethyl aminopyridine were dissolved in dry methylene chloride. Resin 1a was then added to the reaction mixture. The suspension was shaken for 24 hours at room temperature. The resin was washed three times with 20 mL of methylene chloride and isolated by filtration under suction. The resulting dried beads were stirred with 20 mL of a trifluoroacetic acid/methylene chloride (1/9) mixture and triethylsilane (0.138 mL, 0.9 mmol, 1 eq). After 6 hours the resin was filtered off. The solvent was removed under vacuum. Product 3b (65 mg) was isolated after purification on silica gel (DCM/MeOH, 95/5). (Yield: 11%). The characterization data were consistent with the proposed structure.

2',3'dilauroyl uridine (Compound 3a)

A similar procedure was performed as for compound 3b. Lauric acid (0.24 g, 1.2 mmol, 3 eq), dicyclohexylcarbodiimide (0.24 g, 1.2 mmol; 3 eq), and a catalytic amount of N,N-dimethyl aminopyridine were dissolved in dry methylene chloride. Resin 1a (0.5 g) was added to the reaction mixture. Product 3a (45 mg) was isolated after purification on silica gel (DCM/MeOH, 95/5). (Yield: 18.5%). The characterization data were consistent with the proposed structure.

2',3'palmitoyl uridine (Compound 3c)

A similar procedure was followed as for compound 3b. Palmitic acid (0.31 g, 1.2 mmol, 3 eq), dicyclohexylcarbodiimide (0.24 g, 1.2 mmol, 3 eq), and N,N-dimethyl aminopyridine (0.069 g, 0.4 mmol, 1 eq) were dissolved in dry methylene chloride. Resin 1a (0.5 g, 0.4 mmol, 1 eq) was added to the reaction mixture. Product 3c (116 mg) were isolated after purification on silica gel (DCM/MeOH, 95/5). (Yield: 45%). The characterization data were consistent with the proposed structure.

Example 2

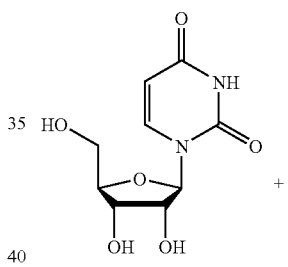

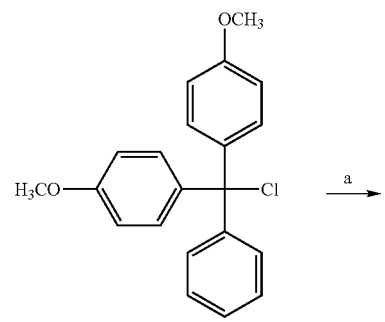

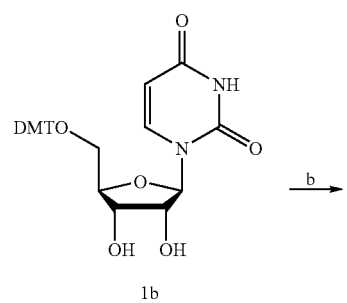

1b

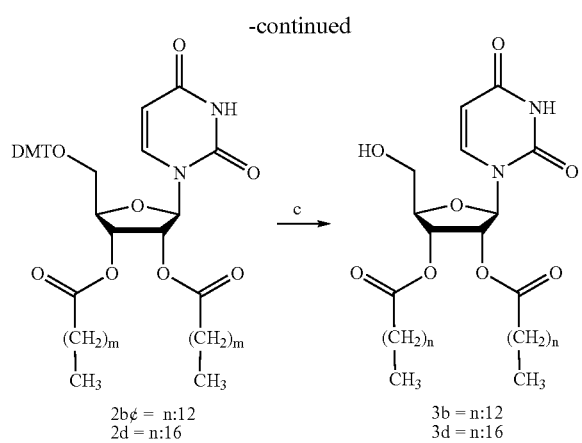

2b¢ = n:12
2d = n:16

3b = n:12
3d = n:16

FIG. 3 Liquid phase synthesis. a/ Dimethyoxytritylchloride, uridine, DMAP (cat) in pyridine, 24 h, RT, 87% yield b/ RCO$_2$H, DCC, DMAP in DMC, 2b¢ 90% yield. c/ CCl$_3$CO$_2$H 3% in DCM, 3b 87% yield, 3d (b, c) 58% yield). Total yield (a, b, c): 68% (3b), 51% (3d).

5'-O-(4,4'-dimethoxytrityl)uridine (Compound 1b)

Chlorodimethoxytrityl (2.0 g, 5.9 mmol, 1.3 eq), uridine (1.1 g, 4.5 mmol, 1 eq), and a catalytic amount of N,N-dimethyl aminopyridine were dissolved in 25 mL of pyridine. The reaction mixture was stirred for 24 hours at room temperature. Pyridine was removed under vacuum and the resulting crude material was purified on silicagel (DCM/MeOH 95/5) to yield 2.14 g of the expected product 1b. (Yield: 87.1%). The characterization data were consistent with the proposed structure.

5'-O-(4,4'-dimethoxytrityl)-2',3'-dimyristoyl uridine (Compound 2b')

Compound 1b (0.50 g, 0.91 mmol, 1 eq), myristic acid (0.46 g, 2.01 mmol, 2.2 eq), dicyclohexylcarbodiimide (0.41 g, 2.01 mmol, 2.2 eq), N,N-dimethylaminopyridine (0.24 g, 2.01 mmol, 2.2 eq) were dissolved in 100 mL of freshly distilled methylene chloride. The mixture was stirred for 24 hours at room temperature under nitrogen. After filtration, the organic phase was successively washed with 20 mL of water 3 times, dried over sodium sulfate. Methylene chloride was removed under vacuum. The product (0.79 g) is obtained after chromatography on silicagel (DCM/MeOH, 95/5). (Yield: 89.5%). The characterization data were consistent with the proposed structure.

2',3'dimyristoyl uridine (Compound 3b)

Compound 2b' (0.788 g, 0.81 mmol) was dissolved in 50 mL of dried methylene chloride and an excess of a 3% tricloroethylacetic acid in methylene chloride was added. After thirty minutes, 3 mL of methanol was added to the mixture. The organic layer was then washed three times with 20 mL of water and dried over sodium sulfate. Crystallization in methylene chloride provided 464 mg (0.70 mmol) of compound 3b. (Yield: 86.4%). (Total yield: 67.3%) The characterization data were consistent with the proposed structure.

2',3'-disteroyl uridine (Compound 3d)

Compound 1b (1.3 g, 2.46 mmol, 1 eq), stearic acid (2.37 g, 8.36 mmol, 3.4 eq), dicyclohexylcarbodiimide (1.71 g, 8.36 mmol, 3.4 eq), and N,N-dimethylaminopyridine (1 g, 8.36 mmol, 3.4 eq), are dissolved in 100 mL of freshly distilled methylene chloride. The mixture was stirred for 48 hours at room temperature under nitrogen. After filtration, the organic layer was washed with 20 mL of water 3 times and then dried over sodium sulfate. Methylene chloride is removed under vacuum. The residual crude product was dried under high vacuum for one hour. The resulting white powder was dissolved in 50 mL of freshly distilled methylene chloride and an excess of a 3% trichloroethylacetic acid in methylene chloride was added under nitrogen to the solution. After 15 minutes, 5 mL of methanol were poured into the solution. The organic phase was washed 3 times with 20 mL of water and then dried over sodium sulfate. Solvent was removed under vacuum and 1.1 g of product 3d were isolated after crystallization in methylene chloride. (Yield: 58%). The characterization data were consistent with the proposed structure.

Example 3

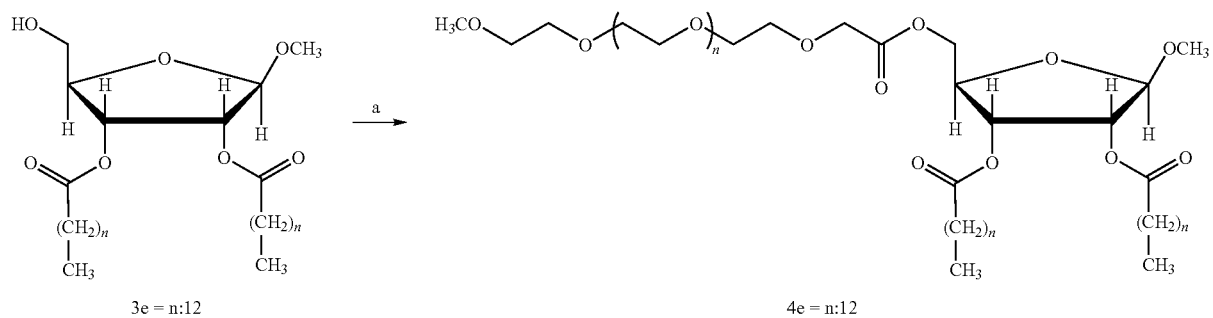

3e = n:12

4e = n:12

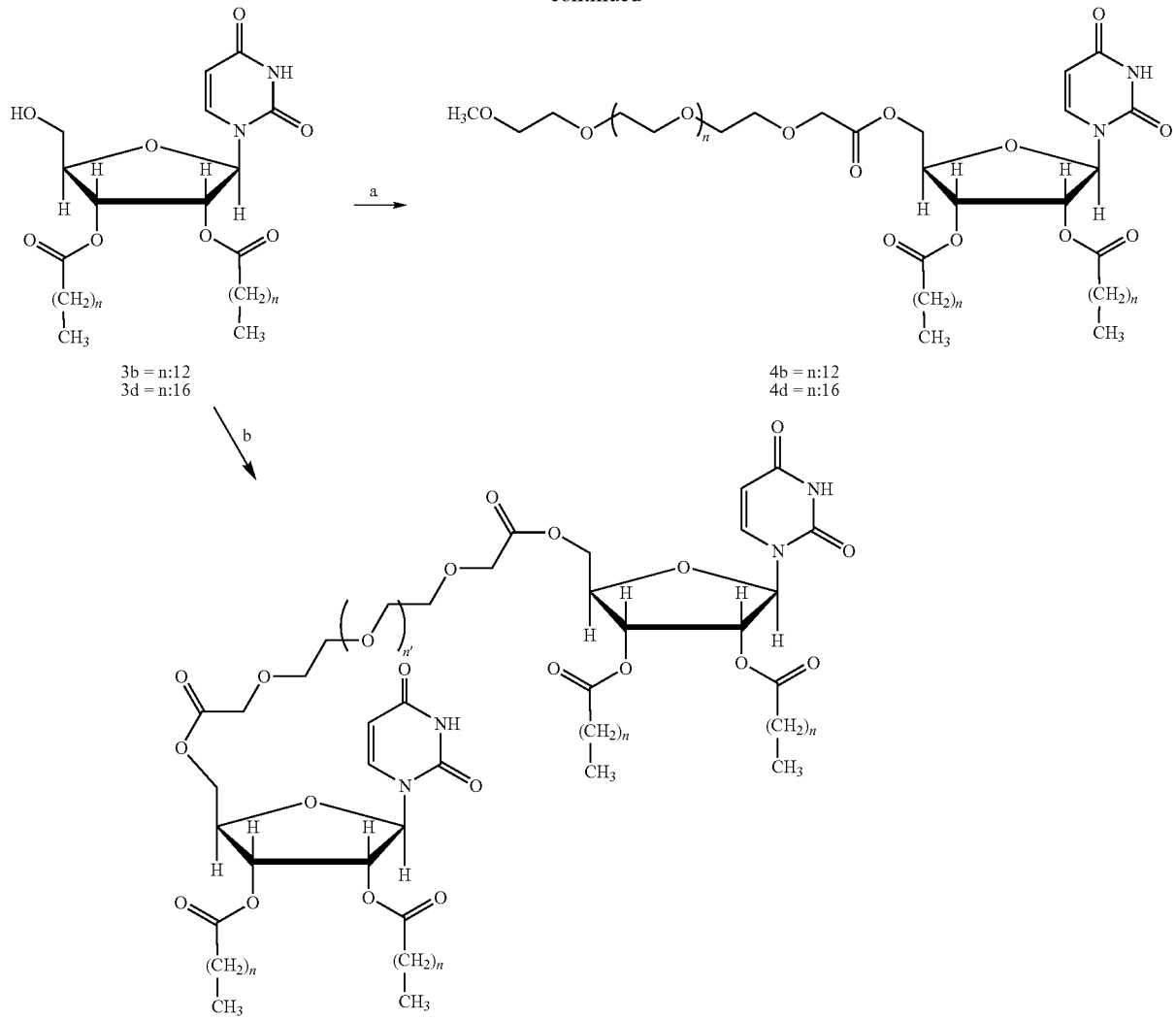

FIG. 4. Synthesis of the PEG derivatives. a/ CH₃O(PEG5000)CH₂CO₂H, DCC, DMAP in DCM, RT, 6 days, 4e 55% yield, 4b 64% yield, 4d 72% yield b/ HO₂CCH₂(PEG3400)CH₂CO₂H, DCC, DMAP in DCM, RT, 6 days, 4d 48% yield.

5'-PEG-2',3'-dimyristoyl uridine (Compound 4b)

Compound 3b (10 mg, 0.015 mmol, 1 eq), methoxy-PEG5000-carboxymethyl (75 mg 0.015 mmol, 1 eq), dicyclohexylcarbodiimide (10 mg, 0.05 mmol, 3.3 eq), and a catalytic amount of N,N-dimethylaminopyridine were dried for one hour under high vacuum. Then, the starting material was dissolved under nitrogen in 5 mL of freshly distilled methylene chloride. The mixture was stirred for 6 days at room temperature under nitrogen. After filtration, the solvent was removed and the resulting crude product was purified with a LH20 size exclusion column in DCM/MeOH 50/50. The product (56 mg) was isolated after precipitation in methanol/ether. (Yield: 64%). The characterization data were consistent with the proposed structure.

5'-PEG-2',3'-disteroyluridine (Compound 4d)

A similar procedure was followed as for product 4b. Compound 3d (50 mg, 0.064 mmol, 1 eq), methoxy-PEG5000-carboxymethyl (321 mg, 0.064 mmol; 1 eq), dicyclohexylcarbodiimide (20 mg, 0.097 mmol, 1.5 eq), and a catalytic amount of N,N-dimethylaminopyridine were dissolved in methylene chloride. A white powder was isolated (270 mg) after precipitation in methanol/ether and purification (LH20 size exclusion column in DCM/MeOH 50/50). (Yield: 72%). The characterization data were consistent with the proposed structure.

1-methoxy-2,3-dimiristoyl-5-PEG-ribose (Compound 4e)

A similar procedure was performed as for product 4b. Compound 3e (50 mg, 0.085 mmol, 1 eq), methoxy-PEG5000-carboxymethyl (428 mg, 0.085 mmol, 1 eq), dicyclohexylcarbodiimide (22 mg, 0.10 mmol, 1.25 eq), and a catalytic amount of N,N-dimethylaminopyridine were dissolved in methylene chloride. A white powder (261 mg) was isolated after precipitation in methanol/ether and purification (LH20 size exclusion column in DCM/MeOH 50/50). (Yield: 55%). The characterization data were consistent with the proposed structure.

Di-(5'-carboxymethyl-2',3'-dimiristoyluridine)-PEG—(Compound 5)

A similar procedure was followed as for product 4b. Compound 3b (41 mg, 0.062 mmol, 2.2 eq), PEG3400-(carboxymethyl)$_2$ (95 mg, 0.028 mmol, 1 eq), of dicyclohexylcarbodiimide (31 mg, 0.062 mmol, 2.2 eq), and a catalytic amount of N,N-dimethylaminopyridine were dissolved in methylene chloride. A white powder (64 mg) was isolated after precipitation in methanol/ether and purification (LH20 size exclusion column in DCM/MeOH 50/50). (Yield: 48%). The characterization data were consistent with the proposed structure.

Example 4

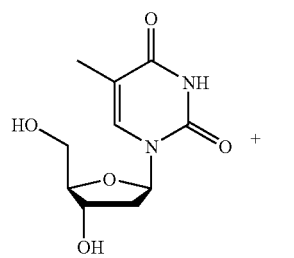

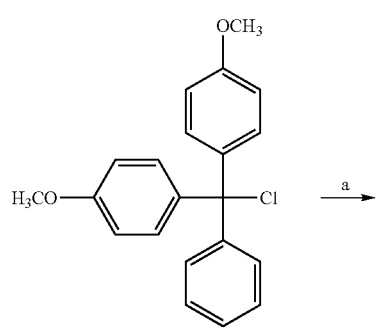

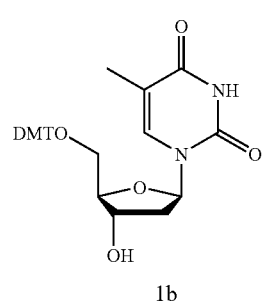

1b

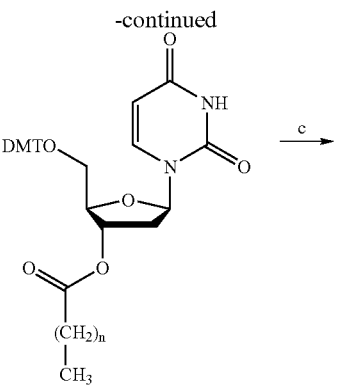

6 = n:12

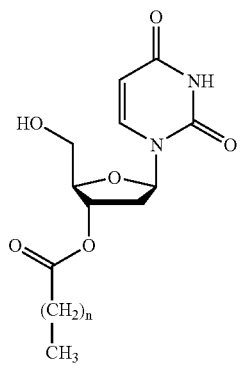

7 = n: 12

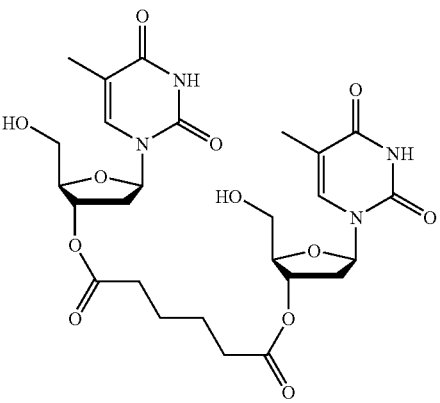

8 = n: 12

FIG. 5 Synthesis of thymidine derivatives. a/ 4,4'- Dimethoxytritylchloride, thymidine, DMAP (cat) in pyridine, 24 h, RT, 96% yield b/ RCO$_2$H, DCC, DMAP in DCM, 12 h, RT c/ CCl$_3$CO$_2$H 3% in DCM, 3g 75% yield (b, c); 3 h, 14% yield (b, c). Total yield (a, b, c): 68% (3g), 13% (3 h).

3'-myristoyl thymidine (Compound 7)

Compound 1b (360 mg, 0.66 mmol, 1 eq), myristic acid (226 mg, 0.99 mmol, 1.5 eq), dicyclohexylcarbodiimide (204 mg, 0.99 mmol, 1.5 eq), and N,N-dimethylaminopyridine (80 mg, 0.66 mmol, 1 eq) were dissolved in 100 ml of freshly distilled methylene chloride. The reaction mixture was stirred for 12 hours at room temperature under nitrogen. After filtration under vacuum, the organic phase was treated with an excess of 3% tricloroethylacetic acid in methylene chloride. After 15 minutes, 5 mL of methanol was added to the reaction. The expected product 3 g (225 mg) was obtained after chromatography on silicagel (DCM/MeOH, 95/5). (Yield: 75%). The characterization data were consistent with the proposed structure.

Adipoyl-1,6-di-3'thymidine (Compound 8)

Compound 1b (1 g, 4.08 mmol, 2.2 eq), adipic acid (0.271 g, 1.85 mmol, 1 eq), dicyclohexylcarbodiimide (0.84 g, 4.08 mmol, 2.2 eq), and N,N-dimethylaminopyridine (0.5 g, 4.08 mmol, 2.2 eq) were dissolved in 100 mL of freshly distilled methylene chloride. The reaction mixture was stirred for 24 hours at room temperature under nitrogen. After filtration, the mixture was treated with an excess of 3% trichloroethylacetic acid solution in methylene chloride. After 30 minutes, 5 mL of methanol was added to the reaction. The organic layer was washed 3 times with 10 mL of water and then dried over sodium sulfate. The expected product 3 g (150 mg) was obtained after chromatography on silicagel (DCM/MeOH, 95/5). (Yield: 14%). The characterization data were consistent with the proposed structure.

Example 5

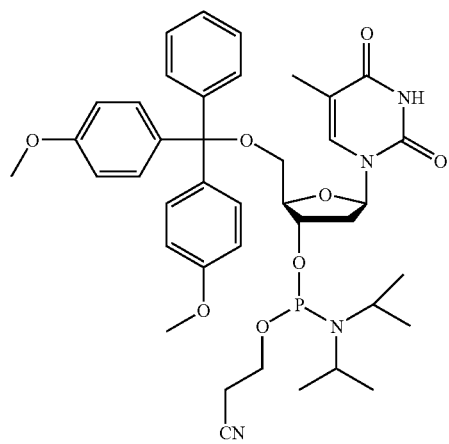

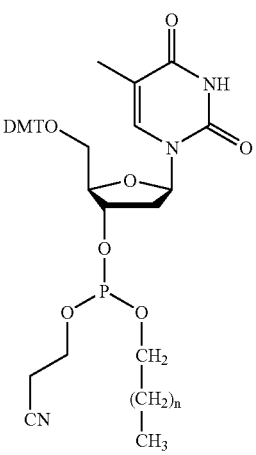

9a: n = 10
9b: n = 18

-continued

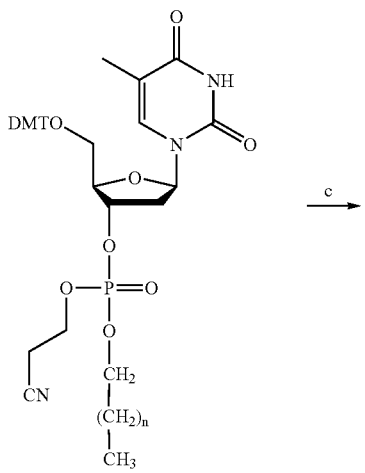

10a: n = 10
10b: n = 18

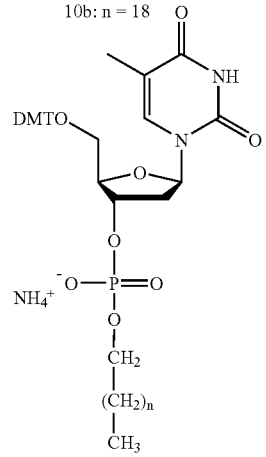

11a: n = 10
11b: n = 18

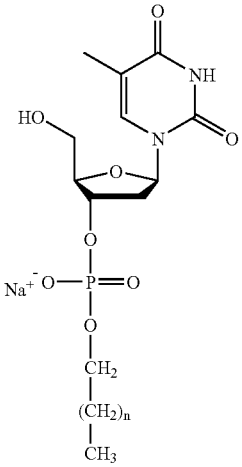

12a: n = 10
12b: n = 18

FIG. 6 Synthesis of phosphate derivatives, a/ tetrazole, in acetonitrile RT, $N_2$, 5 h b/ Oxidation 0.02 M $I_2$ in THF/Pyr/$H_2O$, rt, 12 h c/ $NH_4OH$ 30% in water, 60 C. 24 h d/ 1) $CCl_3CO_2H$ 3% in DCM, RT, 2 h 2) NaOH (0.1 N) in MeOH. Total yield (a, b, c, d) from 50 to 80%.

5'-(dimethoxytrityl)-2'-deoxythymidine,3'-(1-dodecyl)-ammonium-phosphate (Compound 11a)

5'-(4,4'-dimethoxytrityl)-2'-deoxythymidine,3'-[(2-cyanoethyl)-N,N-diisopropyl)]-phosphoramidite (1 g, 1.34 mmol, 1 eq), dodecanol (0.324 g, 1.74 mmol, 1.3 eq), and tetrazole (0.122 g, 1.74 mmol, 1.3 eq) were dissolved in dry acetonitrile under nitrogen. The reaction mixture was stirred for 5 h at room temperature. A 100 mL solution of 0.02M $I_2$ in THF/Pyr/$H_2O$ oxidized the resulting mixture. After 12 h at room temperature the solvent was removed under vacuum to yield compound $6_a$. To remove the cyanoethyl-protecting group to give compound 9a, the contents of the reaction flask were dissolved in 100 mL of $NH_4OH$ 30% in water and heated under stirring in a sealed tube for 24 hours. The phosphate derivative 9a (0.71 g) was isolated after purification on silicagel (MeOH/DCM 20/80). (Yield: 66%). The characterization data were consistent with the proposed structure.

2'-deoxthymidine,3'-(1-dodecyl)-sodium-phosphate (Compound 12a)

Phosphate 7a (0.447 g, 0.55 mmol, 1 eq), was dissolved in 50 mL of freshly distilled methylene chloride. An excess of 3% trichloroethylacetic acid solution in methylene chloride was added. After 2 h under nitrogen, 5 mL of MeOH are poured into the solution. The solvent was removed under vacuum and the residual oil was precipitated in ether. The acidic derivative (234 mg) was isolated after purification on a Sep Pak C18 cartridge (water, water/MeOH 50/50). The sodium salt was obtained by adding a NaOH solution (0.1N) to the acid dissolved in MeOH (pH was adjusted to 8.5). (Yield: 87%). The characterization data were consistent with the proposed structure.

Example 6

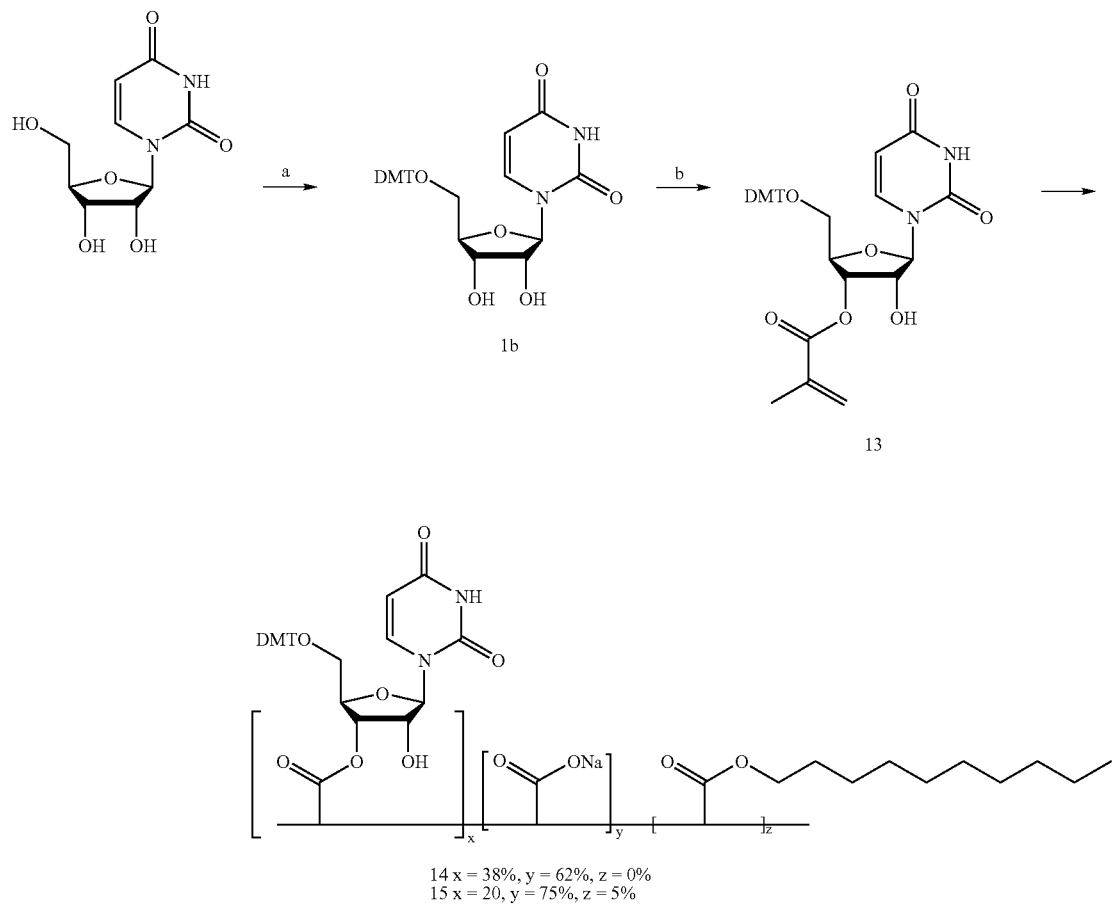

FIG. 7 Synthesis of polymers. a/ Methacryloyl chloride, TEA, DMAP in DCM, 15 min 0 C. then 1 h at RT. b/ $CCl_3CO_2H$ 3% in DCM, yield (a, b): 98%. c/ AIBN, MeOH, reflux, 24 h, conversion (9a): 40%, (9b): 79%.

3'-metacryloyl-thymidine (Compound 13)

Methacryloyl chloride (0.186 g) in 10 ml of methylene chloride was added dropwise under nitrogen to 1b (0.787 g, 1.44 mmol, 1 eq), triethylamine (0.176 g, 1.73 mmol, 1.2 eq), and a catalytic amount of N,N-dimethyl aminopyridine dissolved in 50 mL of dry methylene chloride at 0° C. The reaction mixture was stirred at 0° C. for 15 minutes and 1 h at room temperature. Purification on a silica gel column yielded to 0.440 g of 3 h. (Yield: 98%). The characterization data were consistent with the proposed structure.

Copolymerization (Compounds 14, 15)

Procedures were adapted from (M. Akashi, k. Beppu, I. Kikuchi and O. Miyauchi, *Macromol. Sci.-Chem.*, A23 (10), pp. 1233-1249, (1986).

Copolymer 14

3'-metacryloyl-thymidine (0.148 g, 0.48 mmol, 1 eq), methacrylic acid (0.116 g, 1.35 mmol, 2.8 eq) and AIBN (0.01 g, 0.06 mmol, 0.13 eq) were dissolved in dry methanol. The reaction mixture was heated under nitrogen for 24 h. Methanol was evaporated and the resulting material was dissolved in a minimum amount of methanol. This solution was poured into a large amount of ether under stirring. The precipitate obtained was then filtered to give 110 mg of copolymer 9a. (Conversion: 40%). The characterization data were consistent with the proposed structure.

Copolymer 15

A same procedure was followed as for 9a. 3'-methacryloyl-thymidine (0.11 g, 0.35 mmol, 1 eq), metacrylic acid (0.162 g, 1.88 mmol, 5.3 eq), decyl methacrylate (0.025 g, 0.11 mmol, 0.31 eq) and AIBN (0.01 g, 0.06 mmol, 0.17 eq) were dissolved in dry methanol. Copolymer 9b (245 mg) was isolated after precipitation in MeOH/ether 1/100. (Conversion: 79%). The characterization data were consistent with the proposed structure.

Example 7

12-Azide dodecanoic acid (17a)

The 12-bromododecanoic acid 16a (5 g, 18 mol) and NaN$_3$ (1.7 g, 27 mol) were dissolved in DMF (5 mL), the mixture was heated to 70° C. and stirred for 10 h. The solution was then concentrated in vacuo and the residue dissolved in AcOEt. The organic layer was washed 2×200 mL H$_2$O, dried over MgSO$_4$, filtered, evaporated and dried in vacuo. (yield 100%). The characterization data were consistent with the proposed structure.

16-Azide hexadecanoic acid 17b was prepared using procedure similar to that described for the preparation of 17a. The characterization data were consistent with the proposed structure.

12-Azide dodecanoic acid ethyl ester (18a)

To 8 mol of 12-azide dodecanoic acid 17a (2 g) dissolved in EtOH (25 mL), ApTS (cat) was added and the mixture was reflux and stirred for 10 h. The solution was then concentrated in vacuo and the residue dissolved in AcOEt. The organic layer was washed 2×200 mL H$_2$O, dried over MgSO$_4$, filtered, evaporated and dried in vacuo. (yield 100%). The characterization data were consistent with the proposed structure.

Compound 18d was prepared from 17b using procedure similar to that described for the preparation of 18a. Compounds 18b and 18e was prepared from the corresponding 17a or 17b and 1-butanol using procedure similar to that described for the preparation of 18a.

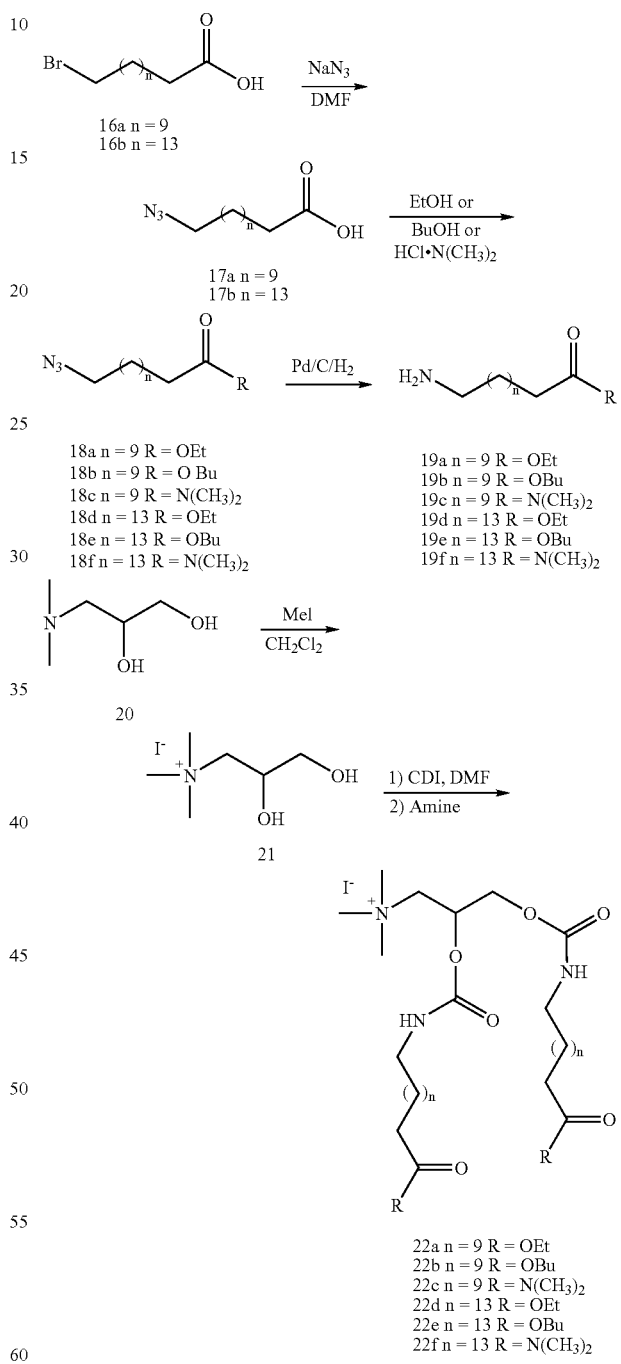

FIG. 8. Synthesis of a cationic amphiphile possessing a terminal ester or amide linkage.

12-Azide dodecanoic acid butyl ester 18b The characterization data were consistent with the proposed structure.

16-Azide hexadecanoic acid ethyl ester 18d The characterization data were consistent with the proposed structure.

16-Azide hexadecanoic acid butyl ester 18e The characterization data were consistent with the proposed structure.

12-Azide N,N-dimethyl-dodecylamide (18c). The characterization data were consistent with the proposed structure.

12-azide dodecanoic acid (17a) (2 g, 8 mol) was dissolved in THF (17 mL) and followed by the addition of CDI (1.3 g, 8 mol). The resulting solution was stirred at room temperature for 2 h after which dimethylamine (0.6 g, 8 mol) was added. After 24 h stirring at room temperature, the reaction mixture was concentrated in vacuo. The residue was dissolved in AcOEt and washed with satured NaHCO$_3$ (3×20 mL), water (3×50 mL), dried over MgSO$_4$, filtered, evaporated and dried in vacuo. The crude was purified by flash chromatography using a mixture AcOEt/Hexane (9:1) as the solvent which afforded the desire product (yield 80%). The characterization data were consistent with the proposed structure.

Compound 18f was prepared from 17b using procedure similar to that described for the preparation of 18c. 16-Azide N,N-dimethyl-hexadecylamide 18f The characterization data were consistent with the proposed structure.

12-Amino dodecanoic acid ethyl ester (19a) The characterization data were consistent with the proposed structure.

Pd/C was added to a solution of azide (2 g, 7.4 mol) in MeOH. The flask for catalytic hydrogenolysis was evacuated and filled with 50 psi H$_2$ before shaking for 8 h. The catalyst was filtered through Celite and washed with MeOH, the solvent was evaporated and dried in vacuo. (yield 100%). The characterization data were consistent with the proposed structure.

Compounds 19b, 19c, 19d, 19e and 19f was prepared from the corresponding 17 in a similar manner as described above.

12-Amino dodecanoic acid butyl ester 19b The characterization data were consistent with the proposed structure.

12-Amino N,N-dimethyl-dodecylamide 19c The characterization data were consistent with the proposed structure.

16-Amino hexadecanoic acid ethyl ester 19d The characterization data were consistent with the proposed structure.

16-Amino hexadecanoic acid butyl ester 19e The characterization data were consistent with the proposed structure.

16-Amino N,N-dimethyl-hexadecylamide 19f The characterization data were consistent with the proposed structure.

(2,3-Dihydroxy-propyl)-N,N,N-trimethyl-ammonium iodide 21

To 1 mol of 3-(dimethylamino)-1,2-propanediol 20 (1.2 g) dissolved in CH$_2$Cl$_2$ (5 mL), MeI (2 g, 1.5 mol) was added and the mixture stirred at rt for 1 h. The solution was then filtered and the filtrated recristalise in MeOH/Ether and dried in vacuo. (yield 100%). The characterization data were consistent with the proposed structure.

[2,3-Bis-(3-ethoxycarbonyl-propylcarbamoyloxy)-dodecyl]-trimethyl-ammonium iodide 22a To a solution of 2 mmol of CDI (0.61 g) in CH$_2$Cl$_2$ anhydrous (1 mL) was added a solution of 21 (0.5 g, 1.9 mmol) in DMF anhydrous (1 mL). The mixture stirred at room temperature for 1 h. Then 19a (2.2 mol) was added and the mixture reaction was stirred for 24 h. The solution was diluted in ether and the precipitated filtered. The product was rescritilize in MeOH/Ether (yield 70%). The characterization data were consistent with the proposed structure.

[2,3-Bis-(3-butoxycarbonyl-propylcarbamoyloxy)-dodecyl]-trimethyl-ammonium iodide 22b The characterization data were consistent with the proposed structure.

[2,3-Bis-(3-dimethylamide-propylcarbamoyloxy)-dodecyl]-trimethyl-ammonium iodide 22c The characterization data were consistent with the proposed structure.

[2,3-Bis-(3-ethoxycarbonyl-propylcarbamoyloxy)-hexadecyl]-trimethyl-ammonium iodide 22d The characterization data were consistent with the proposed structure.

[2,3-Bis-(3-butoxycarbonyl-propylcarbamoyloxy)-hexadecyl]-trimethyl-ammonium iodide 22e The characterization data were consistent with the proposed structure.

[2,3-Bis-(3-dimethylamide-propylcarbamoyloxy)-hexadecyl]-trimethyl-ammonium iodide 22f The characterization data were consistent with the proposed structure.

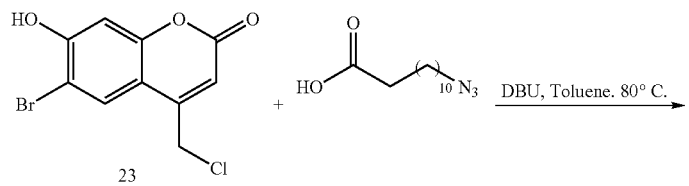

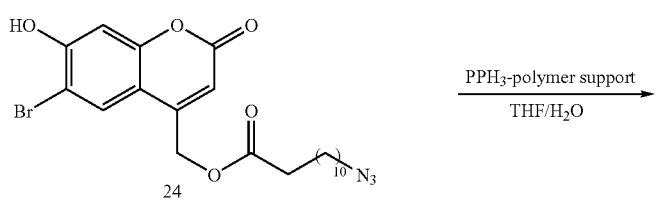

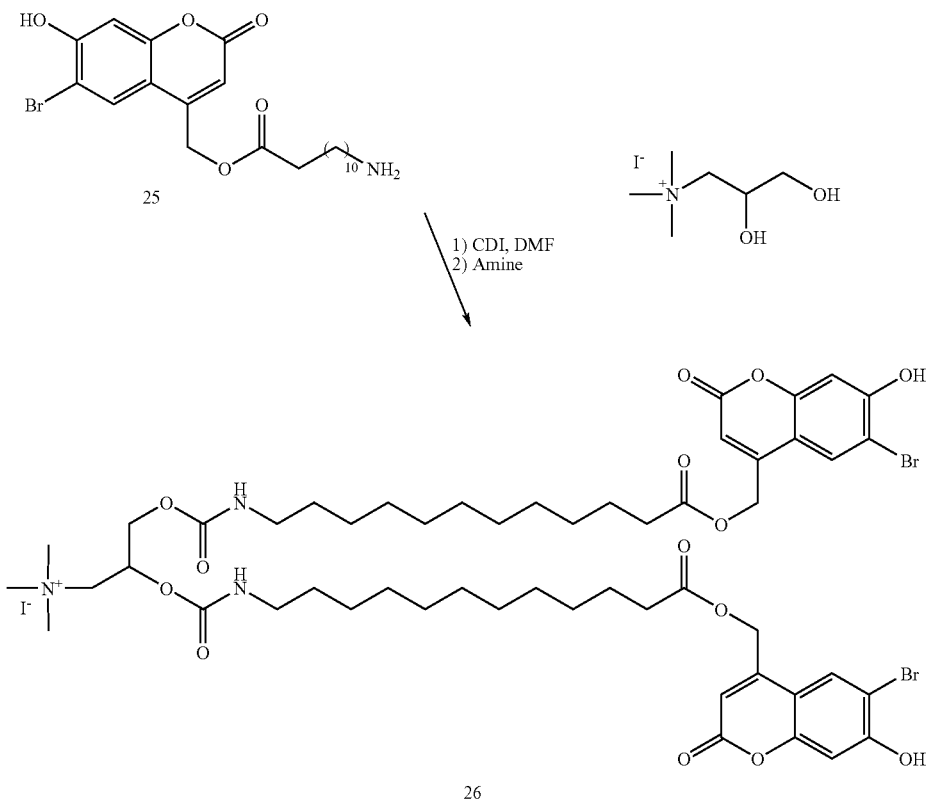

FIG. 9 Synthesis of a photocleavable cationic amphiphile.

6-Bromo-4-chloromethyl-7-hydroxy-chroman-2-one (23)

4-Bromoresorcinol (15.12 g, 80 mmol) and ethyl 4-chloroacetoacetate (16.2 mL, 0.12 mmol) were stirred in 80 mL of conc. $H_2SO_4$ for six days. The reaction mixture was poured into crushed ice with stirring and the slurry stirred for 30 min. The crude product was then filtered and washed with cold water. It was then dissolved in ethyl acetate and washed with water, 5% aqueous sodium bicarbonate solution, water and saturated brine solution and dried over anhydrous $Na_2SO_4$. The ethyl acetate layer was concentrated to about 15 mL and the slurry cooled for 30 min and filtered to get the product (52%). The characterization data were consistent with the proposed structure.

12-Azido-dodecanoic acid 6-bromo-7-hydroxy-2-oxo-chroman-4-ylmethyl ester (24)

A mixture of 6-bromo-4-chloromethyl-7-hydroxy-chroman-2-one (0.67 g, 2.3 mmol), dry toluene (3 mL), 1,8-diazabicyclo[5.4.0]undec-7-ene (1.4 g, 9.3 mmol) and 12-azido dodecanoic acid (0.84 g, 0.35 mmol) was refluxed for 2 h. The reaction mixture was allowed to cool to room temperature, diluted with chloroform (10 mL), quenched with 1N HCl, and the layers separated. The organic layer was dried over $Na_2SO_4$ and evaporated to yield the crude product Purification was done by column chromatography eluting with $CH_2Cl_2$ to afford the product (yield 60%). The characterization data were consistent with the proposed structure.

12-Amino-dodecanoic acid 6-bromo-7-hydroxy-2-oxo-chroman-4-ylmethyl ester (25)

12-Azido-dodecanoic acid 6-bromo-7-hydroxy-2-oxo-chroman-4-yl methyl ester (1 g, 2.02 mmol) was dissolved in $THF/H_2O$ (10 mL/1 mL), $PPh_3$-polymer supported (1 g) was added and the mixture was shaken at room temperature for 18 h. The solution was then filtered, evaporated and dried in vacuo to afford the product. (yield 100%). The characterization data were consistent with the proposed structure.

{2,3-Bis-[11-(6-bromo-7-hydroxy-2-oxo-chroman-4-ylmethoxycarbonyl)-undecylcarbamoyloxy]-propyl}-trimethyl-ammonium iodide (26)

To a solution of 2 mmol of CDI (0.61 g) in $CH_2Cl_2$ anhydrous (1 mL) was added a solution of 6 (0.5 g, 1.9 mmol) in DMF anhydrous (1 mL). The mixture was stirred at room temperature for 1 h. Then 12-amino-dodecanoic acid 6-bromo-7-hydroxy-2-oxo-chroman-4-ylmethyl ester (1.03 g, 2.2 mmol) was added and the mixture reaction was stirred for 24 h. The solution was diluted in ether and the precipitate

Example 8

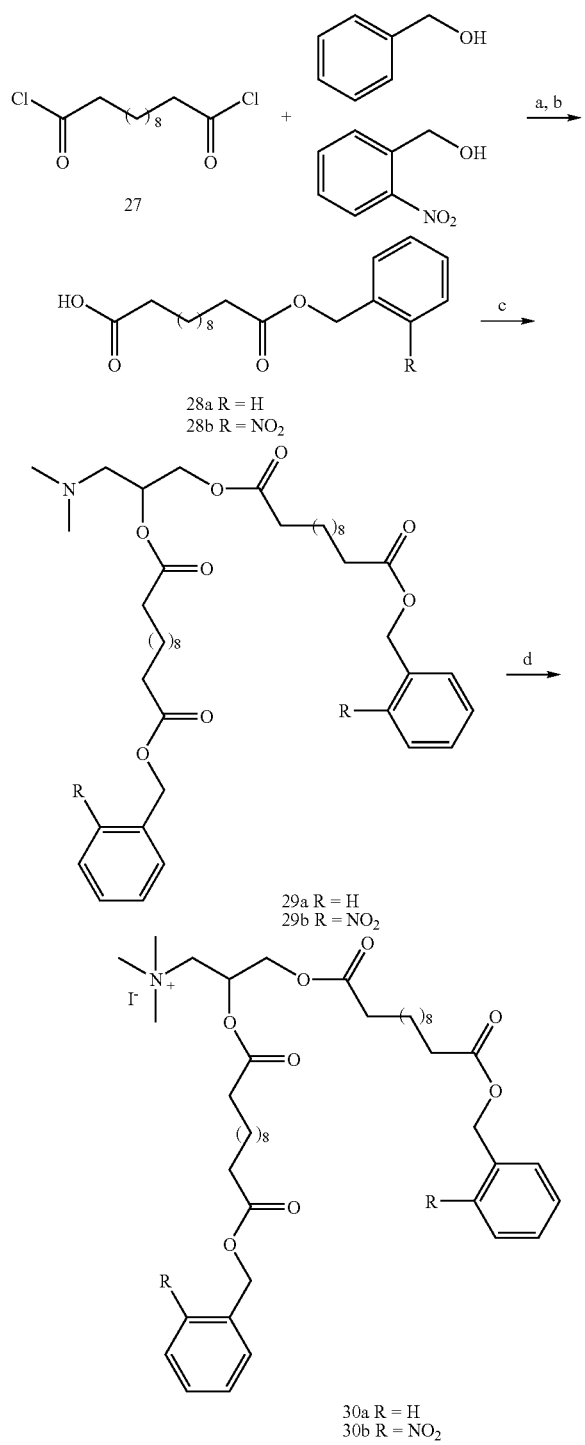

FIG. 10. Synthesis of cationic amphiphile with terminal ester linkages. a: TEA/THF, r.t., overnight; b: H₂O/TEA/THF, r.t., 3 h; c: 3-(Dimethylamino)-1,2-propanediol, DCC, DMAP, r.t., 2 days; d: MeI/DCM, r.t. 4 h Dodecanedioic acid monobenzyl ester (28a) A solution of benzyl alcohol (1.0 mL, 10 mmol) and TEA (1.4 mL, 10 mmol) in THF (25 mL) was added dropwise to an ice-cold solution of dodecanedioyl dichloride 1 (2.5 mL, 10 mmol) in THF (30 mL) over 2 hours. Then the solution was warmed to room temperature and stirred overnight. A mixture of H₂O (10 mL), TEA (1.4 mL, 10 mmol) and THF (10 mL) was added slowly to the solution over 1 hour, and the stirring was continued for 2 hours. THF was then removed and 20 mL H₂O was added to the residue. The mixture was extracted by ethyl ether (3×20 mL) and the organic phase was combined, dried over Na₂SO₄ and concentrated. Ethyl acetate (20 mL) was added to the residue and the suspension was filtered to remove dodecanedioic acid. Concentration of the filtrate followed by chromatography (Hexane:Ethyl acetate=4:1 to 2:1) afforded 1.3 g (40% yield) product as white solid. The characterization data were consistent with the proposed structure.

Dodecanedioic acid benzyl ester 2-(11-benzyloxycarbonyl-undecanoyloxy)-3-dimethylamino-propyl ester (29a) To an ice-cold solution of 24a (1.78 g, 5.5 mmol), 3-dimethylamino-propane-1,2-diol (0.3 mL, 2.5 mmol) and DMAP (catalytic amount) in DCM (15 mL) was slowly added a solution of DCC (1.1 g, 5.5 mmol) in DCM (5 mL). After the addition, the solution was warmed to room temperature and stirred for 2 days. The reaction mixture was then filtered to remove the insoluble DCU. Concentration of the filtrate followed by chromatography (50% EtOAc/DCM to 100% EtOAC) afforded 0.9 g (50% yield) product as colorless oil. The characterization data were consistent with the proposed structure.

[2,3-Bis-(11-benzyloxycarbonyl-undecanoyloxy)-propyl]-trimethyl-ammonium; iodide (30a) MeI (1 mL, 15 mmol) was added to a solution of 25a (0.9 g, 1.2 mmol) in DCM (5 mL). The solution was stirred for 4 hours and then concentrated. The residue was washed with ethyl ether to afford 0.9 g product (90% yield) as white powder. The characterization data were consistent with the chemical structure and formula.

Dodecanedioic acid mono-(2-nitro-benzyl)ester 28b A solution of 2-nitrobenzyl alcohol (1.53 g, 10 mmol) and TEA (1.4 mL, 10 mmol) in THF (25 mL) was added dropwise to an ice-cold solution of dodecanedioyl dichloride 1 (2.5 mL, 10 mmol) in THF (30 mL) over 2 hours. Then the solution was warmed to room temperature and stirred overnight. A mixture of H₂O (10 mL), TEA (1.4 mL, 10 mmol) and THF (10 mL) was added slowly to the solution over 1 hour, and the stirring was continued for 2 hours. THF was then removed and 20 mL H₂O was added to the residue. The mixture was extracted by ethyl, ether (20 mL×3) and the organic phase was combined, dried over Na₂SO₄ and concentrated. Ethyl acetate (20 mL) was added to the residue and the suspension was filtered to remove dodecanedioic acid. Concentration of the filtrate followed by chromatography (Hexane:Ethyl acetate=4:1 to 2:1) afforded 1.8 g (50% yield) product as white solid. The characterization data were consistent with the proposed structure.

Dodecanedioic acid 2-dimethylamino-1-[11-(2-nitro-benzyloxycarbonyl)-undecanoyloxymethyl]-ethyl ester 2-nitro-benzyl ester (29b) To an ice-cold solution of 2 (2.0 g, 5.5 mmol), 3-dimethylamino-propane-1,2-diol (0.3 mL, 2.5 mmol) and DMAP (catalytic amount) in DCM (15 mL) was slowly added a solution of DCC (1.1 g, 5.5 mmol) in DCM (5 mL). After the addition, the solution was warmed to room temperature and stirred for 2 days. The reaction mixture was then filtered to remove the insoluble DCU. Concentration of the filtrate followed by chromatography (50% EtOAc/DCM to 100% EtOAC) afforded 0.95 g (50% yield) product as colorless oil. The characterization data were consistent with the proposed structure.

{2,3-Bis-[11-(2-nitro-benzyloxycarbonyl)-undecanoyloxy]-propyl}-trimethyl-ammonium; iodide (30b) MeI (1 mL, 15 mmol) was added to a solution of 29b (1 g, 1.2 mmol) in DCM (5 mL). The solution was stirred for 4 hours and then concentrated. The residue was washed with ethyl ether to afford 1 g of product (90% yield) as white powder. The characterization data were consistent with the proposed structure.

Dodecanedioic acid mono-tert-butyl ester (32) To an ice-cold solution of dodecanedioic acid 31 (15 g, 65 mmol), tert-butyl alcohol (64 mL, 650 mmol) and DMAP (catalytic amount) in THE (80 mL) was slowly added a solution of DCC (16 g, 78 mmol) in THF (20 mL). After the addition, the solution was warmed to room temperature and stirred for 24 hours. The reaction mixture was then filtered to remove the insoluble DCU. Concentration of the filtrate followed by chromatography (20% EtOAc/Hexane to 40% EtOAC/Hexane) afforded 9 g (50% yield) product as colorless solid. The characterization data were consistent with the chemical structure and formula.

Dodecanedioic acid 2-(11-tert-butoxycarbonyl-undecanoyloxy)-3-dimethylamino-propyl ester tert-butyl ester (33) To an ice-cold solution of 26 (4.6 g, 16 mmol), 3-dimethylamino-propane-1,2-diol (0.9 mL, 7.6 mmol) and DMAP (catalytic amount) in DCM (40 mL) was slowly added a solution of DCC (4 g, 20 mmol) in DCM (10 mL). After

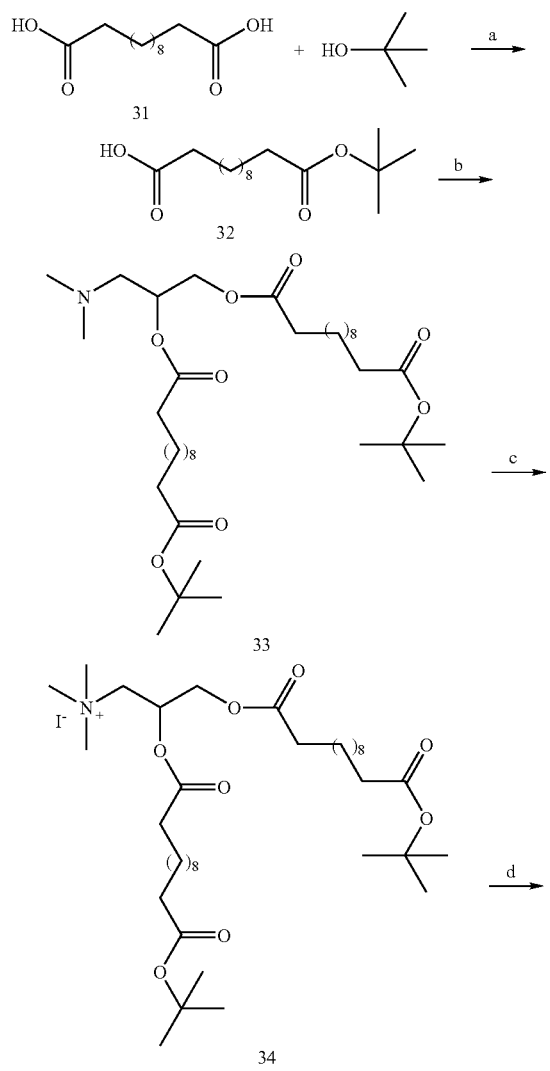

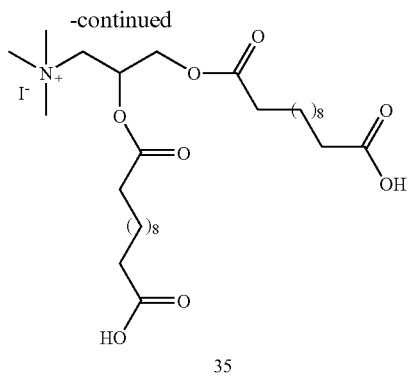

FIG. 11. Synthesis of t-butyl terminus amphiphiles a: DCC, DMAP, THF, r.t., 24 h; 3-(Dimethylamino)-1,2-propanediol, DCC, DMAP, r.t., 2 days; c: MeI, DCM, r.t., 4 h; d: TFA, DCM, r.t., 4 h the addition, the solution was warmed to room temperature and stirred for 2 days. The reaction mixture was then filtered to remove the insoluble DCU. Concentration of the filtrate followed by chromatography (50% EtOAc/DCM to 100% EtOAC) afforded 2.3 g (46% yield) product as colorless oil. The characterization data were consistent with the chemical structure and formula.

[2,3-Bis-(11-tert-butoxycarbonyl-undecanoyloxy)-propyl]-trimethyl-ammonium; iodide (34) MeI (1 mL, 15 mmol) was added to a solution of 29 (1.1 g, 1.7 mmol) in DCM (5 mL). The solution was stirred for 4 hours and then concentrated. The residue was recrystalized in DCM/Ethyl ether to afford 1.0 g product (75% yield) as white powder. The characterization data were consistent with the chemical structure and formula.

[2,3-Bis-(11-carboxy-undecanoyloxy)-propyl]-trimethyl-ammonium; iodide (35) A solution of 0.70 g 30 and TFA (6 mL) in DCM (24 mL) was stirred at room temperature for 4 hours. Then the solution was concentrated and the residue was re-crystallized in MeOH/Ethyl ether to afford 0.54 g (90% yield) product as light yellow powder. The characterization data were consistent with the chemical structure and formula.

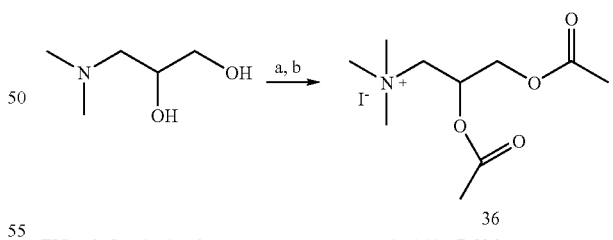

FIG. 12. Synthesis of acyl analog. a: Acetyl anhydride, DCM, r.t., overnight, b: MeI (2,3-Diacetoxy-propyl)-trimethyl-ammonium; iodide 36 A mixture of 3-dimethyl-amino-propane-1,2-diol (0.30 mL, 2.5 mmol), acetyl anhydride (2 mL, excess) and DCM (5 mL) was stirred overnight at room temperature. Then MeI (2 mL, excess) was added to the solution and the stirring was continued for 4 hours. Then the solution was concentrated and ethyl ether (20 mL) was added to the residue to precipitate the product (0.73 g, 85% yield). The characterization data were consistent with the chemical structure and formula.

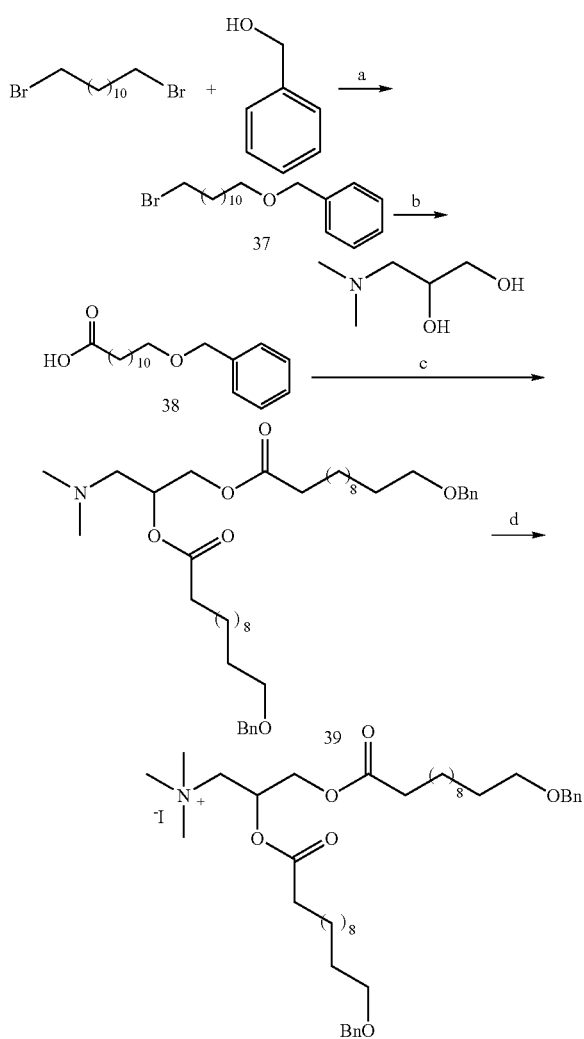

FIG. 13. Synthesis of BnO analog a: NaH, THF, reflux, 24 h, 70%; b:NaNO₂, HOAc, DMSO, 35° C., overnight, 60%; c: DCC, DMAP, DCM, r.t., 2d, 30%; d: MeI, DCM, r.t, 4 h, 90%

12-Bromo-dodecyloxymethyl)-benzene 37. NaH (0.7 g, 29 mmol) was slowly added into a solution of benzyl alcohol (1.5 mL, 14 mmol) in 20 mL THF. The suspension was refluxed for 2 hours. Then a solution of 1,12-dibromo-dodecane (12 g, 36 mmol) in 30 mL of THF was added and the suspension was refluxed for one day. The reaction was quenched by 20 mL 0.01 N HCl and THF was removed under vacuum. The aqueous phase was extracted by DCM (20 mL×3). The organic phase was combined, dried over Na₂SO₄ and concentrated. The residue was chromatographed (Hex to 5% EtoAc in Hex) to afford 3.6 g (70% yield) product as colorless oil. The characterization data were consistent with the chemical structure and formula.

12-Benzyloxy-dodecanoic acid 38. A solution of 12-Bromo-dodecyloxymethyl)-benzene (2 g, 5.6 mmol), sodium nitrite (1.9 g, 28 mmol), and acetic acid (4 mL, 67 mmol) in DMSO (10 mL) was stirred at 35° C. for overnight[1]. The reaction mixture was then acidified with 10 mL 1 N HCl and extracted with ethyl ether (30 mL×2). The organic phase was combined, dried over Na₂SO₄ and concentrated. The residue was chromatographed (5% EtoAc in Hex to 30% EtoAc in Hex) to afford 1 g (60% yield) product as light yellow solid. The characterization data were consistent with the chemical structure and formula.

12-Benzyloxy-dodecanoic acid 2-(12-benzyloxy-dodecanoyloxy)-3-dimethylamino-propyl ester 39 To an ice-cold solution of 12-Benzyloxy-dodecanoic acid (0.82 g, 2.67 mmol), 3-dimethylamino-propane-1,2-diol (0.11 mL, 1 mmol) and DMAP (catalytic amount) in DCM (10 mL) was slowly added a solution of DCC (0.66 g, 3.2 mmol) in DCM (5 mL). After the addition, the solution was warmed to room temperature and stirred for 2 days. The reaction mixture was then filtered to remove the insoluble DCU. Concentration of the filtrate followed by chromatography (50% EtOAc/DCM to 100% EtOAC) afforded 0.21 g (30% yield) product as colorless oil. The characterization data were consistent with the chemical structure and formula.

[2,3-Bis-(12-benzyloxy-dodecanoyloxy)-propyl]-trimethyl-ammonium; iodide 40. MeI (0.5 mL, 7 mmol) was added to a solution of 39 (0.26 g, 0.37 mmol) in DCM (2 mL). The solution was stirred for 4 hours and then concentrated. The residue was washed with ethyl ether to afford 0.28 g (90% yield) product as white powder. The characterization data were consistent with the chemical structure and formula.

Example 9

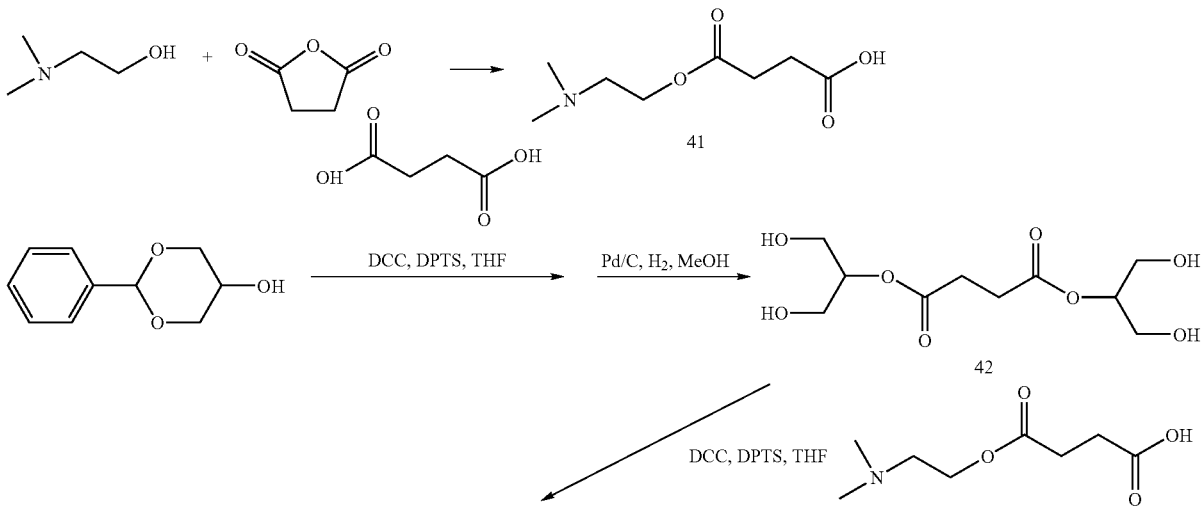

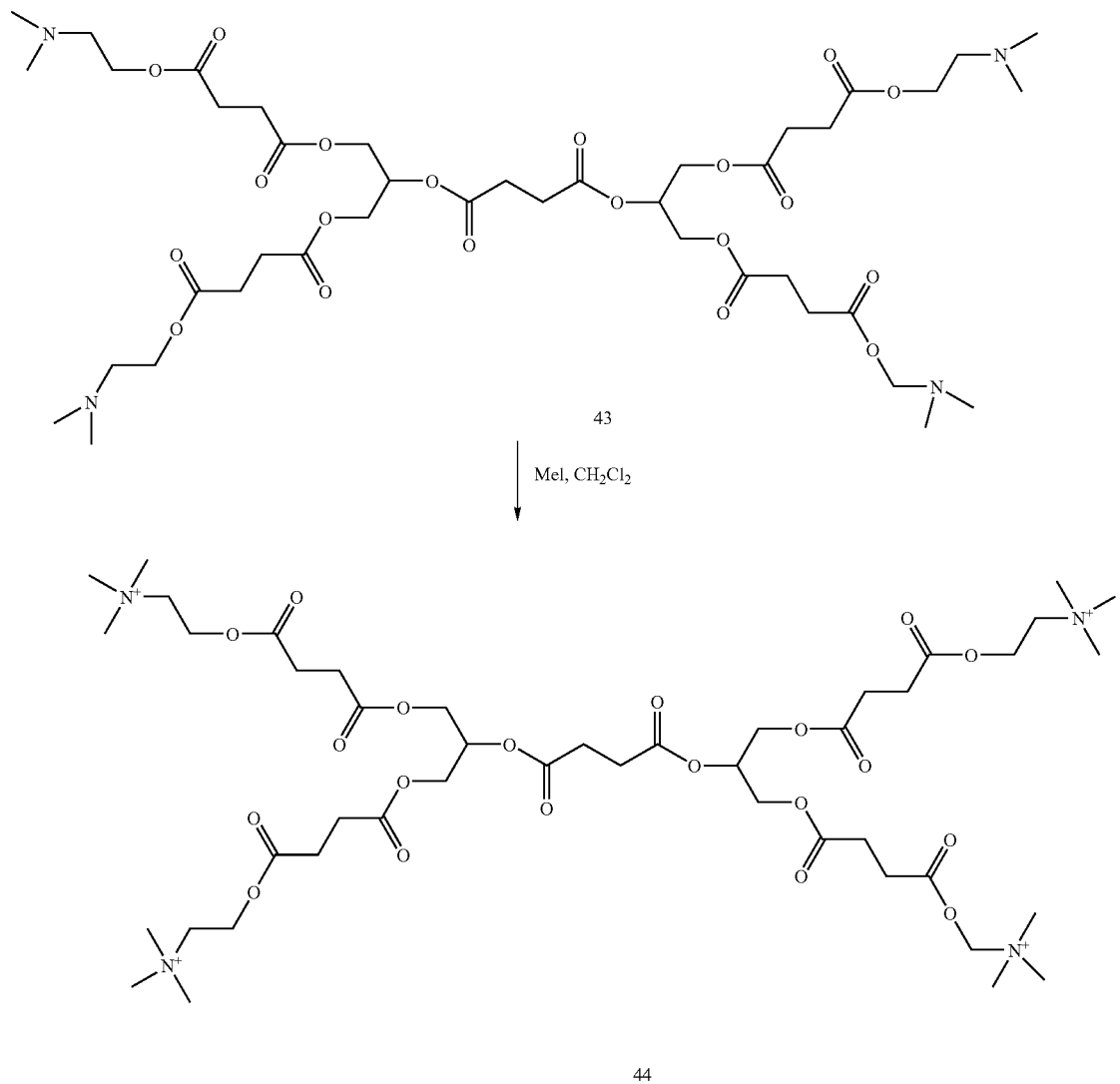

FIG. 14 Degradable cationic dendrimers for gene delivery

Succinic acid mono-(2-dimethylamino-ethyl)ester 41

The 2-dimethylamino ethanol (10 g, 0.11 mol) was dissolved in pyridine (100 mL) followed by the addition of succinic anhydride (16 g, 0.16 mol). The mixture was stirred at room temperature for 18 h before the pyridine was removed under vacuum at 40 C. The remaining solid was recrystallized from MeOH/Ether. The characterization data were consistent with the chemical structure and formula.

Dimethylamino-[G0]-PGLSA dendrimer 43

Succinic acid mono-(2-dimethylamino-ethyl)ester (2.14 g, 11.3 mmol), OH-[G0]-PGLSA 42 (0.54 g, 2.01 mmol), DPTS (1.25 g, 4.27 mmol) were dissolved in THF and DCC (3.51 g, 17.05 mmol) was added. The reaction mixture was stirred at room temperature for 18 h under nitrogen atmosphere. Upon completion of the reaction the DCU was filtered off and washed with a small amount of THF and the solvent evaporated. The crude mixture was purified by silica gel chromatography, eluting with AcOEt (yield 80%). The characterization data were consistent with the chemical structure and formula.

Trimethylamino-[G0]-PGLSA dendrimer iodide, 44

Dimethylamino-[G0]-PGLSA dendrimer (1.4 g, 1.5 mmol) was dissolved in $CH_2Cl_2$ and methyl iodide was added (1.1 g, 8 mmol). The reaction mixture was stirred at room temperature for 3 h. The solvent was evaporated to yield the product (yield 100%). The characterization data were consistent with the chemical structure and formula.

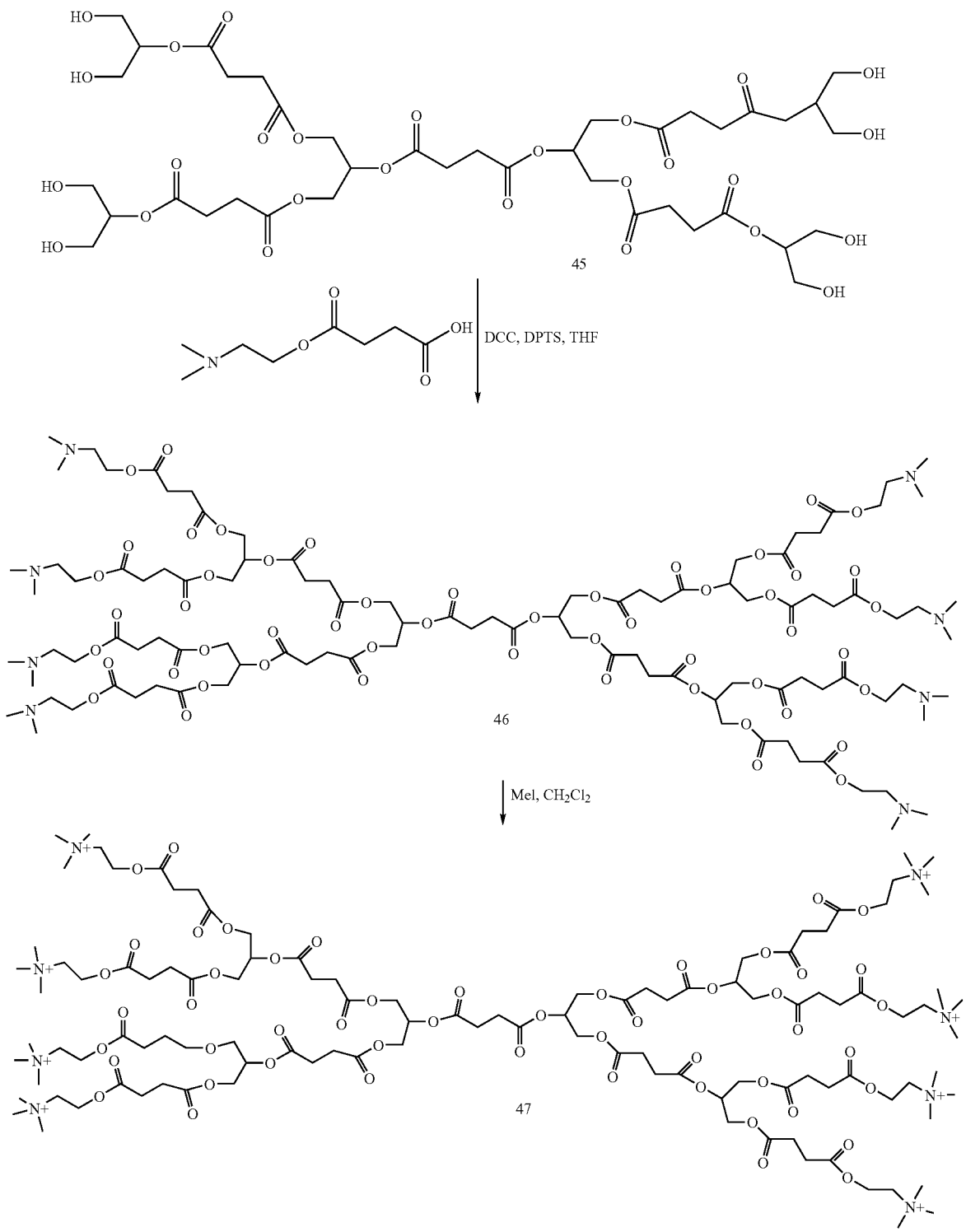

FIG. 15 Synthesis of degradable cationic dendrimers

Dimethylamino-[G1]-PGLSA dendrimer, 46

Succinic acid mono-(2-dimethylamino-ethyl)ester (1.59 g, 8.42 mmol), OH-[G1]-PGLSA 45 (0.5 g, 0.52 mmol), DPTS (0.88 g, 3.01 mmol) were dissolved in THF. DCC (2.3 g, 11.2 mmol) was added to the mixture and the reaction was stirred at room temperature for 24 h under nitrogen atmosphere. Upon completion of the reaction the DCU was filtered off and washed with a small amount of THF and the solvent evaporated. The crude mixture was purified by silica gel chromatography, eluting with AcOEt. The characterization data were consistent with the chemical structure and formula.

Trimethylamino-[G1]-PGLSA dendrimer iodide, 47

RT for 16 hours. The DCU precipitate was filtered and the solution was evaporated. The residue was resuspended in 50 mL of ethanol, cooled to 0° C. for 6 hours and filtered. The precipitate was resuspended in 75 mL of $CH_2Cl_2$, washed with 75 mL of $H_2O$, dried over $Na_2SO_4$, and the solvent

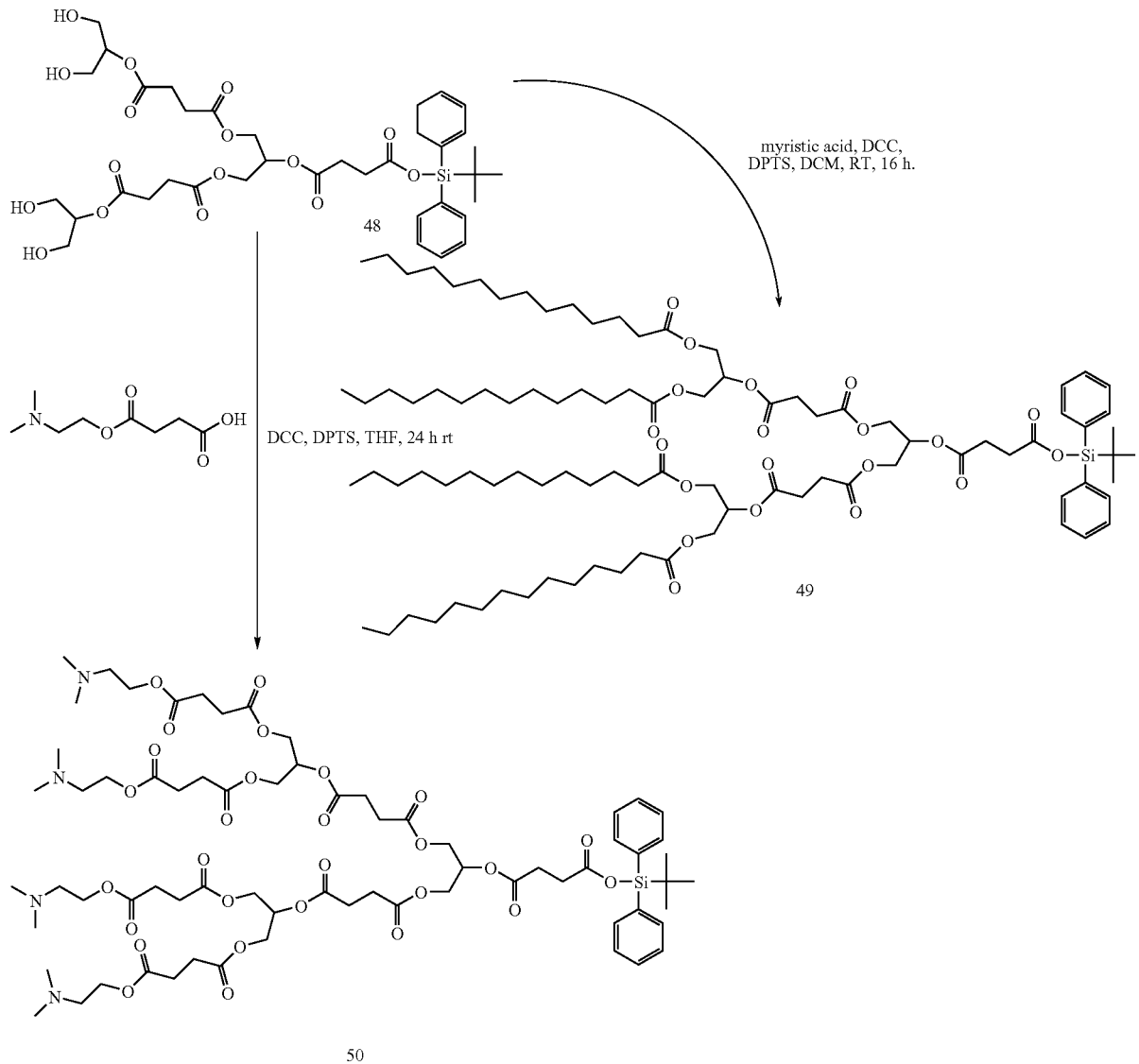

FIG. 16 Synthesis of dendrons

Dimethylamino-[G1]-PGLSA dendrimer (0.5 g, 0.21 mmol) was dissolved in $CH_2Cl_2$ and methyl iodide was added (2.9 g, 2.1 mmol). The reaction mixture was stirred at room temperature for 3 h. The solvent was evaporated to yield the product (100%). The characterization data were consistent with the chemical structure and formula.

Synthesis of Myr-[G2]-PGLSA-TBDPS, 49

0.45 g (0.58 mmol) of compound OH-[G2]-PGLSA-TB-DPS (48) was dissolved in 75 mL of $CH_2Cl_2$ with 0.63 g (2.77 mmol) of myristic acid(Myr), 0.34 g (1.16 mmol) of DPTS, and 0.72 g (3.47 mmol) of DCC. The reaction was stirred at evaporated to yield 0.84 g of product (89% yield). The characterization data were consistent with the chemical structure and formula.

Dimethylamino-[G2]-PGLSA-TBDPS dendron, 50

Succinic acid mono-(2-dimethylamino-ethyl)ester (1.23 g, 6.46 mmol), OH-[G2]-PGLSA-TBDPS dendron (0.9 g, 1.15 mmol), DPTS (0.72 g, 2.44 mmol) were dissolved in THF and DCC (1.95 g, 9.46 mmol) was added. The reaction mixture was stirred at room temperature for 14 h under nitrogen atmosphere. Upon completion of the reaction the DCU was filtered off and washed with a small amount of THF and the solvent evaporated. The crude mixture was purified by silica gel chromatography, eluting with AcOEt. The characterization data were consistent with the chemical structure and formula.

Example 10

1-(6-Hydroxymethyl-2,2-dimethyl-tetrahydro-furo[3,4-d][1,3]dioxol-4-yl)-1H-pyrimidine-2,4-dione 51

Para-toluene sulfonic acid (2.33 g, 12.3 mmoles, 3 eq.) was added to Uridine (1 g, 4.1 mmoles) in 180 mL of anhydrous acetone. After 4 hours at room temperature, acetone was evaporated and the residual crude product was dissolved in 200 mL of ethyl acetate. The organic phase was washed three times with 20 mL of a hydrogenocarbonate 10% solution, then dried over sodium sulfate. The solvent was removed under vacuum. 0.979 g of white powder was isolated (Yield: 83%). The characterization data were consistent with the chemical structure and formula.

Uridine acetonide phosphatidylcholine 52

Uridine-oxo-dioxaphospholane
Freshly distilled THF (30 mL) and dry TEA (803 uL, 2 eq, 5.71 mmoles) were added under nitrogen to Uridine acetonide 13 (0.80 g, 2.81 mmoles). The mixture was cooled down to 0° C. and 2-Chloro-2-oxo-1,3,2-dioxaphospholane (414 uL, 1.6 eq, 4.5 mmoles) was added drop-wise.

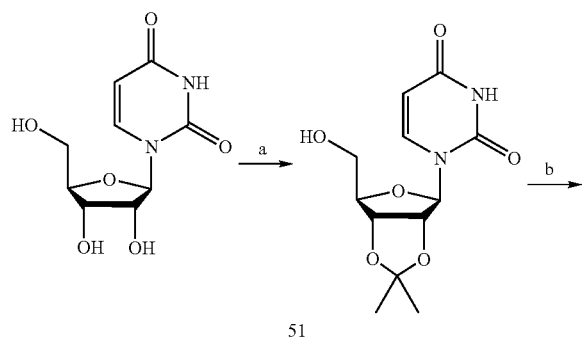

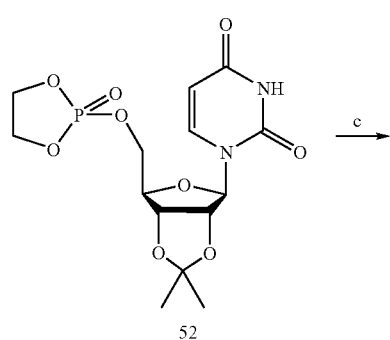

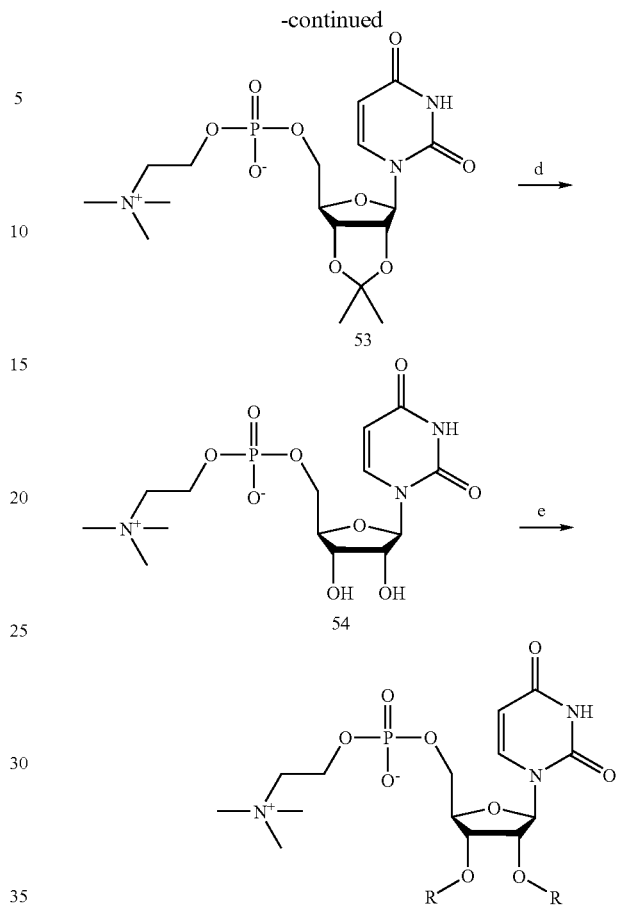

55 - R = myristroyl
56 - R = stearoyl
57 - R = arachldonoyl
58 - R = oleoyl

FIG. 17: Synthesis of phosphocholine derivatives a) acetone, APTS, RT, 83% yield; b) chloro-oxo-dioxaphosphospholane, TEA, THF, O C; c) triethylamine, AcCN, THF, 60 C., 48 hrs, 82% yield two steps; d) $H_2CO_2H$, MEOH; RT, 70% yield; e) fatty acid, DCC, DMAP, DMF, RT 15-60% yield depending on the fatty acid The reaction mixture was stirred at room temperature for 15 hours. Then, TEA salts were removed by filtration under suction at 0° C. Most of the solvent was evaporated under reduced pressure at 0° C. and 8 mL of the residual solution was directly used without further purification in the following step.

Anhydrous trimethylamine (4 mL, 15.5 eq, 44 mmoles) were condensated at −50° C. under nitrogen in a pressure tube. Next cold trimethyl amine was added. The reaction mixture was then maintained at 60° C. under stirring for 48 hours. After evaporation at room temperature of the residual trimethylamine, and after filtration a white solid was isolated. 1,035 of a solid are obtained after drying under high vacuum (Yield: 82%). The characterization data were consistent with the chemical structure and formula.

Uridine phosphatidylcholine 54

Compound 53 (0.20 g, 0.44 mmoles) in 1.5 mL of formic acid (98%) was stirred for 24 hours at room temperature. The excess of formic acid was co-evaporated with ethanol. Crystallization in a binary mixture methanol/ethanol gave 0.127 g of a white hydroscopic solid (Yield: 70%). The characterization data were consistent with the chemical structure and formula.

2',3'dimyristoyl-5'phosphatidylcholine-uridine 55

Myristic acid (185 mg, 3 eq, 0.72 mmol), DCC (148 mg, 3 eq, 0.72 mmol) and DMAP (88 mg, 3 eq, 0.72 mmol), were added to compound 54 in 20 mL of anhydrous DMF. After 72 hours at room temperature, DCU was removed by filtration. The solvent was evaporated and the product was washed with ether (2×25 mL). 123 mg of product was isolated after chromatography (LH 20, DCM/MeOH 5/5), (Yield: 58%). The characterization data were consistent with the chemical structure and formula.

Bis-(2',3'-stearoyl)-5'-(phosphocholine)-uridine (R=(CH$_2$)$_{16}$CH$_3$) 56

Stearic acid (555 mg, 4 eq, 1.95 mmol), DCC (402 mg, 4 eq, 1.95 mmol) and DMAP (238 mg, 4 eq, 1.95 mmol), were added to uridine phosphocholine (200 mg, 0.49 mmol) in 20 mL of anhydrous DMF. After 72 hours at room temperature, the DMF was evaporated and the residual solid was dissolved in 20 mL of methylene chloride. DCU was removed by filtration and solvent evaporated. The crude material was purified by exclusion chromatography (LH 20, DCM/MeOH 5/5). 175 mg of product were isolated. (Yield: 38%). RF: 0.17 (reverse phase, DCM/MeOH 5/5). The characterization data were consistent with the chemical structure and formula.

Bis-(2',3'-arachidonyl)-5'-(phosphocholine)-uridine (R=(CH$_2$)$_{18}$CH$_3$) 57

Arachidic acid (611 mg, 4 eq, 1.95 mmol), DCC (402 mg, 4 eq, 1.95 mmol) and DMAP (238 mg, 4 eq, 1.95 mmol), were added to uridine phosphocholine (200 mg, 0.49 mmol) in 20 mL of anhydrous DMF. After 72 hours at room temperature, the DMF was evaporated and the residual solid is dissolved in 20 mL of methylene chloride. DCU was removed by filtration and solvent evaporated. The crude material was purified by exclusion chromatography (LH 20, DCM/MeOH 5/5). 73 mg of the product were isolated. (Yield: 15%). The characterization data were consistent with the chemical structure.

Bis-(2',3'-oleoyl)-5'-(phosphocholine)-uridine (R=(CH$_2$)$_7$CH=CH(CH$_2$)$_7$CH$_3$) 58

Uridine phosphocholine (200 mg, 1 eq, 0.49 mmol), DCC (402 mg, 4 eq, 1.95 mmol) and DMAP (238 mg, 4 eq, 1.95 mmol) were dissolved in 20 mL of anhydrous DMF under argon. Oleic acid (619 mg, 4 eq, 1.95 mmol) was added and the mixture was stirred in the dark. After 72 hours at room temperature, the DMF was evaporated and the residual solid was dissolved in 20 mL of methylene chloride. DCU was removed by filtration and solvent evaporated. The crude material was purified by exclusion chromatography (LH 20, DCM/MeOH 5/5). 150 mg of product. (Yield: 33%). RF: 0.30 (reverse phase, DCM/MeOH 5/5). The characterization data were consistent with the chemical structure and formula Example 11

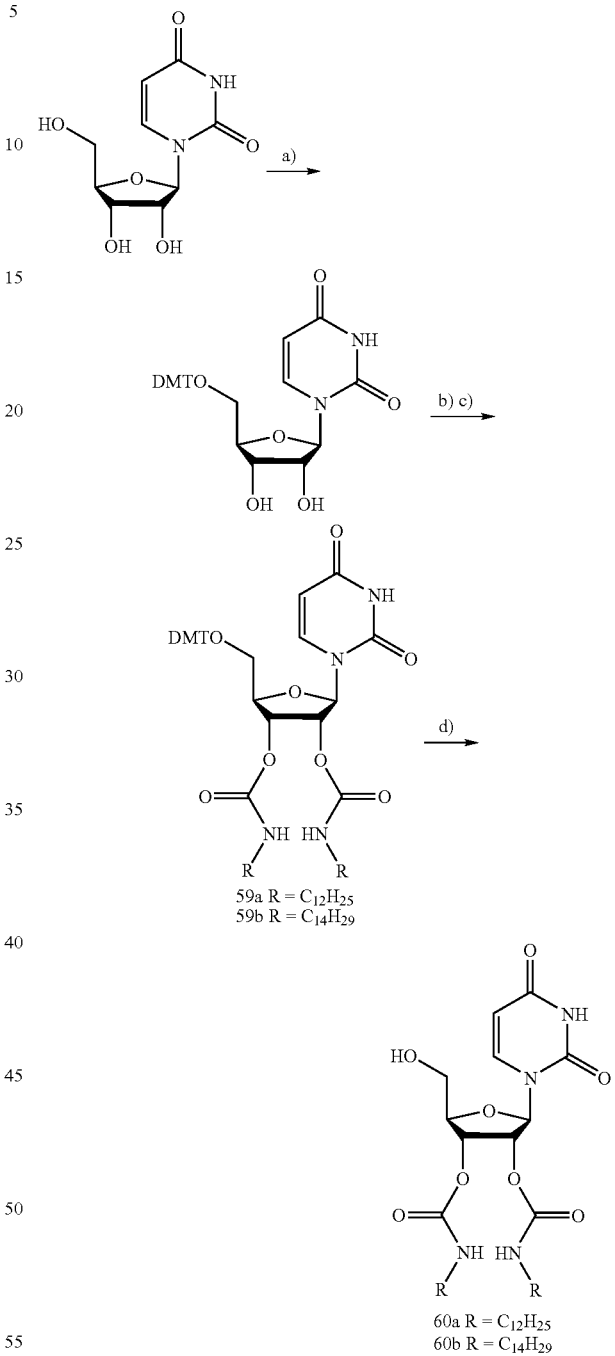

FIG. 18. Synthesis of casrbamate analogs a) DMTCl in Pyridine b) CDI, DMAP in DMF, 1 h c) tetradecylamine 12 h, (Yield = 40%) or dodecylamine 12 h, (Yield = 35%) d) trichloracetic acid 3% in DCM, (Yield = 95%).

2',3'-di(tetradecylcarbamoyl acid)-5'-(4,4'dimethoxytrityl)uridine (59a)

5'-4,4'-dimethoxytrityluridine (1 g, 1 eq), carbonyldiimidazole (1.22 g, 2.2 eq) and a catalytic amount of dimethylaminopyridine (DMAP) were dissolved in 20 mL of anhydrous DMF. After 1 hour at room temperature, tetradecylamine (2 g, 7 eq) was added, then the reaction mixture was stirred for 12 hours. The DMF was removed under reduced pressure. 0.5 g of product were isolated after chromatography on silica gel (DCM/MeOH, 95/5). (Yield: 40%). The characterization data were consistent with the chemical structure.

2',3'-di(tetradecylcarbamoyl acid)-uridine (60a)

An excess of a 3% trichloroacetic acid solution in methylene chloride was added to 2',3'-di(tetradecylcarbamoyl acid)-5'-dimethoxytrityluridine (0.4 g) were dissolved in 20 mL of dry methylene chloride. The reaction mixture was stirred for 30 min at room temperature. After addition of methanol (3 mL), the organic layer was washed three times with 10 mL of water and dried over sodium sulfate. The product (0.25 g) was obtained after chromatography (DCM/MeOH 95/5) (Yield: 95%). The characterization data were consistent with the chemical structure.

2',3'-di(dodecylcarbamoyl acid)-)-5'-(4,4'dimethoxytrityluridine (59b)

5'-dimethoxytrityluridine (1 g, 1 eq), carbonyldiimidazole (1.22 g, 2.2 eq) and a catalytic amount of dimethylaminopyridine (DMAP) were dissolved in 20 mL of anhydrous DMF. After 1 hour at room temperature, dodecylamine (1.80 g, 7 eq) was added, then the reaction mixture was stirred for 12 hours. The DMF was removed under reduced pressure. The characterization data were consistent with the chemical structure.

2',3'-di(dodecylcarbamoyl acid)-uridine (60b)

An excess of a 3% trichloroacetic acid solution in methylene chloride was added to 59b (0.5 g) dissolved in 20 mL of dry methylene chloride. The reaction mixture was stirred for 30 min at room temperature. After addition of methanol (3 mL), the organic layer was washed three times with 10 mL of water and dried over sodium sulfate. 0.25 g of the product was obtained after chromatography (DCM/MeOH 95/5). The characterization data were consistent with the chemical structure.

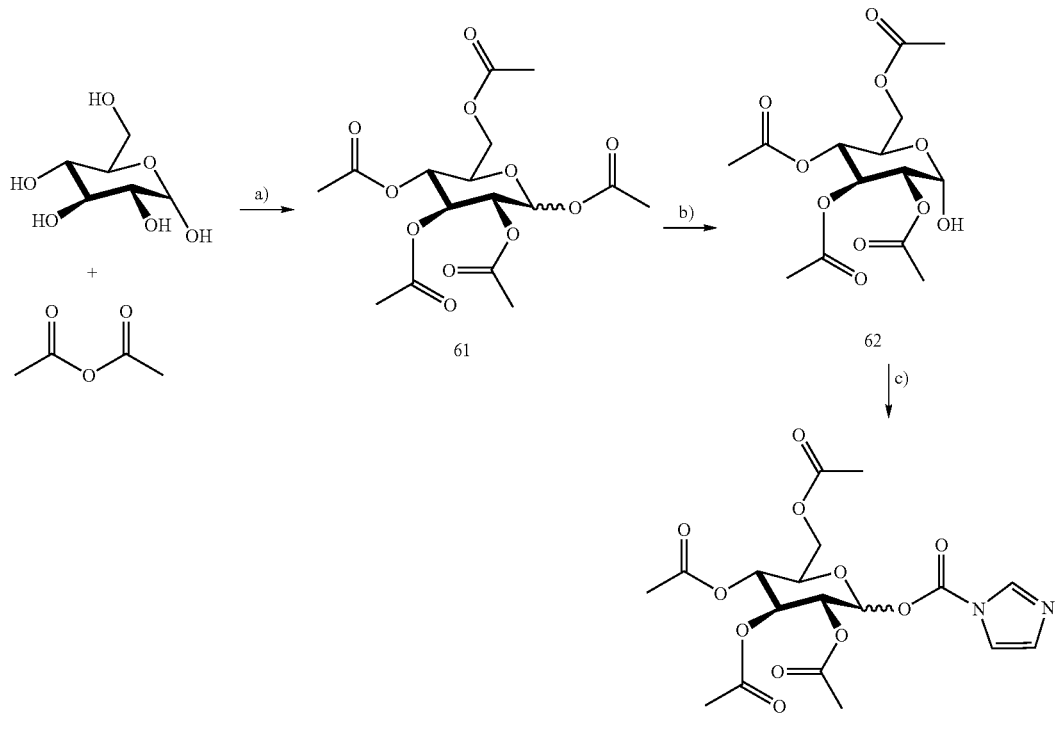

FIG. 19. Synthesis of acetyl sugar a) Acetic anhydride in pyridine, (Yield = 90%) b) hydrazine acetate in DMF, (Yield = 65%) c) CDI in ether, (Yield = 100%)

1,2,3,4,6-pentaacetylglucose 61

Glucose (2 g, 11.1 mmoles) was dissolved in pyridine cooled at 0° C., then acetic anhydride (15 g, 144.3 mmoles) was added drop wise. The mixture was stirred for 2 h and then washed with cold water, HCl 1N, NaHCO$_3$ and brine. The organic layer was dried over sodium sulfate. 5.5 g were obtained after chromatography (cyclohexane/AcOEt 7/3) (yield: 90%). The characterization data were consistent with the chemical structure.

2,3,4,6-tetraacetylglucose 62

1,2,3,4,6-tetraacetylglucose (5.5 g, 7.1 mmoles) and hydrazine acetate (0.8 g, 1.2 eq) were dissolved in 20 mL of DMF. After 1 hour, DMF was removed under reduced pressure, the crude product was dissolved in 50 mL of ethyl acetate and washed twice with 20 mL of water. The organic layer was dried over sodium sulfate. 2 g of product was obtained after chromatography (cyclohexane/AcOEt 6/4) (yield: 65%). The characterization data were consistent with the chemical structure.

2,3,4,6-tetraacetylglucose-1-imidazolylcarbonyl 63

2,3,4,6-tetraacetylglucose (0.4 g, 1.1 mmoles) was dissolved in 5 mL of ether, then n,n-carbonyldiimidazole (0.205 g, 1.2 mmoles) was added. The mixture is stirred for 2 h at room temperature, then filtered on a pad of silica. The filtrate was evaporated to give the product (yield: 100%). This product was used immediately without further purification. Rf: 0.29 (CH$_2$Cl$_2$/MeOH 95/5). The characterization data were consistent with the chemical structure.

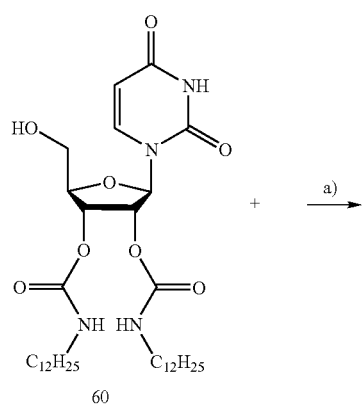

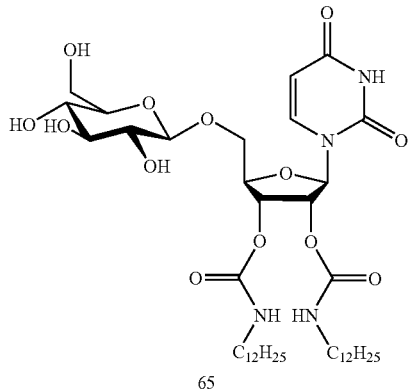

FIG. 20. Synthesis of sugar analogs a) ZnBr$_2$ in CH$_2$Cl$_2$ reflux (Yield = 44%), b) MeONa in MeOH (quantitative)

2,3,4,6-tetraacetylglucoside-5'-di(dodecylcarbamoyl acid)-uridine 64

2,3,4,6-tetraacetylglucose-1-imidazolylcarbonyl (0.20 g, 0.45 mmoles), 2',3'-di(dodecylcarbamoyl acid)-uridine (0.33 g, 0.49 mmoles) and ZnBr$_2$ (0.11 g, 0.49 mmoles) were dissolved in 10 mL of dichloromethane. Reaction mixture was heated for 12 h. 0.21 g is isolated after chromatography (DCM/MeOH 95/5). (yield: 44%). The characterization data were consistent with the chemical structure.

glucoside-5'-di(dodecylcarbamoyl acid)-uridine 65

2,3,4,6-tetraacetylglucoside-5'-di(dodecylcarbamoyl acid)-uridine was dissolved in 10 mL of MeOH. MeONa was added and the reaction was run for 4 h. The product was obtained. (yield >99%). The characterization data were consistent with the chemical structure.

1,2,3,4,6-pentachloroacetylglucose 66

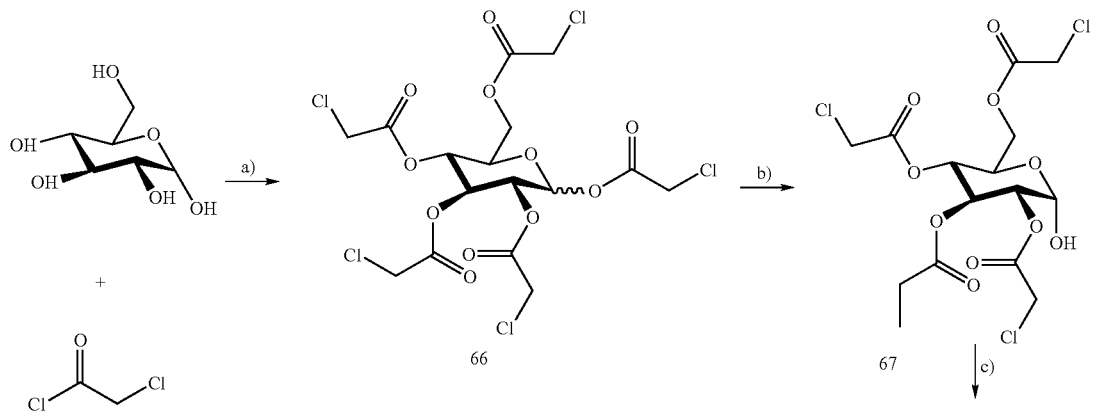

-continued

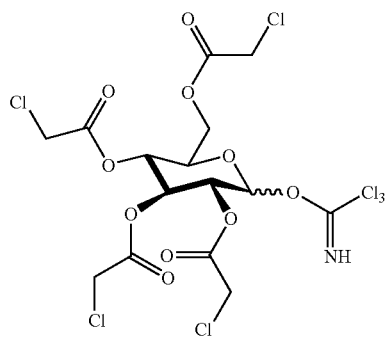

68

FIG. 21. Synthesis of 2,3,4,6-tetrachloroacetylglucoside-1-trichloroacetimidate a) Chloroacetyl cholride in pyridine, (Yield = 63%) b) hydrazine acetate in DMF, (Yield = 46%) c) trichloroacetonitrile, K2CO3, in DCM, (Yield = 100%)

Glucose (2 g, 11.1 mmoles) was dissolved in a mixture of methylenechloride/pyridine (60 ml/6 ml) cooled at 0° C., and then chloroacetyl chloride (16.3 g, 144.3 mmoles) was added drop wise. The mixture was stirred for 2 h and then washed with cold water, HCl 1N, NaHCO$_3$ and brine. The organic layer was dried over sodium sulfate. 4 g were obtained after chromatography (cyclohexane/AcOEt 7/3) (yield: 63%). Rf: 0.83 (cyclohexane/AcOEt 5/5). The characterization data were consistent with the chemical structure.

2,3,4,6-tetrachloroacetylglucose 67

1,2,3,4,6-tetrachloroacetylglucose (4 g, 7.1 mmoles) and hydrazine acetate (0.8 g, 1.2 eq) were dissolved in 20 mL of DMF. After 1 hour, DMF was removed under reduced pressure, the crude product was dissolved in 50 mL of ethyl acetate and washed twice with 20 mL of water. The organic layer was dried over sodium sulfate. 2 g of product were obtained after chromatography (cyclohexane/AcOEt 6/4) (yield: 46%). The characterization data were consistent with the chemical structure.

2,3,4,6-tetrachloroacetylglucoside-1-trichloroacetimidate 68

2,3,4,6-tetrachloroacetylglucose (0.15 g, 1 eq), trichloroacetonitrile chloride (0.5 mL, 1.1 eq) and a catalytic amount of potassium carbonate were dissolved in dry DCM. After 12 hours under argon, the organic layer was filtrated on celite. 0.15 g of product was obtained after chromatography (CH$_2$Cl$_2$). This product was used immediately to avoid degradation. (yield: 78%). Rf: 0.96 (CH$_2$Cl$_2$/MeOH 95/5). The characterization data were consistent with the chemical structure.

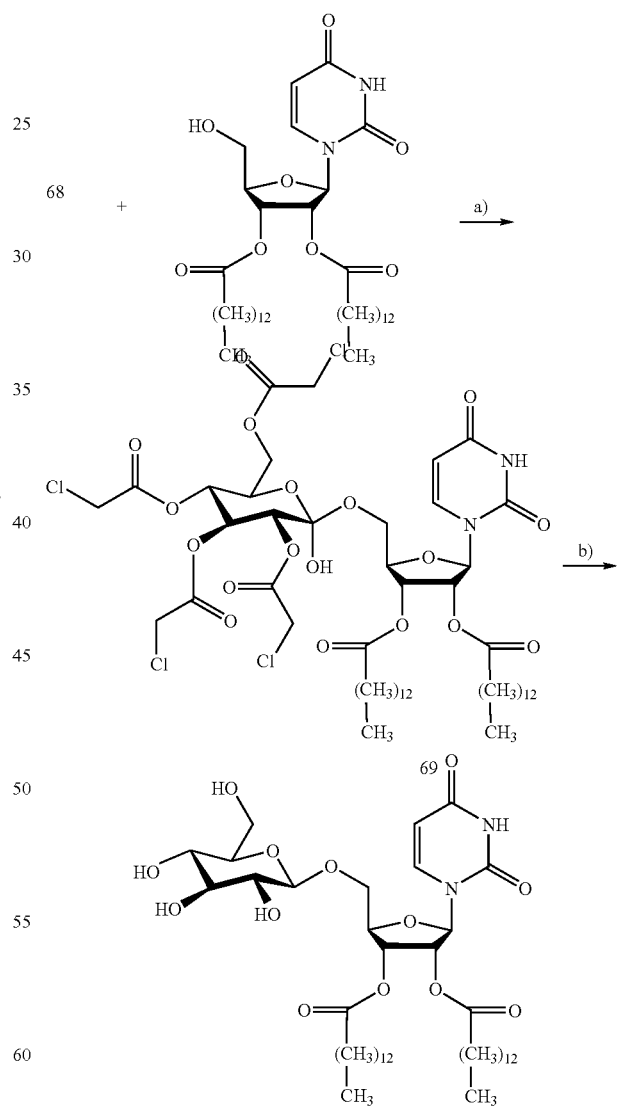

FIG. 22. Synthesis of sugar analog a) BF$_3$—Et$_2$O in CH$_2$Cl$_2$, (Yield = 11%) NH$_4$OAc in MeOH, Heating

2,3,4,6-tetrachloroacetylglucoside-5'-dimeristoyluridine 69

2,3,4,6-tetrachloroacetylglucoside-1-trichloroacetimidate (0.15 g, 1.1 eq), dimeristoyluridine (0.2 g, 1 eq) and BF3-EtO (0.5 mL, 1.1 eq) were dissolved in dry methylchloride. After 12 hours under stirring, solvent was removed under reduced pressure. 0.04 g of product was isolated after chromatography (DCM/MeOH 92/8). (yield: 11%). The characterization data were consistent with the chemical structure.

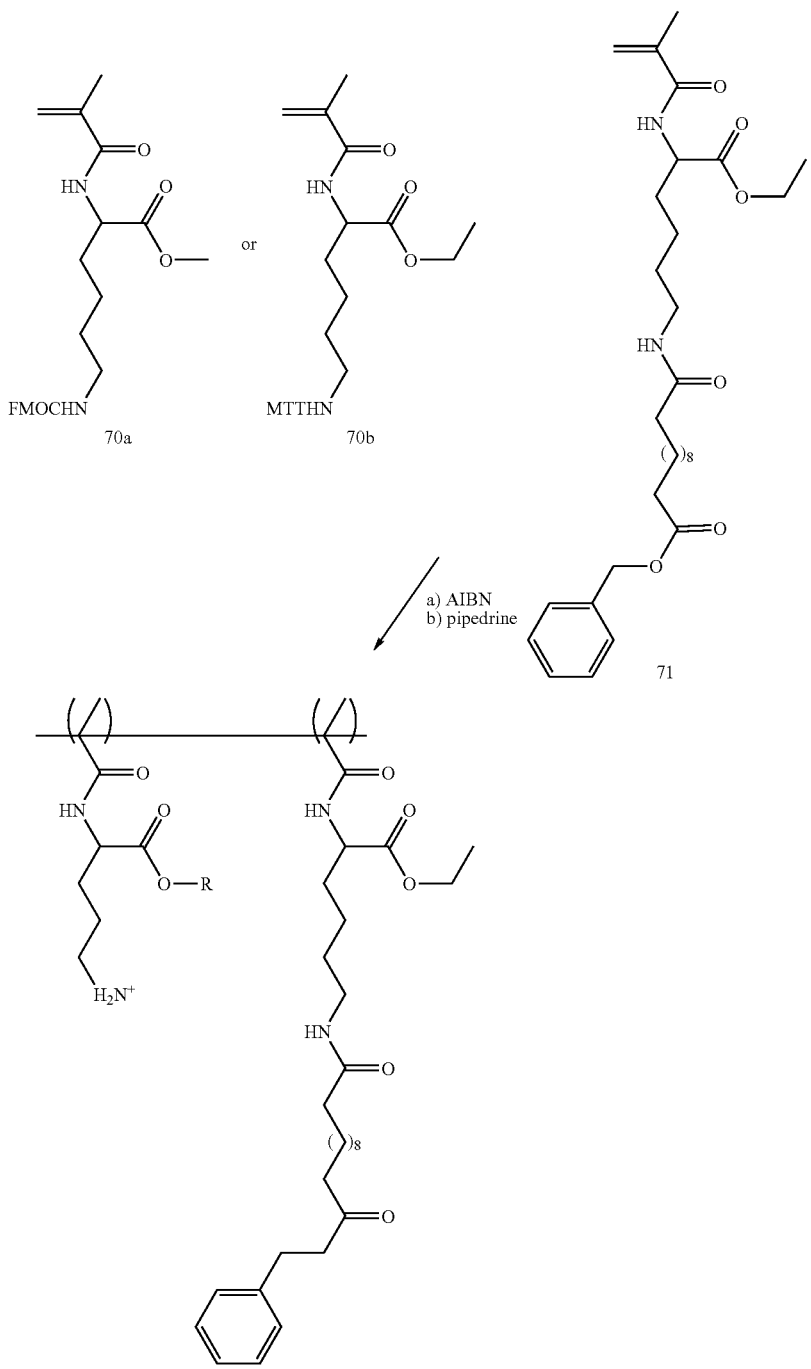

+1; X = 100 Y = 0; 20
+1 to 0; X = 50 Y = 50; 72
+1 to -1; X = 34 Y = 68; 73
+1 to -2; X = 24 Y = 72; 74
+1 to -3; X = 20 Y = 80; 75

FIG. 23. Charge-reversal linear polymer based on polylysine

Example 12

Additional charge reversal polymeric amphiphiles are shown above based on polylysine. Polylysine polymers are reported to transfect DNA. This polymer possesses two components: the cation and the hydrophobic acyl chain with the hydrolysable benzy ester. The ratio of both of these groups can be altered as to afford a polymer that is highly cationic to one that is highly anionic. First, lysine (FMOC, OMe protected) was first methacrylated with methacryloyl chloride in THF with TEA. We have characterized this monomer 70a (NMR, mass spect, EA) and are preparing 70b and 71. We have also polymerized 70a in the presence of AIBN in order to form cationic polymer. (MALDI Mw=20,700). As expected, this polymer binds DNA and displaces EtBr in the ethidium bromide-DNA fluorescence quenching exclusion assay (see description below). Upon hydrolysis of the methyl ester, the polymer becomes neutral and the resulting polymer does not bind DNA. These four polymeric amphiphiles will enable us to modulate the charge reversal properties from +1 to 0 through +1 to −3. It is expected that the −3 polymer will release DNA at a faster rate than the −1 to 0 charged polymer.

Example 13

Amphiphiles 76 through 83 are also included within the scope of this invention. Amphiphiles 80-83 are based on the structure of spermine—a known cationic synthetic vector. These amphiphiles provide a means to further study the effects of charge on DNA binding and release. Amphiphile 83 is an example of a Gemini-like amphiphile. Cationic gemini amphiphiles are known to bind DNA and transfect. For example, amphiphile 76 transforms from a +1 to −1 (similar to 1), whereas amphiphiles 78, 80, and 82 transform from +1 to −3, +2 to 0, and +2 to −2, respectively. We have prepared and characterized 77. The N-methyldiethanolamie was reacted with the corresponding benzylester derivatized dodecanoic acid using DCC/DMAP in dichloromethane. The amine was then methylated with MeI in dichloromethane to afford the final product Amphiphile 81 was synthesized by reacting benzylester derivatized dodecanoic acid with spermine in the presence of DCC in dichloromethane. The other amphiphiles will be synthesized in a similar manner.

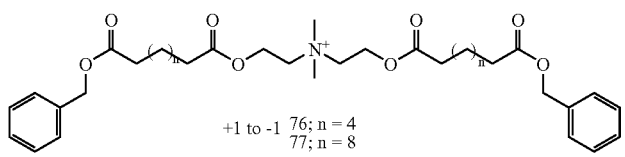

+1 to −1  76; n = 4
77; n = 8

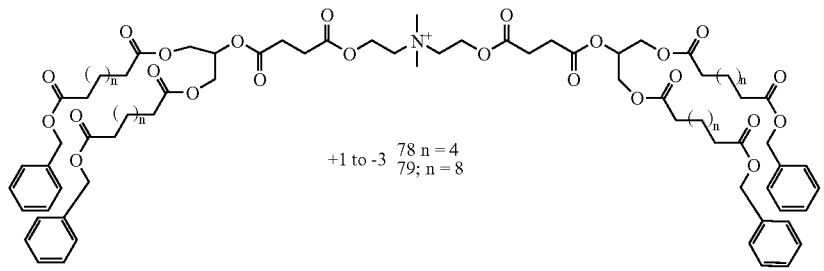

+1 to −3  78 n = 4
79; n = 8

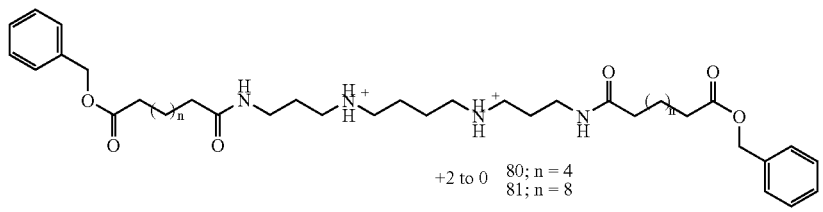

+2 to 0  80; n = 4
81; n = 8

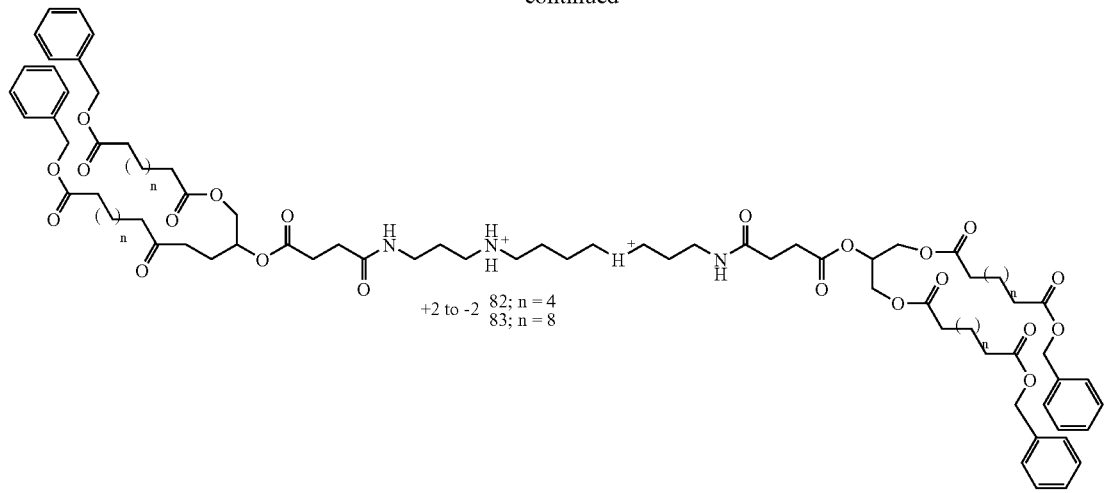

FIG. 24 Bola and Gemini-type charge reversal amphiphiles

Example 14

Amphiphilic dendrimers have also been prepared. Dendrimers 84, 85 and 86 were prepared in a step-wise convergent procedure. The esterification steps used DCC/DMAP in THF or dichloromethane. The bzld intermediates were deprotected using Pd/C and hydrogen. The macromolecules were characterized by NMR and SEC.

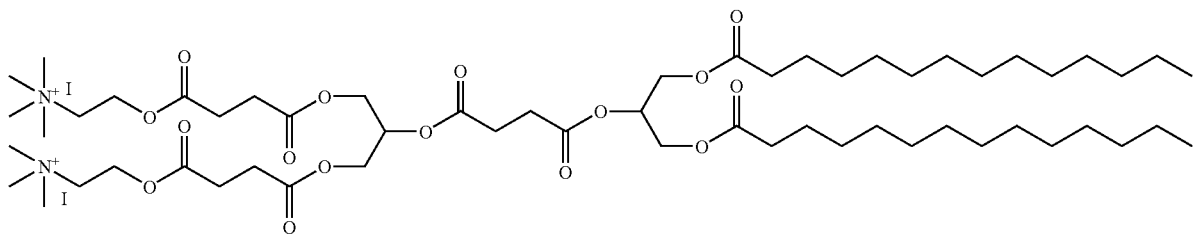

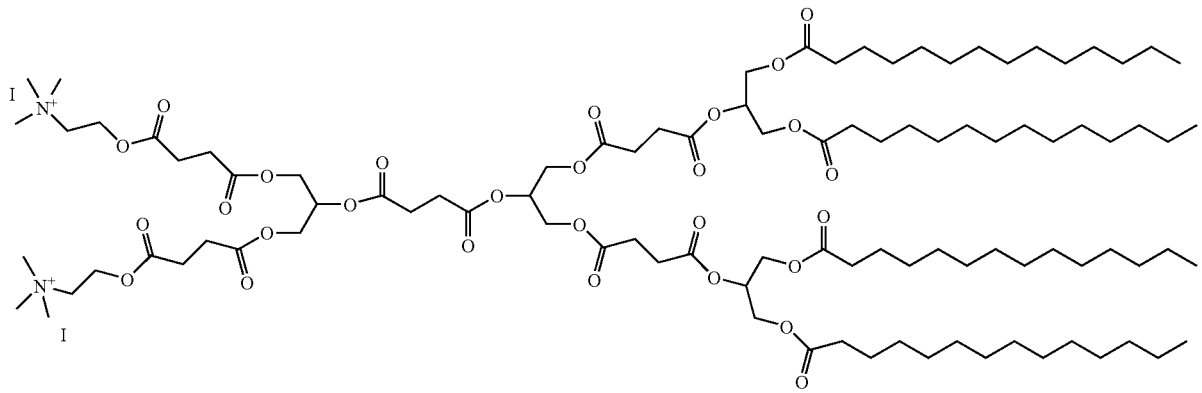

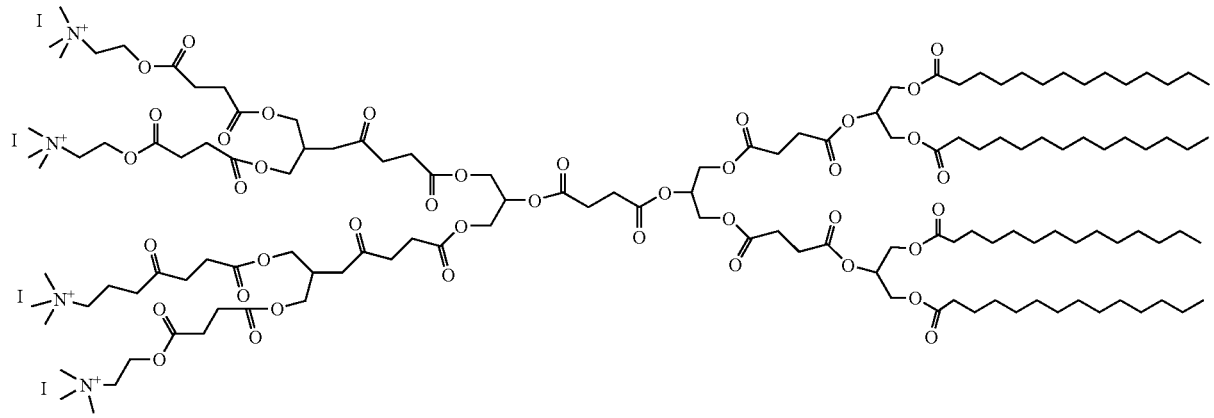

FIG. 25 Amphiphilic dendrimers synthesized

Example 15

Preparation of a Liposome Composition

Liposomes are formed by mixing 1 mg the amphiphilic molecule and 1 mg DOPE (0.5:1 molar ratio). After thorough stirring, the mixture is evaporated to dryness in a round bottomed borosilicate tube using a rotary evaporator. The subsequent dried lipid film is resuspended in a low volume of ethanol or chloroform. Liposomes are formed by adding an excess of distillated water. After homogenization by slight vortexing or sonicating the mixture. Alternatively, the solution can be extruded to afford liposomes.

Preparation of a Liposome-Nucleic Acids Complex Composition

Complex formation of nucleic acids to the liposome bilayer membrane is achieved by simply mixing the pre-formed liposomes to a solution of nucleic acids. Next, the mixture is slightly mixed and incubated for at least 30 min at room temperature.

Example 16

The lipophilic uridine derivatives 2',3'dimyristoyl uridine and 2',3'dipalmitoyl uridine form gels in DMSO. The gels can be produced by either 1) sonication (30 sec) or by heating the suspensions to 60 C for 5 minutes and cooling to room temperature. Compounds bearing the shortest chains were found to be able to form gels in this solvent (See FIG. 17 in Example 10).

Example 17

The amphiphiles 55-58 formed gels in water. The compounds were dissolved in water and then a gel was formed. Gels can also be formed in the presence of plasmid DNA. The gels can be delivered to a specific site, this is advantageous for the delivery of nucleic acids in vivo or in vitro.

Example 18

The amphiphiles 55-58 formed gels in water. The compounds were dissolved in water and then a gel was formed. Gels can also be formed in the presence of plasmid DNA and a known cationic amphiphile such as DOTAP. The gels can be delivered to a specific site, this is advantageous for the delivery of nucleic acids in vivo or in vitro.

Example 19

The AFM images were collected in tapping mode using a Digital Instruments Nanoscope IIIa/Multimode Atomic Force Microscope. The silicon tapping mode AFM tips were purchased from Silicon/MDT (Model NSC-15) and used as received. Typical scanning and feedback parameters are as follows: oscillation frequency, 350 kHZ; integral gain, 0.2; proportional gain, 2.0; setpoint, 1.5V; scan speed, 2 Hz.

Sample Preparation

Preparation of DNA and amphiphiles-DNA solutions. Initially calf thymus DNA and plasmid DNA were imaged in the absence of amphiphiles. 5 µL of an initial calf thymus DNA solution (1 mg/mL) are diluted to 3 mL with buffer (2 mM HEPES, 150 mM $MgCl_2$, 10 µm EDTA, pH 7.4). In the case of the plasmid DNA, 3 µL of the initial solution (0.5 mg/mL) are diluted with 3 mL of the same HEPES-$MgCl_2$ buffer. Amphiphiles-DNA condensates were prepared as following; 3 µL (plasmid DNA initial solution, 0.5 mg/mL) or 5 µL (calf thymus DNA initial solution, 1 mg/ml) of DNA and varying amount of amphiphiles (dependent on the amphiphile/DNA ratio required) were diluted to 1 ml with buffer (2 mM HEPES, 150 mM $MgCl_2$, 10 µm EDTA, pH 7.4). The solutions were mixed and incubated for 60 minutes at room temperature. Each solution was then diluted to 3 mL with the same buffer (2 mM HEPES, 150 mM NaCl, 10 µM EDTA, pH 7.4).

DNA and amphiphiles-DNA on mica. For solution in HEPES-Mg buffer one drop (0.1 mL) of each DNA solution was incubated on a freshly cleaved mica substrate for 5-10 minutes, rinsed twice with distilled water, dried with compressed air and further dried in a desiccator under high vacuum for 1 hour. Amphiphile 4e forms torid structures with plasmid DNA on mica as observed by AFM. The size of the torids is similar to that previously observed with cationic polymers.

Example 20

Exclusion assay (adapted from; A. J. Geall, I. S. Blagbrough, *Journal of Pharmaceutical and Biomedical Analysis* 22 (2000) 849-859)

Five μg (5 μl of 1 mg/mL solution) of DNA and varying amount of amphiphiles (dependent on the Amphiphile/DNA ratio required) were diluted to 1000 μL with buffer (2 mM HEPES, 150 mM NaCl, 10 μm EDTA, pH 7.4). The solutions were mixed on a bench top vortex and incubated for 60 minutes at ambient temperature. Each solution was then diluted to 3 mL with buffer (2 mM HEPES, 150 mM NaCl, 10 μm EDTA, pH 7.4). Immediately prior to the analysis, 3 μL of Eth Br solution (0.6 mg/ml, 1.3 mM, effectively present in excess) was added, the sample was mixed on a bench top vortex, and the fluorescence measured. The fluorescence was expressed as the percentage of the maximum fluorescence signal when EthBr was bound to the DNA in the absence of amphiphile. Assays were run in triplicate. The following molecules or macromolecules bound DNA and displaced EtBr using this assay including 22a-f, 26, 30a, 30b, 34, 44, 47, 77, 81, 84, 85, and 86. Compounds 35 and 36 did not bind DNA and displace EthBr. Compound 30a bound DNA and displaced EthBr. Next an esterase was added to the solution (30a, 34, 77, 81) which cleaved the ester linkages to afford the anionic compound, releasing the DNA from the amphiphile and enabling the EthBr to intercalate in the DNA. This experimental result demonstrates that a functional synthetic vector can bind and release DNA in the presence of an esterase.

Example 21

Transfection assays were performed using the well established B-galactosidase transfection assay. In these experiments the B-galactosidase gene is transfected into cells. Next, the expressed enzyme then cleaves a chemiluminescent reporter that is detected. The assays are conducted with chinese hamster ovary (CHO) cells following a standard lipid transfection procedure. The procedure is performed on varying concentrations of lipid and DNA in triplicate in 96 well plates. Amphiphiles 30a and 40 transfected the B-galactosidase gene. While compounds 35 and 36 showed minimal transfection activity.

INCORPORATION BY REFERENCE

All of the U.S. patents and U.S. published patent applications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound represented by formulas IV:

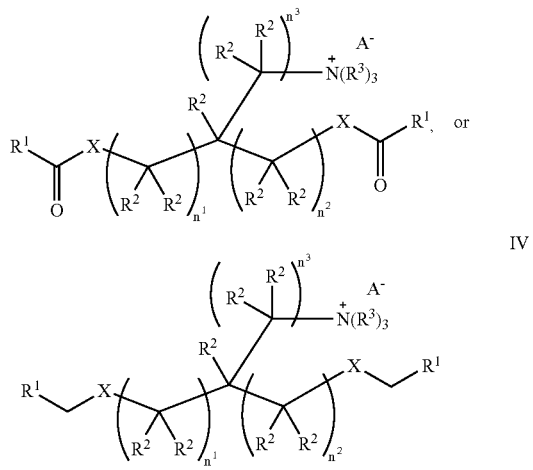

IV wherein
X represents independently for each occurrence O or —N($R^4$)—;
Y represents independently for each occurrence —N($R^4$)—, or —C($R^2$)$_2$—;
Z represents independently for each occurrence O or —N($R^5$)—;
$R^1$ is aryl, aralkyl,

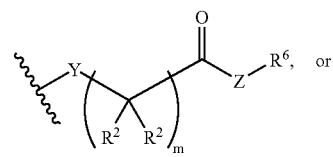

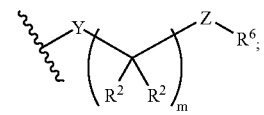

$R^2$ is H, alkyl, or halogen;
$R^3$, $R^4$, and $R^5$ represent independently for each occurrence H, alkyl, aryl, or aralkyl;
$R^6$ is alkyl, aryl, aralkyl, or a photocleavable protecting group having a molecular weight less than 700 g/mol;
m represents independently for each occurrence 5, 6, 7, 8, 9, 10, 11, 12, 13, 14, 15, 16, 17, 18, 19, 20, 21, 22, 23, 24, or 25;
$n^1$, $n^2$, and $n^3$ each represent independently 0, 1, 2, 3, 4, 5, 6, 7, or 8; and
A is an anion with a net charge of negative one.

2. The compound of claim 1, wherein said compound of formula IV is:

129
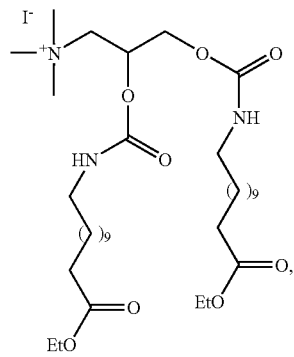 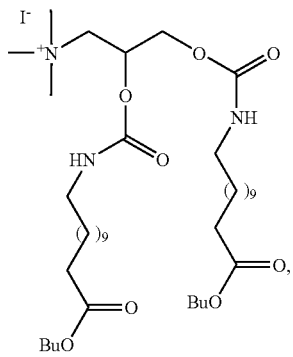 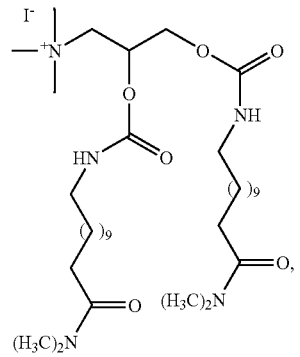
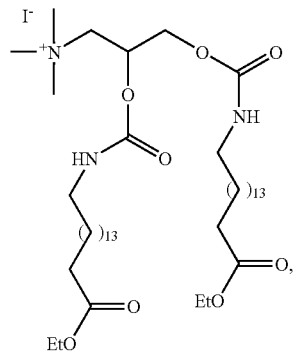 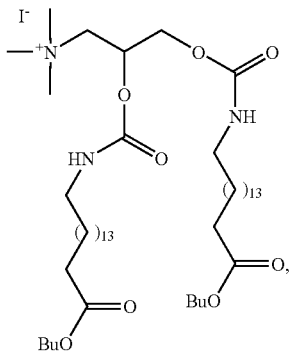 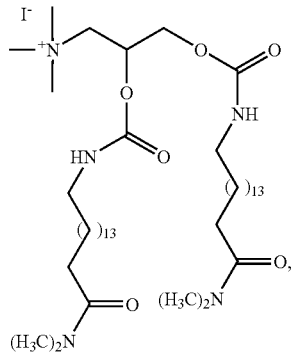
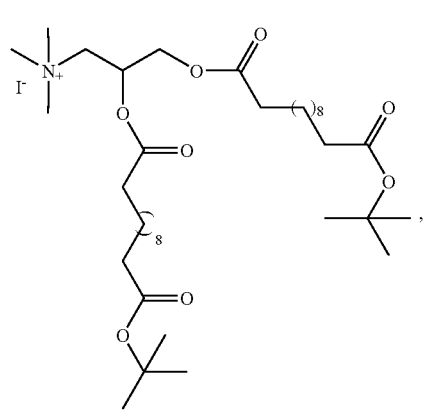 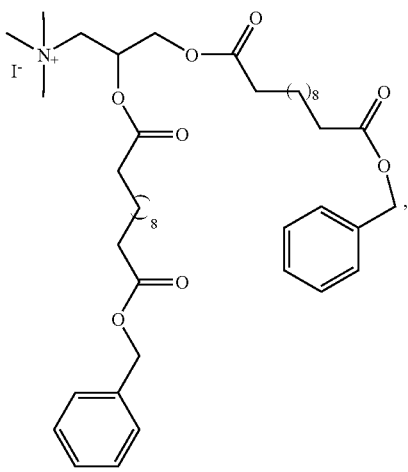
130
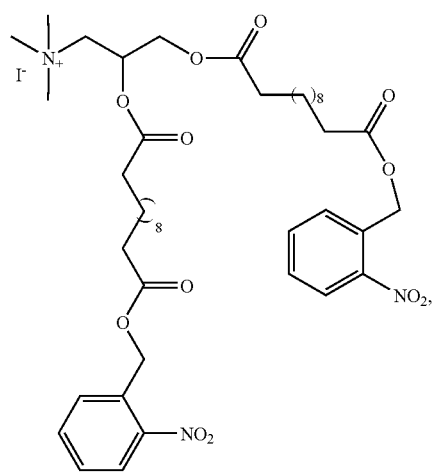

-continued

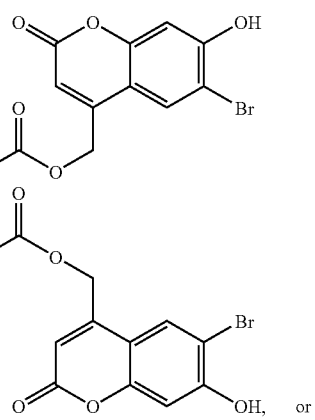
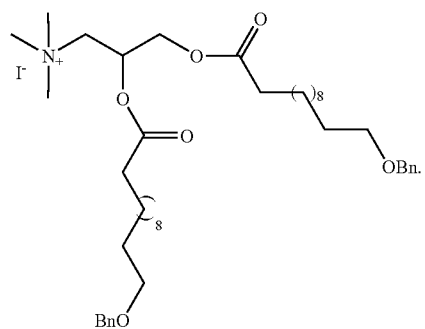
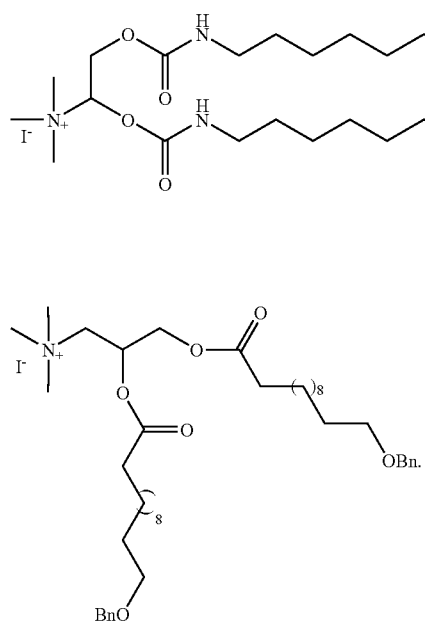

3. A pharmaceutical composition comprising a compound or polymer of any one of claims 1-2; and a nucleic acid.

4. The pharmaceutical composition of claim 3, wherein said nucleic acid is DNA, RNA, plasmid, siRNA, duplex oligonucleotide, single-strand oligonucleotide, triplex oligonucleotide, PNA, or mRNA.

5. The pharmaceutical composition of claim 3 or 4, further comprising DPPC, DMPC, PEGylated DPPC, DPPC, DOPE, DLPC, DMPC, DPPC, DSPC, DOPC, DMPE, DOPE, DPPE, DMPA-Na, DMRPC, DLRPC, DARPC; catonic, anionic, or zwitterionic amphiphile; fatty acid, cholesterol, flourescencetly labeled phospholipid, ether lipid, or sphingolipid.

6. A method of delivering a nucleic acid to a cell, comprising the step of:
    contacting a cell with an effective amount of a mixture comprising a nucleic acid to be delivered to said cell and a compound or polymer of any one of claims 1-2.

7. The method of claim 6, wherein said nucleic acid is DNA, RNA, plasmid, siRNA, duplex oligonucleotide, single-strand oligonucleotide, triplex oligonucleotide, PNA, or mRNA.

8. The method of claim 6 or 7, wherein said cell is a animal cell or plant cell.

9. The method of claim 6 or 7, wherein said cell is a mammalian cell.

10. The method of claim 6 or 7, wherein said cell is a human cell or insect cell.

11. The method of claim 6 or 7, wherein said cell is a human cell.

12. The method of claim 6 or 7, wherein said cell is an embryonic cell or stem cell.

13. The method of claim 6 or 7, wherein said cell is contacted in vivo.

* * * * *